US007993681B2

(12) United States Patent
Roth

(10) Patent No.: US 7,993,681 B2
(45) Date of Patent: Aug. 9, 2011

(54) METHODS, COMPOSITIONS AND DEVICES FOR INDUCING STASIS IN TISSUES AND ORGANS

(75) Inventor: Mark B. Roth, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 1003 days.

(21) Appl. No.: 10/972,063

(22) Filed: Oct. 22, 2004

(65) Prior Publication Data
US 2005/0147692 A1 Jul. 7, 2005

Related U.S. Application Data

(60) Provisional application No. 60/513,458, filed on Oct. 22, 2003, provisional application No. 60/548,150, filed on Feb. 26, 2004, provisional application No. 60/577,942, filed on Jun. 8, 2004.

(51) Int. Cl.
A01N 59/02 (2006.01)
A01N 1/00 (2006.01)
(52) U.S. Cl. .......................................... 424/708; 435/1.1
(58) Field of Classification Search .................. 424/708; 435/1
See application file for complete search history.

(56) References Cited

U.S. PATENT DOCUMENTS

| 1,379,855 | A |   | 5/1921  | Donner ............................. 8/161 |
|-----------|---|---|---------|---------------------------------------|
| 2,031,489 | A |   | 2/1936  | Koenigsberger .................. 8/161 |
| 2,435,854 | A | * | 2/1948  | Taylor ............................. 34/559 |
| 2,487,558 | A |   | 11/1949 | Kamlet ............................. 8/161 |
| 3,587,899 | A | * | 6/1971  | Bender et al. .................. 215/307 |
| 4,186,565 | A |   | 2/1980  | Toledo-Pereyra .............. 62/306 |
| 4,502,295 | A |   | 3/1985  | Toledo-Pereyra .............. 62/463 |
| 4,798,824 | A |   | 1/1989  | Belzer et al. ..................... 514/60 |
| 4,807,442 | A |   | 2/1989  | Linner et al. ................... 62/55.5 |
| 4,920,044 | A | * | 4/1990  | Bretan, Jr. ...................... 435/1.1 |
| 4,923,442 | A |   | 5/1990  | Segall et al. |
| 4,938,961 | A |   | 7/1990  | Collins et al. .................. 424/606 |
| 4,951,482 | A |   | 8/1990  | Gilbert ........................ 62/457.1 |
| 5,066,578 | A |   | 11/1991 | Wikman-Coffelt .............. 435/1 |
| 5,157,930 | A |   | 10/1992 | McGhee et al. .................. 62/78 |
| 5,173,088 | A |   | 12/1992 | Maeda et al. ..................... 23/295 |
| 5,285,657 | A |   | 2/1994  | Bacchi et al. ................. 62/457.9 |
| 5,326,706 | A |   | 7/1994  | Yland et al. .................... 435/283 |
| 5,328,821 | A | * | 7/1994  | Fisher et al. .................. 435/1.3 |
| 5,370,989 | A |   | 12/1994 | Stern et al. ........................ 435/1 |
| 5,395,314 | A |   | 3/1995  | Klatz et al. ..................... 604/24 |
| 5,405,742 | A |   | 4/1995  | Taylor ............................... 435/1 |
| 5,464,768 | A | * | 11/1995 | Kiel et al. ...................... 435/355 |
| 5,476,764 | A |   | 12/1995 | Bitensky ........................... 435/2 |
| 5,552,267 | A |   | 9/1996  | Stern et al. ..................... 435/1.1 |
| 5,569,579 | A |   | 10/1996 | Murphy ............................. 435/2 |
| 5,599,659 | A | * | 2/1997  | Brasile et al. .................. 435/1.1 |
| 5,693,462 | A |   | 12/1997 | Raymond ........................... 435/1 |
| 5,699,793 | A |   | 12/1997 | Brasile ........................... 128/630 |
| 5,719,174 | A |   | 2/1998  | Sainsbury et al. ............. 514/410 |
| 5,736,397 | A |   | 4/1998  | Garcia et al. .................. 435/374 |
| 5,752,929 | A |   | 5/1998  | Klatz et al. ...................... 604/51 |
| 5,770,583 | A |   | 6/1998  | Haslwanter et al. ............ 514/57 |
| 5,791,151 | A |   | 8/1998  | Verhaag et al. .................... 62/78 |
| 5,912,019 | A |   | 6/1999  | Singh ............................. 424/608 |
| 5,948,392 | A |   | 9/1999  | Haslwanter et al. ............ 424/61 |
| 6,013,256 | A |   | 1/2000  | Light et al. .................. 424/133.1 |
| 6,046,046 | A |   | 4/2000  | Hassanein .................. 435/284.1 |
| 6,054,261 | A |   | 4/2000  | Masterson ...................... 435/1.2 |
| 6,100,082 | A |   | 8/2000  | Hassanein .................. 435/284.1 |
| 6,109,260 | A |   | 8/2000  | Bathe ......................... 128/203.12 |
| 6,164,276 | A |   | 12/2000 | Bathe et al. ............... 128/202.22 |
| 6,365,338 | B1|   | 4/2002  | Bull et al. ...................... 435/1.1 |
| 6,490,880 | B1|   | 12/2002 | Walsh .......................... 62/457.9 |
| 6,492,103 | B1|   | 12/2002 | Taylor ............................ 435/1.2 |
| 6,524,785 | B1|   | 2/2003  | Cozzone et al. ............... 435/1.1 |
| 6,552,083 | B1|   | 4/2003  | Isobe et al. ..................... 514/563 |
| 6,557,492 | B1|   | 5/2003  | Robohm ........................ 119/203 |
| 6,602,277 | B2|   | 8/2003  | Grahn et al. .................. 607/108 |
| 6,857,443 | B2|   | 2/2005  | Volgyesi .................... 137/101.19 |
| 6,962,154 | B2|   | 11/2005 | Krebs ....................... 128/203.12 |
| 7,045,140 | B2|   | 5/2006  | Motterlini et al. ............ 424/423 |
| 2002/0068265 | A1 |   | 6/2002 | Lopez et al. ................... 435/1.1 |
| 2002/0155166 | A1 | * | 10/2002 | Choi et al. ..................... 424/600 |
| 2003/0050227 | A1 |   | 3/2003 | Kondo ............................. 514/2 |
| 2003/0176317 | A1 |   | 9/2003 | Guenzler-Pukall et al. ....... 514/1 |
| 2003/0235571 | A1 |   | 12/2003 | Gojon-Romanillos ....... 424/94.1 |
| 2004/0109903 | A1 |   | 6/2004 | Shaklai et al. ................. 424/699 |
| 2004/0254215 | A1 |   | 12/2004 | Arend et al. ................... 514/310 |
| 2005/0136125 | A1 |   | 6/2005 | Roth ............................. 424/600 |
| 2005/0147692 | A1 |   | 7/2005 | Roth ............................. 424/600 |
| 2005/0170019 | A1 |   | 8/2005 | Roth ............................. 424/705 |
| 2005/0217667 | A1 |   | 10/2005 | Dhuper .................... 128/200.23 |
| 2005/0227948 | A1 |   | 10/2005 | Schofield et al. ............ 514/114 |
| 2006/0003972 | A1 |   | 1/2006 | Wallace et al. .............. 514/166 |
| 2006/0270635 | A1 |   | 11/2006 | Wallace et al. .............. 514/109 |
| 2007/0078113 | A1 |   | 4/2007 | Roth et al. |
| 2008/0085329 | A1 |   | 4/2008 | Roth et al. |
| 2008/0171726 | A1 |   | 7/2008 | Roth et al. |

FOREIGN PATENT DOCUMENTS

EP 0 073 590 1/1982

(Continued)

OTHER PUBLICATIONS

Brown, Biochimica et Biophysica Acta, 2001,1504, 46-57.*
Brown et al., Biochem. J., 1996, 315, 295-299.*
Leslie, Science, 2008, 320, 1155-1157.*
Eghbal et al., "H2S cytotoxicity mechanism involves reactive oxygen species formation and mitochondrial depolarisation," *Toxicology*, 203:69-76, 2004.
PCT International Search Report and Written Opinion, issued in International Application No. PCT/US2006/015158, dated Jan. 31, 2007.
Anthony et al., Preservation of viable biological samples for experiments in space laboratories, *J. of Biotechnology*, 45:377-393, 1996.
Database Caplus Chemical Abstract Service. Moser et al. "Octreotide promotes gallbladder absorption om [rairie dogs: a potential cause of gallstones" XPO02319493, STN Accession No. 1995:594873.

(Continued)

*Primary Examiner* — Johann R Richter
*Assistant Examiner* — Abigail Fisher
(74) *Attorney, Agent, or Firm* — Woodcock Washburn LLP

(57) ABSTRACT

The present invention concerns the use of oxygen antagonists for inducing stasis in tissue, including all or part of organs. It includes methods and apparatuses for achieving stasis in tissue, so as to preserve and/or protect them. In specific embodiments, preservation methods and apparatuses for preserving tissue for transplantation purposes is provided.

27 Claims, 18 Drawing Sheets

FOREIGN PATENT DOCUMENTS

| | | |
|---|---|---|
| EP | 0 061 277 | 3/1982 |
| EP | 0 158 728 | 12/1984 |
| EP | 0153215 | 8/1985 |
| EP | 0203730 | 12/1986 |
| EP | 0681558 | 11/1993 |
| EP | 1395241 | 3/2004 |
| FR | 2816212 | 5/2002 |
| WO | WO 84/01292 | 4/1984 |
| WO | WO 91/01638 | 2/1991 |
| WO | WO 94/16991 | 8/1994 |
| WO | WO 94/17178 | 8/1994 |
| WO | WO 96/02461 | 2/1996 |
| WO | WO 98/13058 | 4/1998 |
| WO | WO 01/81546 | 11/2001 |
| WO | WO 01/92874 | 12/2001 |
| WO | WO 02/09514 | 2/2002 |
| WO | WO 02/101018 | 12/2002 |
| WO | WO 03/072024 | 9/2003 |
| WO | WO 03/088981 | 10/2003 |
| WO | WO 04/043341 | 5/2004 |
| WO | WO 2004/060147 | 7/2004 |
| WO | WO 2005/039291 | 5/2005 |
| WO | WO 2005/041655 | 5/2005 |
| WO | WO 2005/041656 | 5/2005 |
| WO | WO 2005/046595 | 5/2005 |
| WO | WO 2005/115075 | 12/2005 |
| WO | WO 2006/085127 | 8/2006 |
| WO | WO 2006/102536 | 9/2006 |
| WO | WO 2006/119258 | 11/2006 |

OTHER PUBLICATIONS

Hogman, "How can we improve platelet preparation and storage?" *Transfus. Sci.*, 17:545-551, 1996.

Nystul and Roth, "Carbon monoxide-induced suspended animation protects against hypoxic damage in *Caenorhabditis elegans*," *The National Academy of the Sciences of the United States of America*, 101:9133-9136, 2004.

Roberts et al., "Two sensor kinases contribute to the hypoxic response of *Mycobacterium tuberculosis*," *J. of Biological Chem.*, 279:23082-23087, 2004.

Australian Application No. 2004285468, Examination Report dated Jun. 23, 2009.

Bagarinao, "Sulphide Tolerance and Adaption in the California Killifish, *Fundulus parvipinnis*, a Salt March Resident," *J. Fish Biology*, 1993, 42, 729-748.

Yanmoto, "Prolonged Mild Hypothermia Therapy Protects the Brain Against Permanent Focal Ischemia," *Stroke*, 2001, 32, 232-239.

United States Patent and Trademark Office: Restriction Requirement dated Jan. 9, 2008, U.S. Appl. No. 10/971,575.

United States Patent and Trademark Office: Non-Final Office Action dated Jun. 19, 2008, U.S. Appl. No. 10/971,575.

United States Patent and Trademark Office: Final Office Action dated Feb. 24, 2009, U.S. Appl. No. 10/971,575.

United States Patent and Trademark Office: Restriction Requirement dated Jan. 8, 2008, U.S. Appl. No. 10/971,576.

United States Patent and Trademark Office: Restriction Requirement dated Sep. 8, 2008, U.S. Appl. No. 11/837,484.

United States Patent and Trademark Office: Non-Final Office Action dated Mar. 20, 2009, U.S. Appl. No. 11/837,484.

Written Opinion of the International Searching Authority, PCT/US2004/035034, Jun. 28, 2005.

Written Opinon of the International Searching Authority, PCT/US2004/035289, Jun. 28, 2005.

Written Opinion of the International Searching Authority, PCT/US2004/034980, Mar. 10, 2005.

Gordon, C.J., "The Therapeutic Potential of Regulated Hypothermia," *Emerg. Med. J.*, 2001, 18, 81-89.

Gordon, *E-Letter response to Science*, 2005, retrievable at http://www.sciencemag.org/cg/eletters/308/5721/518, pp. 1-5.

Haouzi, P. et al., "$H_2S$ Induced Hypometabolism in Mice is Missing in Sedated Sheep," *Respiratory Physiology & Neurobiology*, 2008, 160, 109-115.

Li, J. et al., "Effect of Inhaled Hydrogen Sulfide on Metabolic Responses in Anesthetized, Paralyzed, and Mechanically Ventilated Piglets," *Pediatric Critical Care Medicine*, 2008, 9(1), 110-112.

Struv, M.F. et al., "Neurotoxicological Effects Associated with Short-Term Exposure of Sprague-Dawley Rats to Hydrogen Sulfide," *NeuroToxicology*, 2001, 22, 375-385.

Wall, R.J. et al., "Are Animal Models as Good as We Think?" *Theriogenology*, 2008, 69, 2-9.

United States Patent and Trademark Office: Non-Final Office Action dated Sep. 28, 2009, U.S. Appl. No. 10/971,575.

U.S. Appl. No. 60/673,295, filed Apr. 20, 2005, Roth.

Abe and Kimura, "The possible role of hydrogen sulfide as an endogenous neuromodulator," *J. Neuroscience*, 16:1066-1071, 1996.

Akamatsu et al., "Heme oxygenase-1-derived carbon monoxide protects hearts from transplant-associated ischemia reperfusion injury," *FASEB J.*, Online Edition, Feb. 20, 2004.

Ali et al., "Regulation of vascular nitric oxide in vitro and in vivo; a new role for endogenous hydrogen sulfide?" *Br. J. Pharmacol.*, 149:625-634, 2006.

Almeida and Guidotti, "Differential sensitivity of lung and brain to sulfide exposure: a peripheral mechanism for apnea," *Toxicol. Sci.*, 50:287-293, 1999.

Andersson and Azoulay, "Mechanisms and Kinetics of the Thermal Decomposition of Sodium Sulphide Pentahydrate under Controlled Water Vapour Pressure," *J. Chem. Soc. Dalton Trans.*, pp. 469-475, 1986.

Bak et al., "The role of heme oxygenase-related carbon monoxide and ventricular fibrillation in ischemic/reperfused hearts," *Free Radical Biol Med.*, 33:639-648, 2002.

Barbe et al., "Mechanisms underlying the coronary vasodilation in the isolated perfused hearts of rats submitted to one week of high carbon monoxide exposure in vivo," *Inhalation Toxicol.*, 14:273-285, 2002.

Baskar et al., "Hydrogen sulfide-induces DNA damage and changes in apoptotic gene expression in human lung fibroblast cells," *FASEB J.*, 21:247-255, 2007.

Beck et al., "Effects of tumbling trauma, scalding and hemorrhage on rat tissue non-protein sulfhydryl," *Proc. Soc. Exp. Biol. Med.* 86:823-827, 1954.

Berglin and Carlsson, "Effect of hydrogen sulfide on the mutagenicity of hydrogen peroxide in *Salmonella typhimurium* strain TA102," *Mutation Res.*, 175:5-9, 1986.

Bernard et al., "Treatment of comatose survivors of out-of-hospital cardiac arrest with induced hypothermia," *N. Engl. J. Med.*, 346(8):557-563, 2002.

Bhambhani and Singh, "Physiological effects of hydrogen sulfide inhalation during exercise in healthy men," *J. Appl. Physiol.*, 71:1872-1877, 1991.

Bhatia et al., "Role of hydrogen sulfide in acute pancreatitis and associated lung injury," *FASEB J.*, pp. 1-17, Jan. 25, 2005.

Bhatia et al., "Role of Substance P in Hydrogen Sulfide-Induced Pulmonary Inflammation in Mice," *Am. J. Physiol. Lung Cell. Mol. Physiol.*, 291:L896-904, 2006.

Bhatia et al., "The role of hydrogen sulfide in lung inflammation," *Drug Discov. Today: Dis. Mechanism*, 3:71-75, 2006.

Bian et al., "Role of hydrogen sulphide in the cardioprotection caused by ischemic preconditioning in the rat heart and cardiac myocytes," *J. Pharmacol. Exp. Ther.*, 316:670-678, 2006.

Bickel et al., "Selective Inhibition of Hepatic Collagen Accumulation in Experimental Liver Fibrosis in Ratsw by a New Prolyl 4-Hydroxylase Inhibitor," *Hepatology*, 28:404-411, 1998.

Bishop et al., "Genetic Analysis of Pathways Regulated by the von Hippel-Lindau Tumor Suppressor in *Caenorhabditis elegans*," *PLoS Biol.*, 2:1549-1560, 2004.

Blackstone et al., "H2S Induces a Suspended Animation-Like State in Mice," *Science*, 308:518, 2005.

Brenneman et al., "Olfactory Mucosal Necrosis in Male CD Rats Following Acute Inhalation Exposure to Hydrogen Sulfide: Reversibility and the Possible Role of Regional Metabolism," *Toxicol. Pathol.*, 30:200-208, 2000.

Carlsson et al., "Catalase inhibition by sulfide and hydrogen peroxide-induced mutagenicity in *Salmonella typhimurium* strain TA102," *Mutation Res.*, 202:59-64, 1988.

Chauveau et al., "Gene transfer of heme oxygenase-1 and carbon monoxide delivery inhibit chronic rejection," *Am. J. Transplant.*, 2:581-592, 2002.

Chen and Morris, "Kinetics of Oxidation of Aqueous Sulfide by O2," *Environ. Sci. Technol.*, 6:529-537, 1972.

Chen et al., "Targeted Inactivation of Cystic Fibrosis Transmembrane Conductance Regulator Chloride Channel Gene Prevents Ischemic Preconditioning in Isolated Mouse Heart," *Circulation*, 110:700-704, 2004.

Cheng et al., "Hydrogen sulfide-induced relaxation of resistance mesenteric artery beds of rats," *Am. J. Physiol. Heart Circ. Physiol.*, 287-2316-2323, 2004.

CIIT (Chemical Industry Institute of Toxicology), In: *90 day vapor inhalation toxicity study of hydrogen sulfide in fischer 344 rats*, Toxigenics, 420-0710A, 1983.

CIIT (Chemical Industry Institute of Toxicology), In: *90 day vapor inhalation toxicity study of hydrogen sulfide in sprague-dawley rats*, Toxigenics, 420-0710B, 1983.

CIIT (Chemical Industry Institute of Toxicology), In: *90 day vapor inhalation toxicity study of hydrogen sulfide in B6C3F1 mice*, Toxigenics, 420-0710C, 1983.

Clark et al., "Cardioprotective Actions by a Water-Soluble Carbon Monoxide-Releasing Molecule," *Circ. Res.*, 93:2-8, 2003.

Clark et al., "Heme oxygenase-1-derived bilirubin ameliorates postischemic myocardial dysfunction," *Am. J. Physiol. Heart Circ. Physiol.*, 278:H643-H651, 2000.

Clegg, "Embryos of *Artemia franciscana* survive four years of continuous anoxia: the case for complete metabolic rate depression," *J. Exp. Biol.*, 200:467-475, 1997.

Clementi et al., "On the mechanism by which vascular endothelial cells regulate their oxygen consumption," *Proc. Natl. Acad. Sci. U.S.A.*, 96:1559-1562, 1999.

Cohen et al., "Adaptation to Hydrogen Sulfide of Oxygenic and Anoxygenic Photosynthesis among Cyanobacteria," *Applied Environ. Microbiol.*, 51:398-407, 1986.

Collin et al., "Inhibition of endogenous hydrogen sulfide formation reduces the organ injury caused by endotoxemia," *Br. J. Pharmacol.*, 146:498-505, 2005.

Database Caplus Chemical Abstract Service. Moser et al. "Octreotide promotes gallbladder absorption in prairie dogs: a potential cause of gallstones" XPO02319493, STN Accession No. 1995:594873, 1995.

Denis and Reed, "The action of blood on sulfides," *J. Biol. Chem.*, 72:385-394, 1927.

Distrutti et al., "5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity," *J. Pharmacol. Exp. Therapeutics.*, 319:447-458, 2006.

Distrutti et al., "Evidence that hydrogen sulfide exerts antinociceptive effects in the gastrointestinal tract by activating Katp Channels," *J. Pharmacol. Exp. Therapeutics*, 316:325-335, 2006.

Doeller et al., "Polarographic measurement of hydrogen sulfide production and consumption by mammalian tissues," *Analytical Biochemistry*, 341:40-51, 2005.

Dorman et al., "Cytochrome oxidase inhibition induced by acute hydrogen sulfide inhalation: correlation with tissue sulfide concentrations in the rat brain, liver, lung, and nasal epithelium," *Toxicol. Sci.*, 65:18-25, 2002.

Dorman et al., "Respiratory tract toxicity of inhaled hydrogen sulfide in Fischer-344 rats, Sprague-Dawley rats, and B6C3F1 mice following subchronic (90-day) exposure," *Toxicol. Appl. Pharmacol.*, 198:29-39, 2004.

Dziewiatkowski, "Fate of ingested sulfide sulfur labeled with radioactive sulfur in the rat," *J. Biol. Chem.*, 161:723-729, 1945.

Ebrahimkhani et al., "Hydrogen sulphide and the hyperdynamic circulation in cirrhosis: a hypothesis," *Gut*, 54:1668-1671, 2005.

Fiorucci et al., "Inhibition of Hydrogen Sulfide Generation Contributes to Gastric Injury Caused by Anti-Inflammatory Nonsteroidal Drugs," *Gastroentherology*, 129:1210-1224, 2005.

Fiorucci et al., "The Third Gas: H2S Regulates Perfusion Pressure in Both the Isolated and Perfused Normal Rat Liver in Cirrhosis," *Hepatology*, 42:539-548, 2005.

Foe and Alberts, "Reversible chromosome condensation induced in *Drosophila* embryos by anoxia: visualization of interphase nuclear organization," *J. Cell Biol.*, 100:1623-1636, 1985.

Franklin et al., "Inhibition of prolyl 4-hydroxylase in vitro and in vivo by members of a novel series of phenanthrolinones," *Biochem. J.*, 353:333-338, 2001.

Freeman et al., "SM-20, EGL-9, and the EGLN family of hypoxia-inducible factor prolyl hydroxylases," *Mol. Cells*, 16:1-12, 2003.

Friedman et al., "Prolyl 4-hydroxylase is required for viability and morphogenesis in *Caenorhabditis elegans*," *Proc. Natl. Acad. Sci. USA*, 97:4736-4741, 2000.

Fujimoto et al., "Carbon monoxide protects against cardiac ischemia—reperfusion injury in vivo via MAPK and Akt—eNOS pathways," *Arterioscler. Thromb. Vasc. Biol.*, 24:1848-1853, 2004.

Furne et al., "Oxidation of hydrogen sulfide and methanethiol to thiosulfate by rat tissues: a specialized function of the colonic mucosa," *Biochem. Pharmacol.*, 62:255-259, 2001.

Geng et al., "H2S generated by heart in rat and its effects on cardiac function," *Biochem. Biophys. Res. Commun.*, 313:362-368, 2004.

Giulivi, "Functional implications of nitric oxide produced by mitochondria in mitochondrial metabolism," *Biochem. J.*, 332:673-679, 1998.

Grahn and Keller, "Heat Transfer in Humans : Lessons from Large Hibernators," In: *Life Ain the Cold: Evolution, Mechanisms, Adaptation, and Application. Twelfth International Hibernation Symposium*, Biological Papers of the University of Alaska, (Barnes and Carey, eds.) pp. 81-92, 2004.

Grahn et al., "Heat extraction through the palm of one hand improves aerobic exercise endurance in a hot environment," *J. Appl. Physiol.*, 99:972-978, 2005.

Guo et al., "Administration of a CO-releasing molecule at the time of reperfusion reduces infarct size in vivo," *Am. J. Physiol. Heart Circ. Physiol.*, 286:1649-1653, 2004.

Hand, In: *Surviving hypoxia mechanisms of control and adaptation*, ed. Hochachka, et al., CRC Press, Inc., Boca Raton, pp. 171-185, 1993.

Hays, In: *Studies of the Effects of Atmospheric Hydrogen Sulfide in Animals*, thesis dissertation, University of Missouri-Columbia, 1972.

Hochachka et al., "Mechanism, origin, and evolution of anoxia tolerance in animals," *Comp. Biochem. Physiol. B Biochem. Mol. Biol.*, 130(4):435-459, 2001.

Hochachka, "Defense strategies against hypoxia and hypothermia," *Science*, 231:234-241, 1986.

Ivan et al., "Biochemical purification and pharmacological inhibition of a mammalian prolyl hydroxylase acting on hypoxia-inducible factor," *Proc. Natl. Acad. Sci. USA*, 99:13459-13464, 2002.

Jiang et al., "Changes of the new gaseous transmitter H2S in patients with coronary heart disease," *J. First Mil. Med. Univ.*, 25:951-954, 2005.

Jiang et al., "Intracellular Ca2+ signaling in endothelial cells by the angiogenesis inhibitors endostatin and angiostatin," *Am. J. Physiol. Cell Physiol.*, 280:1140-1150, 2001.

Johansen et al., "Exogenous hydrogen sulfide (H2S) protects against regional myocardial ischemia-reperfusion injury: Evidence for a role of KATP channels," *Brain Res. Cardiol.*, 101:53-60, 2006.

Kage et al., "A fatal case of hydrogen sulfide poisoning in a geothermal power plant," *J. Forensic Sci.*, 43:908-910, 1998.

Kage et al., "Fatal and nonfatal poisoning by hydrogen sulfide at an industrial waste site," *J. Forensic Sci.*, 47:652-655, 2002.

Kage et al., "The usefulness of thiosulfate as an indicator of hydrogen sulfide poisoning: three cases, *Int. J. Legal Med.*," 110:220-222, 1997.

Kage et al., "Usefulness of thiosulfate as an indicator of hydrogen sulfide poisoning in forensic toxicological examination: A study with animal experiments," *Jpn. J. Forensic Toxicol.*, 10:223-227, 1992.

Kaillo et al., "Signal transduction in hypoxic cells: inducible nuclear translocation and recruitment of the CBP/p300 coactivator by the hypoxia-inducible factor-1 alpha," *EMBO J.*, 17:6573-6586, 1998.

Kangas and Savolainen, "Urinary thiosulphate as an indicator of exposure to hydrogen sulphide vapour," *Clinica Chimica Acta*, 164:7-10, 1987.

Kimura and Kimura, "Hydrogen sulfide protects neurons from oxidative stress," *FASEB J.*, 18:1165-1167, 2004.

Kimura et al., "Hydrogen sulfide protects HT22 neuronal cells from oxidative stress," *Antioxid. Redox Signal.*, 8:661-670, 2006.

Kirkby and Adin, "Products of heme oxygenase and their potential therapeutic applications," *Am. J. Physiol. Renal Physiol.*, 290:563-571, 2006.

Kivirikko and Myllyharju, "Prolyl 4-hydroxylases and their protein disulfide isomerase subunit," *Matrix Biol.*, 16:357-368, 1998.

Kleinjan et al., "Equilibrium of the reaction between dissolved sodium sulfide and biologically produced sulfur," *Colloids and Surface B: Biointerfaces*, 43:228-237, 2005.

Kleinjan et al., "Kinetics of the chemical oxidation of polysulfide anions in aqueous solution," *Water Res.*, 39:4093-4100, 2005.

Kondo et al., "Circannual Control of Hibernation by HP Complex in the Brain," *Cell*, 125:161-172, 2006.

Krishnamachary et al., "Regulation of colon carcinoma cell invasion by hypoxia-inducible factor 1," *Cancer Res.*, 63:1138-1143, 2003.

Kubo et al., "Direct inhibition of endothelial nitric oxide synthase by hydrogen sulfide: Contribution to dual modulation of vascular tension," *Toxicology*, 232:138-146, 2007.

Lambert et al., "Hydrogen sulfide (H2S) and sour gas effects on the eye. A historical perspective," *Sci. Total Environ.*, 367:1-22, 2006.

Lewis and Cochrane, "Alteration of sulfate and hydrogen metabolism in the human colon by changing intestinal transit rate," *Am. J. Gastroenterol.*, 102:624-633, 2007.

Li et al., "Hydrogen sulfide is a novel mediator of lipopolysaccharide-induced inflammation in the mouse," *FASEB J.*, 19:1196-1198, 2005.

Li et al., "Hydrogen sulphide—a novel mediator of inflammation?" *Curr. Opin. Pharmacol.*, 6:125-129, 2006.

Lin et al., "Sulfur revisited," *J. American Acad. Dermatol.*, 18:553-558, 1988.

Lundgren-Eriksson et al., "Radio-and chemotoxicity in mice during hypothermia," *Anticancer Res.*, 21(5):3269-74, 2001.

Majamaa et al., "Differences between collagen hydroxylases and 2-oxoglutarate dehydrogenase in their inhibition by structural analogues of 2-oxoglutarate," *Biochem. J.*, 229:127-133, 1985.

Majamaa et al., "The 2-oxoglutarate binding site of prolyl 4-hydroxylase. Identification of distinct subsites and evidence for 2-oxoglutarate decarboxylation in a ligand reaction at the enzyme-bound ferrous ion," *Eur. J. Biochem.*, 138:239-245, 1984.

Mannaioni et al., "Carbon monoxide: the bad and the good side of the coin, from neuronal death to anti-inflammatory activity," *Inflamm. Res.*, 55:261-273, 2006.

Masini et al., "Heme Oxygenase-1 and the Ischemia-Reperfusion Injury in the Rat Heart," *Exp. Biol. Med.*, 228:546-549, 2003.

Milby and Baselt, "Hydrogen Sulfide Poisoning: Clarification of Some Controversial Issues," *Am. J. Industrial. Med.*, 35:192-195, 1999.

Mok et al., "Role of hydrogen sulphide in haemorrhagic shock in the rat: protective effect of inhibitors of hydrogen sulphide biosynthesis," *Br. J. Pharmacol.*, 143:881-889, 2004.

Morse and Choi, "Heme oxygenase-1: from bench to bedside," *Am. J. Respir. Crit. Care Med.*, 172:660-670, 2005.

Moses et al., "Sampling and Analysing Mixtures of Sulphate, Sulphite, Thiosulphate and Polythionate," *Talanta*, 31:331-339, 1984.

Moulin et al., "Predicted regional flux of hydrogen sulfide correlates with distribution of nasal olfactory lesions in rats," *Toxicol. Sci.*, 66:7-15, 2002.

Nakao et al., "Carbon monoxide inhalation protects rat intestinal grafts from ischemia/reperfusion injury," *Am. J Pathol.*, 163:1587-1598, 2003.

Nakao et al., "Ex Vivo Application of Carbon Monoxide in University of Wisconsin Solution to Prevent Intestinal cold Ischemia/Reperfusion Injury," *Am. J. Transplantation*, 6:2243-2255, 2006.

Nakao et al., "Protection against ischemia/reperfusion injury in cardiac and renal transplantation with carbon monoxide, biliverdin and both," *Am. J. Transplant.*, 5:282-291, 2005.

Nashef et al., "Determination of Hydrogen Sulfide with 5,5'-Dithiobis-(2-Nitrobenzoic Acid), N-Ethylmaleimide, and Parachloromercuribenzoate," *Analytical Biochem.*, 79:394-405, 1977.

Nicholson et al., "Inhibition of respiratory and bioenergetic mechanisms by hydrogen sulfide in mammalian brain," *J. Toxicol. Environ. Health Part A*, 54:491-507, 1998.

Nolan et al., "Therapeutic Hypothermia After Cardiac Arrest: An Advisory Statement by the Advanced Life Support Task Force of the International Liaison Committee on Resuscitation," *Circulation*, 108:118-121, 2003.

Oh et al., "Hydrogen sulfide inhibits nitric oxide production and nuclear factor-kappaB via heme oxygenase-1 expression in RAW264.7 macrophage stimulated with lipopolysaccharide," *Free Radical Biol. Med.*, 41:106-119, 2006.

Ott et al., "Inhalation of carbon monoxide prevents liver injury and inflammation following hind limb ischemia/reperfusion," *FASEB J.*, 19:106-108, 2005.

Pan et al., "Endogenous hydrogen sulfide contributes to the cardioprotection by metabolic inhibition preconditioning in the rat ventricular myocytes," *J. Mol. Cell Cardiol.*, 40:119-130, 2006.

Pearson et al., "Endogenous hydrogen sulfide and the cardiovascular system—what's the smell all about?" *Clin. Invest. Med.*, 29:146-150, 2006.

Qu et al., "Hydrogen sulfide is a mediator of Cerebral ischemic damage," *Stroke*, 37:889-893, 2006.

Ramasamy et al., "Sulfide-detoxifying enzymes in the human colon are decreased in cancer and unregulated in differentiation," *Am. J. Physiol. Gastrointest. Liver Physiol.*, 291:288-296, 2006.

Rose et al., "Hydrogen sulfide protects colon cancer cells from chemopreventative agent beta-phenylethyl isothiocyanate induced apoptosis," *World J. Gastroenterol.*, 11:3990-3997, 2005.

Roth et al., "Buying time in suspended animation," *Scientific American*, 292:48-55, 2005.

Sabatier, "Recherches Thermiques Sur Les Sufures," *Ann. Chim. Phys.*, 22:17-98, 1881.

Saitoh et al., "Heart preservation in HTK solution: role of coronary vasculature in recovery of cardiac function," *Ann. Thorac. Surg.*, 69:107-112, 2000.

Schroeter et al., "Incorporation of tissue reaction kinetics in a computational fluid dynamics model for nasal extraction of inhaled hydrogen sulfide in rats," *Toxicol. Sci.*, 90:198-207, 2006.

Schroeter et al., "Use of a Pharmacokinetic-Driven Computational Fluid Dynamics Model to Predict Nasal Extraction of Hydrogen Sulfide in Rats and Humans," ToxSci Advance Access, published Sep. 19, 2006.

Searcy and Peterson, "Hydrogen sulfide consumption measured at low steady state concentrations using a sulfidostat," *Analytical Biochem.*, 324:269-275, 2004.

Shea and Howell, "High-Performance Liquid Chromatographic Measurement of Exogenous Thiosulfate in Urine and Plasma," *Analytical Biochem.*, 140:589-594, 1984.

Shimoda et al., "HIF-1 regulates hypoxic induction of NHE1 expression and alkalinization of intracellular pH in pulmonary arterial myocytes," *Am. J. Physiol. Lung Cell Mol. Physiol.*, 291:941-949, 2006.

Siddiq et al., "Hypoxia-inducible Factor Prolyl 4-Hydroxylase Inhibiton: A target for neuroprotection in the central nervous system," *J Biol. Chem.*, 16:41732-43, 2005.

Sivarajah et al., "The production of hydrogen sulfide limits myocardial ischemia reperfusion injury and contributes to the cardioprotective effects of preconditioning with endotoxin, but not ischemia in the rats," *Shock*, 26:154-161, 2006.

Srilatha et al., "Possible role for the novel gasotransmitter hydrogen sulphide in erectile dysfunction—a pilot study," *Eur. J. Pharm.*, 535:280-282, 2006.

Suarez and Darveau, "Multi-level regulation and metabolic scaling," *J. Exp. Biol.*, 208:1627-1634, 2005.

Tamura et al., "Phase-specific central regulatory systems of hibernation in Syrian hamsters," *Brain Res.*, 1045:88-96, 2005.

Tan et al., "Identification of a novel small-molecule inhibitor of the hypoxia-inducible factor 1 pathway," *Cancer Res.*, 65:605-612, 2005.

The Hypothermia After Cardiac Arrest Study Group, "Mild Therapeutic Hypothermia to Improve the Neurologic Outcome after Cardiac Arrest," *N. Engl. J. Med.*, 346:549-556, 2002.

Truong et al., "Molecular Mechanisms of Hydrogen Sulfide Toxicity," *Drug Metabolism Rev.*, 38:733-744, 2006.
Tsuei and Kearney, "Hypothermia in the trauma patient," *Injury, Int. J. Care Injured*, 35:7-15, 2004.
Vahlkamp et al., "Inhibition of mitochondrial electron transfer in rats by ethanethiol and methanethiol," *Clinical Science*, 56:147-156, 1979.
Vanden Hoek et al., "Induced hypothermia by central venous infusion: Saline ice slurry versus chilled saline," *Crit. Care. Med.*, 32:S425-S431, 2004.
Welsh et al., "The Thioredoxin Redox Inhibitors 1-Methylpropyl 2-Imidazolyl Disulfide and Pleurotin Inhibit Hypoxia-induced Factor 1alpha and Vascular Endothelial Growth Factor Formation," *Mol Cancer Therapeutics*, 2:235-43, 2003.
Whiteman et al., "The novel neuromodulator hydrogen sulfide: an endogenous peroxynitrite 'scavenger'?" *J. Neurochem.*, 90:765-768, 2004.
Wilms et al., "Reactions of mercaptans with cytochrome c oxidase and cytochrome c," *Biochim. Biophys. Acta*, 589:324-335, 1980.
Wingrove et al., "Nitric oxide contributes to behavioral, cellular, and developmental responses to low oxygen in Drosophila," *Cell*, 98:105-114, 1999.
Wowk, "Is hydrogen sulfide the secret to suspended animation?" *Croynics*, Jul./Aug. 2005.
Wu et al., Hydrogen sulfide ameliorates vascular calcification induced by vitamin D3 plus nicotine in rats, *Acta Pharmacologica Sinica*, 27:299-306, 2006.
Wu et al., "Mild Hypothermia Improves Survival after Prolonged, Traumatic Hemorrhagic Shock in Pigs," *J. Trauma*, 59:291-301, 2005.
Wunder et al., "Carbon monoxide, but not endothelin-1, plays a major role for the hepatic microcirculation in a murine model of early systemic inflammation," *Crit. Care Med.*, 33:2323-2331, 2005.
Xiao et al., "Hydrogen sulfide facilitates carotid sinus baroreflex in anesthetized rats," *Acta Pharmacologica Sinica*, 27:294-298, 2006.
Yang et al., "Hydrogen sulfide-induced apoptosis of human aorta smooth muscle cells via the activation of mitogen-activated protein kinases and caspase-3," *FASEB J.*, 18:1782-1784, 2004.
Yusuf et al., "Streptozotocin-induced diabetes in the rat is associated with enhanced tissue hydrogen sulfide biosynthesis," *Biochem. Biophys. Res. Commun.*, 333:1146-1152, 2005.
Zagli et al., "Hydrogen sulfide inhibits human platelet aggregation," *Eur. J. Pharmacol.*, 559:65-68, 2007.
Zanardo et al., "Hydrogen sulfide is an endogenous modulator of leukocyte-mediated inflammation," *FASEB J.*, 20:E1-E8, 2006.
Zhao and Wang, "H2S-induced vasorelaxation and underlying cellular and molecular mechanisms," *Am. J. Physiol. Heart Ciirc. Physiol.*, 283:H474-H480, 2002.
Zhu et al., "Hydrogen sulfide and its cardioprotective effects in myocardial ischemia in experimental rats," *J. Appl. Physiol.*, Oct. 12, 2006 (article in press).
Zuckerbraun et al., "Carbon monoxide protects against the development of experimental necrotizing enterocolitis," *Am. J. Physiol. Heart Circ. Physiol.*, 289:607-613, 2005.
Alam et al., "Heme oxygenase-1: past, present, and future," *Antioxid Redox Signal*, 4(4):559-562, 2002.
Amersi et al., "Ex vivo exposure to carbon monoxide prevents hepatic ischemia/reperfusion injury through p38 MAP kinase pathway," *Hepatology*, 35(4):815-823, 2002.
Behringer et al., "Survival without brain damage after clinical death of 60-120 mins in dogs using suspended animation by profound hypothermia," *Crit Care Med*, 31(5):1523-1531, 2003.
Bellamy et al., "Suspended animation for delayed resuscitation," *Crit Care Med*, 24(2 Suppl):S24-47, 1996.
Brouard et al., "Heme oxygenase-1-derived carbon monoxide requires the activation of transcription factor NK-κB to protect endothelial cells from tumor necrosis factor-α-mediated apoptosis," *J. Biol. Chem.*, 277(20):17950-17961, 2002.
Dorman et al., "Fertility and developmental neurotoxicity effects of inhaled hydrogen sulfide in Sprague-Dawley rats," *Neurotoxicol Teratol*, 22(1):71-84, 2000.

Dulak et al., "Forum original research communication: heme oxygenase activity modulates vascular endothelial growth factor synthesis in vascular smooth muscle cells," *Antioxid Redox Signal*, 4(2):229-240, 2002.
Eto et al., "Brain hydrogen sulfide is severely decreased in Alzheimer's disease," Biochem Biophys Res Commun, 293:1485-1488, 2002.
Gilbert et al., "Resuscitation from accidental hypothermia of 13.7° C with circulatory arrest," *The Lancet*, 355:375-376, 2000.
Gorman et al., "The clinical toxicology of carbon monoxide," *Toxicology*, 187(1):25-38, 2003.
Guillemin et al., "The hypoxic response: huffing and HIFing," *Cell*, 89(1):9-12, 1997.
Hasse et al., "Resuscitation with 100% oxygen causes intestinal glutathione oxidation and reoxygenation injury in asphyxiated newborn piglets," 240(2):364-373, 2004.
Higuchi and Fukamachi, *Folia Pharmacoligica Japonica*, 73(3):307-319, 1997( in Japanese with English explanations of figures).
Hochachka et al., "Unifying theory of hypoxia tolerance: molecular/metabolic defense and rescue mechanisms for surviving oxygen lack," *Proc. Natl. Acad. Sci., USA*, 93(18):9493-9438, 1996.
Hyspler et al., "A simple, optimized method for the determination of sulphide in whole blood by GC-MS as a marker of bowel fermentation processes," *J Chromatography*, 770:255-259, 2002.
Kabulus et al., "The mechanism of the delay phenomenon: tissue protection is mediated by heme oxygenase-1," *Am J Physiol Heart Circ Physiol*, 2004.
Khan et al., "Effects of hydrogen sulfide exposure on lung mitochondrial respiratory chain enzymes in rats," *Toxicol Applied Pharmacol*, 103:482-490, 1990.
Kilburn and Warshaw, "Hydrogen sulfide and reduced-sulfur gases adversely affect neurophysiological functions," *Toxicology Indust Health*, 11(2):185-197, 1995.
Kilburn, "Measuring the effects of chemicals on the brain," *Environ Health*, 54(3):150, 1999.
Kilburn, "Neurotoxicity from airborne chemicals around a superfund site," *Environ Res*, 81(2):92-99, 1999.
Nystul et al., "Suspended animation in C. elegans requires the spindle checkpoint," *Science*, 302(5647):1038-1041, 2003.
Otterbein et al., "Heme oxygenase: colors of defense against cellular stress," *Am J Physiol Lung Cell Mol Physiol*, 279(6):L1029-L1037, 2000.
Otterbein et al., "Heme oxygenase-1: unleashing the protective properties of heme," *Trends Immunol*, 24(8):449-455, 2003.
Padilla et al., "Dephosphorylation of cell cycle-regulated proteins correlates with anoxia-induced suspended animation in *Caenorhabditis elegans*," *Molec Biology of the Cell*, 13:1473-1483, 2002.
Padilla et al., "Oxygen deprivation causes suspended animation in the zebrafish embryo," *Proc. Natl. Acad. Sci., USA*, 98(13):7331-7335, 2001.
Partlo et al., "Effects of repeated hydrogen sulphide (H2S) exposure on learning and memory in the adult rat," *Neurotoxicology*, 22(2):177-189, 2001.
Petersen, "The effect of inhibitors on the oxygen kinetics of cytochrome c oxidase," *Biochim Biophys Acta*, 460:299-307, 1977.
Rogers et al., "Behavioral and functional analysis of mouse phenotype: SHIRPA, a proposed protocol for comprehensive phenotype assessment," *Genome*, 8:711-713, 1997.
Ryter and Otterbein, "Carbon Monoxide in biology and medicine," *BioEssays*, 26:270280, 2004.
Safar et al., "Suspended animation for delayed resuscitation from prolonged cardiac arrest that is unresuscitable by standard cardiopulmonary cerebral resuscitation," *Crit Care Med*, 28(11 Suppl):N214-218, 2000.
Semenza, "Hypoxia-inducible factor 1: oxygen homeostasis and disease pathology," *Trends Mol Med*, 7(8):345-350, 2001.
Struve et al., "Neurotoxicological effects associated with short-term exposure of Sprague-Dawley rats to hydrogen sulfide," *Neurotoxicology*, 22(3):580-587, 2001.
Teodoro and O'Farrell, "Nitric oxide-induced suspended animation promotes survival during hypoxia," *EMBO J*, 22(3):580-587, 2003.

Tisherman, "Suspended animation for resuscitation from exsanguinating hemorrhage," *Crit Care Med*, 32(2 Suppl):S46-S50, 2004.

Van Voorhies et al., "Broad oxygen tolerance in the nematode *Caenorhabditis elegans*," *J Exp Biol*, 203(Pt 16):2467-2478, 2000.

Wang, "Two's company, three's a crowd: can $H_2S$ be the third endogenous gaseous transmitter?" *FASEB J*, 16(13):1792-1798, 2002.

Yaffe et al., "Smart aortic arch catheter: moving suspended animation from the laboratory to the field," *Crit Care Med*, 32(2 Suppl,):S51-S55, 2004.

Zhang et al., "Whole-body hypoxic preconditioning protects mice against acute hypoxia improving lung function," *J Appl Physiol*, 96(1):392-397, 2004.

Anthony et al., "Preservation of viable biological samples for experiments in space laboratoris," *J of Biotechnology*, 47:377-393, 1996.

Hand, "Quiescence in *Artemia franciscana* embryos: reversible arrest of metabolism and gene expression at low oxygen levels," *J Experimental Biology*, 201:1233-1242, Abstract, 1998.

Hand, "Induction of quiescence and diapause during life cycles of aquatic invertebrates: mechanisms and implications," *American Zoologist*, 40:1044-1045, 2000, Abstract.

Hogman, "How can we improve platelet preparation and storage," *Transfus. Sci.*, 17:545-551, 1996.

Nystul and Roth, "Carbon monoxide-induced suspended animation protects against hypoxic damage in *Caenorhabditis elegans*," *PNAS*, 101:9133-9136, 2004.

Roberts et al., "Two sensor kinases contribute to the hypoxic response of *Mycobacterium tuberculosis*," *J of Biological Chemistry*, 279:23082-23087, 2004.

Australian Application No. 20042885468, Examination Report dated Sep. 23, 2010, 2 pages.

Brouard et al. "Carbon monoxide generated by heme oxygenase 1 suppresses endothelial cell apoptosis", The Journal of Experimental Medicine, Oct. 2, 2000, 192(7), 1015-1026.

Nystul et al., "Carbon monoxide-induced suspended animation protects against hypoxic damage in *Caenorhabditis elegans*", PNAS, Jun. 15, 2004, vol. 101, No. 24, pp. 9133-9136.

Sato et al. "Carbon Monoxide Generated by Heme Oxygenase-1 Suppresses the Rejection of Mouse-to-Rat Cardiac Transplants", J of Immunology, Mar. 15, 2001, 166(6), 4185-4194.

\* cited by examiner

FIG. 8A-B

METHODS, COMPOSITIONS AND DEVICES FOR INDUCING STASIS IN TISSUES AND ORGANS

CROSS-REFERENCE TO RELATED APPLICATIONS

This application claims priority to provisional patent application Ser. No. 60/513,458, filed on Oct. 22, 2003, provisional patent application Ser. No. 60/548,150, filed on Feb. 26, 2004, and provisional patent application Ser. No. 60/577,942, filed on Jun. 8, 2004, all of which are hereby incorporated by reference.

STATEMENT REGARDING FEDERAL SPONSORED RESEARCH OR DEVELOPMENT

The government may own rights in the present invention pursuant to grant number GM048435 from the National Institute of General Medical Sciences (NIGMS).

BACKGROUND OF THE INVENTION

1. Field of the Invention

The present invention relates generally to the field of cell biology More particularly, it concerns methods and apparatuses for inducing stasis in isolated tissues and/or organs using a substance that competes with oxygen. In certain embodiments, there are methods and apparatuses for preserving isolated tissue and/or organs.

2. Description of Related Art

Stasis is a latin term meaning "standstill." In the context of stasis in living tissues, the most common forms of stasis relate to the preservation of tissues for transplant or reattachment. Typically, such tissues are immersed in a physiologic fluid, such as saline, and placed in the cold to reduce biochemical processes leading to cellular damage. This stasis is incomplete and cannot be relied upon for extended periods. In fact, the success of organ transplant and limb reattachments is inversely related to the time the organ or limb is out of contact with the intact organism.

A more extreme version of stasis involves placing an entire organism into what is known colloquially as "suspended animation." Though still considered largely within the realm of science fiction, some notoriety has been achieved when wealthy individuals have sought to be cryopreserved after death in the hopes that future medical breakthroughs will permit their revival, and cure of their fatal ailments. Allegedly, more than one hundred people have been cryopreserved since the first attempt in 1967, and more than one thousand people have made legal and financial arrangements for cryonics with one of several organizations, for example, Alcor Life Extension Foundation. Such methods involve the administration of anti-ischemic drugs, low temperature preservation, and methods to perfuse whole organisms with cryosuspension fluids.

The utility of inducing stasis in biological matter as contemplated by the compositions, methods or articles of manufacture described herein, is characterized by induction or onset of stasis followed by a period of time in which the stasis is maintained, followed then by reversion to a normal or near normal physiological state, or a state that one skilled in the art would recognize as a state that is better than the state of the biological matter had it never undergone stasis, in whole or in part.

Stasis can also be defined as what it is not. Organismal stasis is not any of the following states: sleep, comatose, death, anesthetized, or grand mal seizure.

There are numerous reports of individuals who have survived apparent cessation of pulse and respiration after exposure to hypothermic conditions, usually in cold-water immersion. Though not fully understood by scientists, the ability to survive such situations likely derives from what is called the "mammalian diving reflex." This reflex is believed to stimulate the vagal nervous system, which controls the lungs, heart, larynx and esophagus, in order to protect vital organs. Presumably, cold-water stimulation of nerve receptors on the skin causes shunting of blood to the brain and to the heart, and away from the skin, the gastro-intestinal tract and extremities. At the same time, a protective reflex bradycardia, or slowing the heart beat, conserves the dwindling oxygen supplies within the body. Unfortunately, the expression of this reflex is not the same in all people, and is believed to be a factor in only 10-20% percent of cold-water immersion cases.

Compositions and methods that do not rely fully or at all on hypothermia and/or oxygen may be useful in the context of organ preservation, as well as for tissue or cell preservation. Cells and tissue are currently preserved using hypothermia, frequently at temperatures substantially below freezing, such as in liquid nitrogen. However, dependence on temperature can be problematic, as apparatuses and agents for producing such low temperatures may not be readily available when needed or they may require replacement. For example, tissue culture cells are often stored for periods of time in tanks that hold liquid nitrogen; however, these tanks frequently require that the liquid nitrogen in the unit be periodically replaced, otherwise it becomes depleted and the temperature is not maintained. Furthermore, damage to cells and tissue occurs as a result of the freeze/thaw process. Thus, improved techniques are needed.

Moreover, the lack of ability to control cellular and physiologic metabolism in whole organisms subjected to traumas such as amputation and hypothermia is a key shortcoming in the medical field. On the other hand, the anecdotal evidence discussed above strongly suggests that if properly understood and regulated, it is possible to induce stasis in cells, tissues and possible whole organisms. Thus, there is a great need for improved methods for controlling metabolic processes under traumatic conditions.

SUMMARY OF THE INVENTION

Therefore, the present invention provides methods, compositions, articles of manufacture, and apparatuses to induce stasis in tissue that are not contained within an organism ("isolated tissue"). The invention is based on studies with compounds that were determined to have a protective function, and thus, serve as protective agents. Moreover, the overall results of studies involving different compounds indicate that compounds with an available electron donor center are particularly effective in inducing stasis. In addition, these compounds induce reversible stasis, meaning they are not so toxic to the particular biologic matter that the matter dies or decomposes. Such compounds can be used in methods, articles of manufacture, and apparatuses to protect, preserve, and/or extend the longevity of the tissue. Tissue in a state of stasis or that have undergone stasis can be used in a number of applications. They can be used, for example, for transfusion or transplantation (therapeutic applications, including organ transplants); for research purposes; for screening assays to identify, characterize, or manufacture other compounds that induce stasis; for testing a sample from which the tissue was obtained (diagnostic applications); for preserving or preventing damage to the tissue that will be placed back into the organism from which they were derived (preventative applications); and for preserving or preventing damage to them during transport or storage. Details of such applications and other uses are described below.

The present invention concerns methods for inducing stasis in isolated tissue comprising: a) identifying the tissue in which stasis is desired; and, b) exposing the tissue to an effective amount of an oxygen antagonist to induce stasis. Inducing "stasis" in a tissue means that the tissue is alive but is characterized by one or more of the following: at least a two-fold reduction in the rate or amount of carbon dioxide production by the biological matter; at least a two-fold reduction in the rate or amount of oxygen consumption by the biological matter; and at least a 10% decrease in movement or motility (applies only to organs that exhibit movement, such as a beating heart) (collectively referred to as "cellular respiration indicators"). In methods of the invention, stasis is temporary and/or reversible, meaning that the biological matter no longer exhibits the characteristics of stasis at some later point in time. The term "biological matter" refers to any living biological material (mammalian biological material in preferred embodiments) including cells, tissues, organs, and/or organisms, and any combination thereof. The term "in vivo biological matter" refers to biological matter that is in vivo, i.e., still within or attached to an organism. In some embodiments of the invention, biological matter is not in vivo biological matter. Moreover, the term "biological matter" will be understood as synonymous with the term "biological material."

The term "isolated tissue" means that the tissue is not located within an organism. In some embodiments, the tissue is all or part of an organ. The terms "tissue" and "organ" are used according to their ordinary and plain meanings. Thought tissue is composed of cells, it will be understood that the term "tissue" refers to an aggregate of similar cells forming a definite kind of structural material. Moreover, an organ is a particular type of tissue.

The term "oxygen antagonist" refers to a substance that competes with oxygen insofar as it used by a biological matter that requires oxygen for it to be alive ("oxygen-utilizing biological matter"). Oxygen is typically used or needed for various cellular processes that create the biological matter's primary source of readily utilizable energy. An oxygen antagonist effectively reduces or eliminates the amount of oxygen that is available to the oxygen-utilizing biological matter, and/or the amount of oxygen that can be used by the oxygen-utilizing biological matter. Thus, in some embodiments an oxygen antagonist inhibits or reduces the amount of cellular respiration occurring in the cells, for instance, by binding sites on cytochrome c oxidase that would otherwise bind to oxygen. Cytochrome c oxidase specifically binds oxygen and then converts it to water. Preferably, the binding to cytochrome c oxidase by the oxygen antagonist is specific. In some embodiments, such binding to cytochrome c oxidase is preferably releasable and reversible binding (e.g., has an in vitro dissociation constant, $K_d$, of at least $10^{-2}$, $10^{-3}$, or $10^{-4}$ M, and has an in vitro dissociation constant, $K_d$, not greater than $10^{-6}$, $10^{-7}$, $10^{-8}$, $10^{-9}10^{-10}$, or $10^{-11}$ M). In some embodiments, an oxygen antagonist is evaluated by measuring ATP and/or carbon dioxide output.

The term "effective amount" means an amount that can achieve the stated result. In methods of the invention, an "effective amount" is, for example, an amount that induces stasis in the tissue. It will be understood that when inducing stasis in a tissue or organ, an effective amount is one that induces stasis in the tissue or organ as determined by the collective amount of cellular respiration of the tissue or organ. Accordingly, for example, if the level of oxygen consumption by a heart (collectively with respect to cells of the heart) is decreased at least about 2-fold after exposure to a particular amount of a certain oxygen antagonist, it will be understood that that was an effective amount to induce stasis in the heart.

The concept of an effective amount of a particular compound is related to how much utilizable oxygen there is available to the biological matter. Generally, stasis can be induced when there is about 100,000 ppm or less of oxygen in the absence of any oxygen antagonist (room air has about 210, 000 ppm oxygen). The oxygen antagonist serves to alter how much oxygen is effectively available. Thus, while the actual concentration of oxygen that biological matter is exposed to may be higher, even much higher, than 10 ppm, stasis can be induced because of the competitive effect of an oxygen antagonist with oxygen for binding to essential oxygen metabolizing proteins in the biological matter. In other words, an effective amount of an oxygen antagonist reduces the effective oxygen concentration to a point where the oxygen that is present cannot be used. This will happen when the amount of an oxygen antagonist reduces the effective oxygen concentration below the $K_m$ of oxygen binding to essential oxygen metabolizing proteins (i.e., comparable to 10 ppm of oxygen). Accordingly, in some embodiments, an oxygen antagonist reduces the effective concentration of oxygen by about 2-, 3-, 4-, 5-, 6-, 7-, 8-, 9-, 10-, 15-, 20-, 25-, 30-, 35-, 40-, 45-, 50-, 60-, 70-, 80-, 90-, 100-, 150-, 200-, 250-, 300-, 350-, 400-, 450-, 500-, 600-, 700-, 800-, 900-, 1000-, 1100-, 1200-, 1300-, 1400-, 1500-, 1600-, 1700-, 1800-, 1900-, 2000-, 2100-, 2200-, 2300-, 2400-, 2500-, 2600-, 2700-, 2800-, 2900-, 3000-, 3100-, 3200-, 3300, 3400-, 3500-, 3600-, 3700-, 3800-, 3900-, 4000-, 4100-, 4200-, 4300-, 4400-, 4500-, 5000-, 6000-, 7000-, 8000-, 9000-, or 10000-fold or more, or any range derivable therein. It is understood that this is another way of indicating a decrease in cellular respiration.

Moreover, the effective amount can be expressed as a concentration with or without a qualification on length of time of exposure. In some embodiments, it is generally contemplated that to induce stasis, tissue is exposed to an oxygen antagonist for about, at least about, or at most about 5, 10, 15, 20, 25, 30, 35, 40, 45, 50, 55, 60 seconds, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. Thereafter, biological matter may continue to be exposed to an oxygen antagonist, or, in other embodiments of the invention, the biological matter may no longer be exposed to the oxygen antagonist. This latter step can be achieved either by removing or effectively removing the oxygen antagonist from the presence of the biological matter, or the biological matter may be removed from an environment containing the oxygen antagonist.

Therefore, in some embodiments of the invention, stasis is induced, and a further step in methods of the invention is to maintain tissue in a state of stasis. This can be accomplished by continuing to expose tissue to an oxygen antagonist and/or exposing the tissue to a non-physiological or controlled temperature. Alternatively, the tissue may be placed in a preservation agent or solution, or be exposed to normoxic or hypoxic conditions. It is contemplated that tissue may be maintained in stasis for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein.

The term "expose" is used according to its ordinary meaning to indicate that biological matter is subjected to an oxygen antagonist. This can be achieved in some embodiments by contacting biological matter with an oxygen antagonist. Exposing tissue to an oxygen antagonist can be by incubation in or with (includes immersion) the antagonist, perfusion or infusion with the antagonist, injection of the tissue with an oxygen antagonist, or applying an oxygen antagonist to the tissue/organ or to a surface on which the tissue/organ lays and/or are in close proximity to. These are all ways in which the oxygen antagonist is administered to isolated tissue.

In some embodiments, an effective amount is characterized as a sublethal dose of the oxygen antagonist. A "sublethal dose" means a single administration of the oxygen antagonist that is less than half of the amount of the oxygen antagonist that would cause at least a majority of cells in the tissue to die within 24 hours of the administration. In other embodiments, an effective amount is characterized as a near-lethal dose of the oxygen antagonist. A "near lethal dose" means a single administration of the oxygen antagonist that is within 25% of the amount of the inhibitor that would cause at least a majority of cells of the tissue to die within 24 hours of the administration. In some embodiments a sublethal dose is administered by administering a predetermined amount of the oxygen antagonist to the biological material.

In some embodiments an effective amount is administered by monitoring, alone or in combination, the amount of oxygen antagonist administered, monitoring the duration of administration of the oxygen antagonist, monitoring a physiological response (e.g., pulse, respiration, pain response, movement or motility, etc.) of the biological material to the administration of the oxygen antagonist and reducing, interrupting or ceasing administration of the oxygen antagonist when a predetermined floor or ceiling for a change in that response is measured, etc. Moreover, these steps can be employed additionally in any method of the invention.

In certain embodiments, biological matter is exposed to an amount of an oxygen antagonist that reduces the rate or amount of carbon dioxide production by the biological matter at least 2-fold, but also by about, at least about, or at most about 3-, 4-, 5-, 6-, 7-, 8-, 9-, 10-, 15-, 20-, 25-, 30-, 35-, 40-, 45-, 50-, 100-, 200-, 300-, 400-, 500-fold of more, or any range derivable therein. In still further embodiments, biological matter is exposed to an amount of an oxygen antagonist that reduces the rate or amount of oxygen consumption by the biological matter at least 2-fold, but also by about, at least about, or at most about 3-, 4-, 5-, 6-, 7-, 8-, 9-, 10-, 15-, 20-, 25-, 30-, 35-, 40-, 45-, 50-, 100-, 200-, 300-, 400-, 500-fold of more, or any range derivable therein. In still further embodiments, biological matter is exposed to an amount of an oxygen antagonist that decreases movement or motility by at least 10%, but also by about, at least about, or at most about 15, 20, 25, 30, 35, 40, 45, 50, 55, 60, 65, 70, 75, 80, 85, 90, 95, 99, or 100%, or any range derivable therein.

Additionally, in some embodiments of the invention, methods are provided for reducing cellular respiration, which may or may not be as high as that needed to reach stasis. A reduction in oxygen consumption by about, at least about, or at most about 20, 25, 30, 35, 40, 45, 50, 55, 60, 65, 70, 75, 80, 85, 90, 95, or 100% is provided in methods of the invention. This can also be expressed and assessed in terms of any cellular respiration indicator.

It is contemplated that biological matter may be exposed to one or more oxygen antagonists more than one time. It is contemplated that biological matter may be exposed to one or more oxygen antagonists 1, 2, 3, 4, 5, 6, 7, 8, 9, 10 or more times, meaning when a biological matter is exposed multiple times that there are periods of respite (with respect to exposure to the oxygen antagonist) in between.

In some cases a sublethal collective dose or a nonlethal collective dose is administered to the biological matter. As discussed above, with respect to inducing stasis in biological matter that is not an entire organism, a "sublethal collective dose" means an amount of multiple administrations of the oxygen antagonist that collectively is less than half of the amount of the oxygen antagonist that would cause at least a majority of cell(s) to die within 24 hours of one of the administrations. In other embodiments, an effective amount is characterized as a near-lethal dose of the oxygen antagonist. Likewise, a "near lethal collective dose" means an amount of multiple administrations of the oxygen antagonist that is within 25% of the amount of the oxygen antagonist that would cause at least a majority of cell(s) to die within 24 hours of the one of the administrations. It is contemplated that multiple doses can be administered so as to induce stasis in the whole organism. The definition for "sub-lethal collective dose" and "near-lethal collective dose" can be extrapolated based on the individual doses discussed earlier for stasis in whole organisms.

It is contemplated that the tissue can be from any source that has oxygen-utilizing cells. More particularly, in some embodiments, the tissue is from a mammal. Mammals from which tissue can be used with the invention include, but are not limited to those that are from a: human, monkey, mouse, rat, rabbit, hamster, goat, pig, dog, cat, ferret, cow, sheep, and horse.

Moreover, tissue can be selected from the group consisting of: heart, lung, kidney, liver, bone marrow, pancreas, skin, bone, vein, artery, cornea, blood, small intestine, large intestine, larynx, brain, spinal cord, smooth muscle, nerves, skeletal muscle, ovary, testis, uterus, and umbilical cord. All or part of a number of these organs are used for transplantation purposes. Moreover, it is contemplated that a combination of different types of tissue may be used in methods of the invention. For example, transplant of a hand involves different tissues and different cell types.

Biological matter may be exposed to or contacted with more than one oxygen antagonist. Biological matter may be exposed to at least one oxygen antagonist, including 2, 3, 4, 5, 6, 7, 8, 9, 10 or more oxygen antagonists, or any range derivable therein. With multiple oxygen antagonists, the term "effective amount" refers to the collective amount of oxygen antagonists. For example, the biological matter may be exposed to a first oxygen antagonist and then exposed to a second oxygen antagonist. Alternatively, biological matter may be exposed to more than one oxygen antagonists at the same time or in an overlapping manner. Furthermore, it is contemplated that more than one oxygen antagonist may be comprised or mixed together, such as in a single composition to which biological matter is exposed.

Methods and apparatuses of the invention involve a protective agent, that in some embodiments is an oxygen antagonist. In still further embodiments, the oxygen antagonist is a reducing agent.

In still further embodiments, the oxygen antagonist is a chalcogenide compound. In certain embodiments, the chalcogenide compound comprises sulfur, while in others, it comprises selenium, tellurium, or polonium. In certain embodiments, a chalcogenide compound contains one or more exposed sulfide groups. It is contemplated that this chalcogenide compounds contains 1, 2, 3, 4, 5, 6 or more exposed sulfide groups, or any range derivable therein. In particular embodiments, such a sulfide-containing compound is $CS_2$ (carbon disulfide).

Moreover, in some methods of the invention, stasis is induced in the tissue/organ by exposing the tissue/organ to a reducing agent that has a chemical structure of

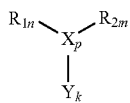

wherein X is N, O, Po, S, Se, or Te;
wherein Y is N or O;
wherein $R_1$ is H, C, lower alkyl, a lower alcohol, or CN;
wherein $R_2$ is H, C, lower alkyl, or a lower alcohol, or CN;
wherein n is 0 or 1;
wherein m is 0 or 1;
wherein k is 0, 1, 2, 3, or 4; and,
wherein p is 1 or 2.

The terms "lower alkyl" and "lower alcohol" are used according to their ordinary meanings and the symbols are the ones used to refer to chemical elements. This chemical structure will be referred to as the "reducing agent structure" and any compound having this structure will be referred to as a reducing agent structure compound. In additional embodiments, k is 0 in the reducing agent structure. Moreover, in other embodiments, the $R_1$ and/or $R_2$ groups can be an amine or lower alkyl amine. In others, $R_1$ and/or $R_2$ could be a short chain alcohol or a short chain ketone. Additionally, $R_1$ and $R_2$ may be bridged and/or the compound may be a cyclic compound. In still further embodiments, X may also be a halogen. The term "lower" is meant to refer to 1, 2, 3, 4, 5, or 6 carbon atoms, or any range derivable therein. Moreover, $R_1$ and/or $R_2$ may be other small organic groups, including, $C_2$-$C_5$ esters, amides, aldehydes, ketones, carboxylic acids, ethers, nitriles, anhydrides, halides, acyl halides, sulfides, sulfones, sulfonic acids, sulfoxides, and/or thiols. Such substitutions are clearly contemplated with respect to $R_1$ and/or $R_2$. In certain other embodiments, $R_1$ and/or $R_2$ may be short chain versions of the small organic groups discussed above. "Short chain" means 1, 2, 3, 4, 5, 6, 7, 8, 9, 10, 11, or 12 carbon molecules, or any range derivable therein.

It is contemplated that the reducing agent structure compound can be a chalcogenide compound in some cases. In certain embodiments, the chalcogenide compound has an alkyl chain with an exposed chalcogenide. In others, the chalcogenide compound has a chalcogenide that becomes exposed once it is taken up by the biological matter. In this respect, the chalcogenide compound is similar to a prodrug as an oxygen antagonist. Therefore, one or more sulfur, selenide, oxygen, tellurium, polonium, or ununhexium molecules on the compound becomes available subsequent to exposure of the biological matter to the chalcogenide compound. In this context, "available" means that the sulfur, selenide, oxygen, tellurium, polonium, or ununhexiim will retain an electron.

In still further embodiments, the reducing agent structure compound is selected from the group consisting of $H_2S$, $H_2Se$, $H_2Te$, and $H_2Po$. In some cases, the reducing agent structure has an X that is an S. In others, X is Se, or X is Te, or X is Po, or X is O. Furthermore, k in the reducing agent structure is 0 or 1 in some embodiments. In certain embodiments, the reducing agent structure compound is dimethylsulfoxide (DMSO), dimethylsulfide (DMS), carbon monoxide, methylmercaptan ($CH_3SH$), mercaptoethanol, thiocyanate, hydrogen cyanide, methanethiol (MeSH), or dimethylsulfide ($CS_2$). In particular embodiments, the oxygen antagonist is $H_2S$, $H_2Se$, $CS_2$, MeSH, or DMS. Compounds on the order of the size of these molecules are particularly contemplated (that is, within 50% of the average of their molecular weights).

Moreover, it will be generally understood that any compound discussed herein as an oxygen antagonist can be provided in prodrug form to the biological matter, meaning that the biological matter or other substance(s) in the environment of the biological matter alters the prodrug into its active form, that is, into an oxygen antagonist.

The oxygen antagonist is provided to the tissue/organ in a state that allows the antagonist to compete with oxygen. The oxygen antagonist may be a gas, semi-solid liquid (such as a gel or paste), liquid, or solid. It is contemplated that biological matter may be exposed to more than one oxygen antagonist and/or to an oxygen antagonist in more than one state.

In certain embodiments, the oxygen antagonist is a gas. In particular embodiments, the gaseous oxygen antagonist includes carbon monoxide, nitrogen, sulfur, selenium, tellurium, or polonium, or a mixture thereof. Moreover, it is specifically contemplated that an oxygen antagonist is a chalcogenide compound as a gas. In some embodiments, the oxygen antagonist is in a gas mixture comprising more than one gas. The other gas(es) is a non-toxic and/or a non-reactive gas in some embodiments. In some embodiments, the other gas is a noble gas (helium, neon, argon, krypton, xenon, radon, or ununoctium), nitrogen, nitrous oxide, hydrogen, or a mixture thereof.

In some instances, the gas mixture also contains oxygen. An oxygen antagonist gas is mixed with oxygen to form an oxygen gas mixture in other embodiments of the invention. Specifically contemplated is an oxygen gas mixture in which the amount of oxygen in the oxygen gas mixture is less than the total amount of all other gas or gases in the mixture.

In some embodiments, the oxygen antagonist gas is carbon monoxide and the amount of carbon monoxide is about the same or exceeds any amount of oxygen in the oxygen gas mixture. In particular embodiments, carbon monoxide is employed with blood-free biological matter. The term "blood-free biological matter" refers to cells and organs whose oxygenation is not dependent, or no longer dependent, on the vasculature, such as an organ for transplant. Preferably, the atmosphere will be 100% CO, but as will be evident to one skilled in the art, the amount of CO may be balanced with gases other than oxygen providing that the amount of usable oxygen is reduced to a level that prevents cellular respiration. In this context, the ratio of carbon monoxide-to-oxygen is preferably 85:15 or greater, 199:1 or greater or 399:1 or greater. In certain embodiments, the ratio is about, at least about, or at most about 1:1, 2:1, 2.5:1, 3:1, 4:1, 5:1, 6:1, 7:1, 8:1, 9:1, 10:1, 15:1, 20:1, 25:1, 30:1. 35:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, 300:1, 310:1, 320:1, 330:1, 340:1, 350:1, 360:1, 370:1, 380:1, 390:1, 400:1, 410:1, 420:1, 430:1, 440:1, 450:1, 460:1, 470:1, 480:1, 490:1, 500:1 or more, or any range derivable therein.

In still further embodiments, the above numbers pertain to the ratio of carbon monoxide to a mixture of oxygen and one or more other gases. In some cases, it is contemplated that the other gas is a nonreactive gas such as nitrogen ($N_2$). Thus, in other embodiments of the invention, the above numbers apply to ratios of carbon monoxide to a combination of oxygen and nitrogen ($O_2/N_2$) that can be used in methods and apparatuses of the invention. Accordingly, it will be understood that other gases may or may not be present. In some embodiments, the CO:oxygen ratio is balanced with one or more other gases (non-carbon monoxide and non-oxygen gases). In particular embodiments, the CO:oxygen ratio is balanced with nitrogen. In still further embodiments, the amount of CO is a ratio of CO compared to room air, as is described by the numbers above.

In some cases, the amount of carbon monoxide is relative to the amount of oxygen, while in others, it is an absolute amount. For example, in some embodiments of the invention, the amount of oxygen is in terms of "parts per million (ppm)" which is a measure of the parts in volume of oxygen in a million parts of air at standard temperature and pressure of 20° C. and one atmosphere pressure and the balance of the gas volume is made up with carbon monoxide. In this context, the amount of carbon monoxide to oxygen is related in terms of parts per million of oxygen balanced with carbon monoxide. It is contemplated that the atmosphere to which the biological material is exposed or incubated may be at least 0, 50, 100, 200, 300, 400, 500, 1000, or 2000 parts per million (ppm) of oxygen balanced with carbon monoxide and in some cases carbon monoxide mixed with a non-toxic and/or non-reactive gas The term "environment" refers to the immediate environment of the biological matter, that is, the environment with which it is in direct contact. Thus, the biological matter must be directly exposed to carbon monoxide, and it is insufficient that a sealed tank of carbon monoxide be in the same room as the biological matter and be considered to be incubated an "environment" according to the invention. Alternatively, the atmosphere may be expressed in terms of kPa. It is generally understood that 1 million parts=101 kPa at 1 atmosphere. In embodiments of the invention, the environment in which a biological material is incubated or exposed to is about, at least about, or at most about 0.001, 0.005, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20. 0.21, 0.22, 0.23, 0.24, 0.25, 0.26, 0.27, 0.28, 0.29, 0.30, 0.35, 0.40, 0.45, 0.50, 0.55, 0.60, 0.65, 0.70, 0.75, 0.80, 0.5, 0.90, 0.95, 1.0 kPa or more $O_2$, or any range derivable therein. As described above, such levels can be balanced with carbon monoxide and/or other non-toxic and/or non-reactive gas(es) Also, the atmosphere may be defined in terms of CO levels in kPa units. In certain embodiments, the atmosphere is about, at least about, or at most about 1, 5, 10, 15, 20, 25, 30, 35, 40, 45, 50, 55, 60, 65, 70, 75, 80, 85, 90, 95, 101, 101.3 kPa CO, or any range derivable therein. In particular embodiments, the partial pressure is about or at least about 85, 90, 95, 101, 101.3 kPa CO, or any range derivable therein.

The amount of time the sample is incubated or exposed to carbon monoxide can also vary in embodiments of the invention. In some embodiments, the sample is incubated or exposed to carbon monoxide for about, for at least about, or for at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more minutes and/or, 1, 2, 3, 4, 5, 6, 7, 8, 9, 10, 11, 12, 13, 14, 15, 16, 17, 18, 19, 20, 21, 22, 23, 24, hours, and/or 1, 2, 3, 4, 5, 6, 7, 8, 9, 10 or more days.

Biological matter is exposed to the gas in a closed container in some embodiments of the invention. In some cases, the closed container can maintain a particular environment or modulate the environment as is desired. The environment refers to the amount of oxygen antagonist that the biological matter is exposed and/or the temperature of the environment. In some cases, the biological matter is placed under a vacuum before, during, or after exposure to an oxygen antagonist. Moreover, in other cases, the biological matter is exposed to a normoxic environment after being exposed to an oxygen antagonist.

Moreover, in other embodiments, the environment containing the biological matter cycles at least once to a different amount or concentration of the oxygen antagonist, wherein the difference in amount or concentration is by at least one percentage difference. The environment may cycle back and forth between one or more amounts or concentrations of the oxygen antagonist, or it may gradually increase or decrease the amount or concentrations of an oxygen antagonist. In some cases, the different amount or concentration is between about 0 and 99.9% of the amount or concentration of the oxygen antagonist to which the biological matter was initially exposed. It is contemplated that the difference in amount and/or concentration is about, at least about, or at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

Methods of the invention can also include a step of subjecting biological matter to a controlled temperature environment. In certain embodiments, the biological matter is exposed to a temperature that is a "non-physiological temperature environment," which refers to a temperature in which the biological matter cannot live in for more than 96 hours. The controlled temperature environment can have a temperature of about, at least about, or at most about −210, −200, −190, −180, −170, −160, −150, −140, −130, −120, −110, −100, −90, −80, −70, −60, −50, −40, −30, −20, −10, −5, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200° C. or more, or any range derivable therein. Biological matter may also be exposed to an oxygen antagonist at room temperature, which means a temperature between about 20° C. and about 25° C. Furthermore, it is contemplated the biological matter achieves a core temperature of any amount or range of amounts discussed.

It is contemplated that the biological matter can be subjected to a non-physiological temperature environment or a controlled temperature environment during or after exposure to the oxygen antagonist(s). Furthermore, in some embodiments, the biological matter is subjected to a non-physiological temperature environment or a controlled temperature environment for a period of time between about one minute and about one year. The amount of time may be about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein. Moreover, there may also be a step of increasing the ambient temperature relative to the reduced temperature.

Moreover, it is contemplated that the temperature may be altered or cycled during the process. In some embodiments, the temperature of the biological matter may first be reduced before it is placed in the environment that has the oxygen antagonist, while in others, the biological matter may be cooled by placing it in the oxygen antagonist environment, that is below the temperature of the biological matter. The biological matter and/or environment may be cooled or heated gradually, such that the temperature of the biological matter or environment starts at one temperature but then reaches another temperature.

In certain embodiments, methods include modulating environmental oxygen levels or removing the biological material from an environment having oxygen. Operationally, exposing biological material to an environment in which oxygen is diminished or absent may mimic exposure of the biological material to an oxygen antagonist.

In methods of the invention, there also is a step of assessing the level of the oxygen antagonist and/or oxidative phosphorylation in the biological matter in which stasis was induced.

Compositions, methods, and articles of manufacture of the invention can be used on biological matter that will be transferred back into the donor organism from which it was derived (autologous) or a different recipient (heterologous) subject. In some embodiments, biological matter is obtained directly from a donor organism. In others, the biological matter is placed in culture prior to exposure to an oxygen antagonist. In some situations, the biological matter is obtained from a donor organism administered extracorporeal membrane oxygenation prior to retrieval of the biological matter, which is a technique implemented to aid in the preservation of biological matter. Moreover, methods include administering or implanting the biological matter in which stasis was induced to a live recipient organism.

In preferred embodiments, an organ or tissue to be retrieved and then transplanted is exposed to the oxygen antagonist while still in the donor subject. It is contemplated that in some cases, the vasculature of the donor is used to expose the organ or tissue to the oxygen antagonist. This can be done if the heart is still pumping or a pump, catheter, or syringe can be used to administer the oxygen antagonist into the vasculature for delivery to the organ or tissue.

Methods of the invention also concern inducing stasis in isolated tissue comprising incubating the tissue with an oxygen antagonist that creates hypoxic conditions for an effective amount of time for the tissue to enter stasis.

Furthermore, other embodiments of the invention include methods of reducing oxygen demand in isolated tissue comprising contacting the tissue with an effective amount of an oxygen antagonist to reduce its oxygen demand. It is contemplated that oxygen demands is reduced about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any range derivable therein, with respect to the amount of oxygen demand in the cells of the tissue or a representative sample of cells not exposed or no longer exposed to the oxygen antagonist.

Other aspects of the invention concern methods for preserving a tissue that is separate from an organism comprising contacting the tissue with an effective amount of an oxygen antagonist to preserve the majority of cells constituting the tissue. In the case of tissues from a recently deceased organism, it is contemplated that the tissues may be exposed to the oxygen antagonist within about or within at least about 30 seconds, 1, 2, 3, 4, 5, 10, 15, 20, 25, 30, 35, 40, 45, 50, 55 minutes, 1, 2, 3, 4 hours or more, and any combination or range derivable therein, of its being retrieved (separated) from the deceased organism.

The invention also concerns a method for inducing stasis in isolated tissue comprising incubating the tissue with an oxygen antagonist for an effective amount of time to render conditions hypoxic induce the tissue to enter stasis.

In certain embodiments of the invention, there is a method for delaying the effects of a trauma on the tissue comprising exposing the tissue to a sub-lethal dose of an oxygen antagonist. In other aspects, there is a method for preserving tissue ex vivo comprising contacting the tissue with a sub-lethal dose of a chalcogenide compound.

Methods of the invention can involve employing an apparatus or system that maintains the environment in which biological matter is placed or exposed to. The invention includes an apparatus in which an oxygen antagonist, particularly as a gas, is supplied. In some embodiments, the apparatus includes a container with a sample chamber for holding the biological matter, wherein the container is connected to a supply of gas comprising the oxygen antagonist(s). It is specifically contemplated that the container may be a solid container or it may flexible, such as a bag.

In some embodiments, the invention is an apparatus for preserving tissue/organ, the apparatus comprising: a container having a sample chamber with a volume of no greater than 775 liters; and a first gas supply in fluid communication with the sample chamber, the first gas supply including carbon monoxide. In further embodiments, the apparatus also includes a cooling unit that regulates the temperature inside the sample chamber and/or a gas regulator that regulates the amount of oxygen antagonist in the chamber or the amount of oxygen antagonist in a solution that is in the chamber.

It is contemplated that there may be a gas supply for a second or additional gas or a second or additional gas supply for the oxygen antagonist. The second gas supply may be connected with the sample chamber or it may be connected with the first gas supply. The additional gas, as discussed above, may be a non-toxic and/or non-reactive gas.

A gas regulator is part of the apparatus in some embodiments of the invention. One, two, three, or more gas regulators may be employed. In some cases, the gas regulator regulates the gas supplied to the sample chamber from the first gas supply. Alternatively, it regulates the gas supplied to the sample chamber or first gas supply from the second gas supply, or there may be a regulator for both the first and second gas supplies. It is further contemplated that any gas regulator can be programmed to control the amount of gas supplied to the sample chamber and/or to another gas supply. The regulation may or may not be for a specified period of time. There may be a gas regulator, which may or may not be programmable, for any gas supply directly or indirectly connected to the sample chamber. In some cases, the gas regulator is electronically programmable.

In some cases, the pressure and/or the temperature inside the chamber can be regulated with either a pressure regulator or temperature regulator, respectively. As with the gas regulator, these regulators may be electronically programmable. The apparatus of the invention may also have a cooling and/or heating unit to achieve the temperatures discussed above. The unit may or may not be electronically programmable.

In additional embodiments, the apparatus includes a wheeled cart on which the container rests or it may have one or more handles.

It is specifically contemplated that the invention includes an apparatus for cell(s), in which the apparatus has: a container having a sample chamber; a first gas supply in fluid communication with the sample chamber, the first gas supply including the oxygen antagonist(s); and an electronically-programmable gas regulator that regulates gas supplied to the sample chamber from the first gas supply.

In some embodiments, the apparatus also has a structure configured to provide a vacuum within the sample chamber.

Moreover, any oxygen antagonist described in this application is contemplated for use with apparatuses of the invention. In specific embodiments, carbon monoxide can be administered using this apparatus. In other cases, a chalcogenide compound can be administered or a compound having the reducing agent structure.

Additionally, the present invention concerns screening assays. In some embodiments, a candidate substance is screened for the ability to act as an oxygen antagonist. This can be done using any assay described herein, such as by measuring carbon dioxide output. Any substance identified as having exhibiting characteristics of an oxygen antagonist can be further characterized or tested. Moreover, it is contemplated that such a substance can be administered to biological matter to induce stasis or manufactured thereafter.

It will be understood that any oxygen antagonist can be used in the preparation of a medicament for the treatment of any disease or condition requiring implantation or transplantation of live tissue, such as for treating myocardial ischemia, loss of an organ or organ function, loss of a limb, loss of eyesight, loss of vocal abilities, cancer (including leukemia), neurodegenerative diseases or conditions, bowel diseases or conditions, liver diseases or conditions, kidney diseases or conditions, eye diseases or conditions, heart diseases or conditions, liver diseases or conditions, kidney and/or pancreas diseases or conditions, nerve damage or loss, larynx diseases or conditions, lung diseases or conditions, uterus diseases or conditions, genitourinary diseases or conditions, reproductive conditions or diseases, blood diseases or conditions, immune system diseases or conditions, burns, bone loss, skin loss, or disfiguration.

Any embodiment discussed with respect to one aspect of the invention applies to other aspects of the invention as well.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Stasis

Figure 1:
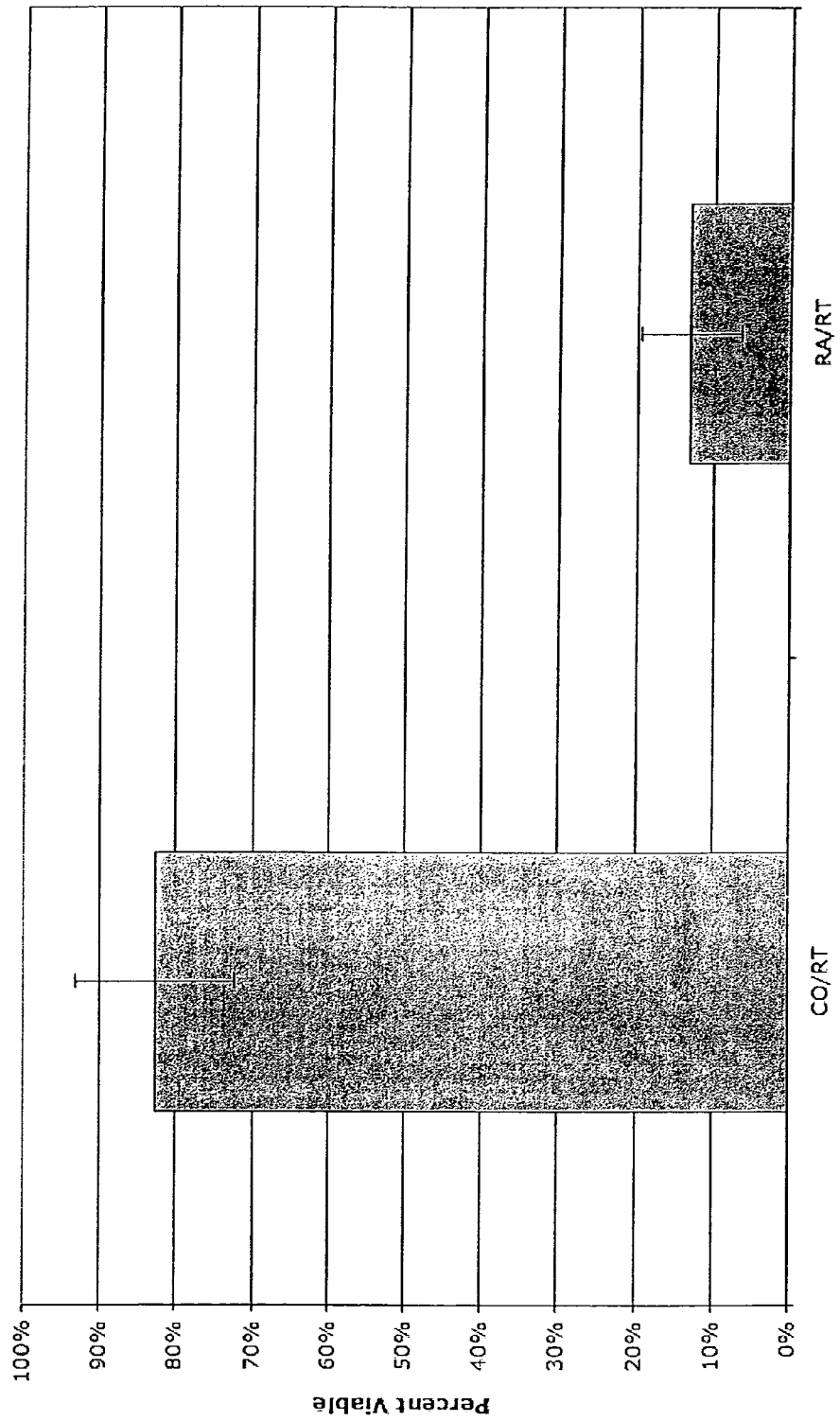
FIG. 1-Human keratinocytes survive exposure to 100% CO. Cells were inspected visually using an inverted phase contrast microscope. Quantitation of the number of viable keratinocytes as judged by trypan blue staining, which is an indicator of cell death.

In "stasis" or "suspended animation," a cell, tissue or organ, or organism (collectively referred to as "biological material") is living, but cellular functions necessary for cell division, developmental progression, metabolic state are slowed or even stopped. This state is desirable in a number of contexts. Stasis can be used as a method of preservation by itself, or it may be induced as part of a cryopreservation regimen. Biological materials may be preserved for research use, for transportation, for transplantation, for therapeutic treatment (such as ex vivo therapy), and to prevent the onset of trauma, for example. Stasis with respect to entire organisms have similar uses. For instance, transportation of organisms could be facilitated if they had entered stasis. This might reduce physical and physiological damage to the organism by reducing or eliminating stress or physical injury. These embodiments are discussed in further detail below. Stasis may be beneficial by decreasing the need of the biological material for oxygen and, therefore, bloodflow. It may extend the period of time that biological material can be isolated from a life-sustaining environment and exposed to a death-inducing environment.

The present invention is based on the observation that certain types of compounds effectively induce reversible stasis in biological matter.

A. Thermoregulation

Stasis in a warm-blooded animal will affect thermoregulation. Thermoregulation is a characteristic of so-called "warm-blooded" animals, which permits the organism to maintain a relatively constant core body temperature even when exposed to significantly altered (cold or hot) environmental temperatures. The ability to control thermoregulation by induction of stasis is one aspect of the invention, and permits uses similar to those discussed above.

Thermal regulation may be a facilitated by placing of organisms, limbs or isolated organs or tissues into chambers/devices, the temperature of which can be controlled. For example, warm rooms or chamber-like devices similar to hyperbaric chambers may encompass an entire organism and be connected to thermo-regulatory apparatus. Smaller devices such as blankets, sleeves, cuffs or gloves (e.g., CORE CONTROL cooling system by AVAcore Technologies, Palo Alto, Calif., U.S. Pat. No. 6,602,277) are also contemplated. Such chambers/devices may be used both to increase or reduce ambient temperatures.

B. Biological Matter

Biological material contemplated for use with the present invention include material derived from invertebrates and vertebrates, including mammals; biological materials includes organisms. In addition to humans, the invention can be employed with respect to mammals of veterinary or agricultural importance including those from the following classes: canine, feline, equine, bovine, ovine, murine, porcine, caprine, rodent, lagomorph, lupine, and ursine. The invention also extends to fish and birds. Other examples are disclosed below.

Moreover, the type of biological matter varies. It can be cells, tissues and organs, as well as organisms for which different compositions, methods, and apparatuses have relevance. The nonprovisional U.S. patent applications entitled "Methods, Compositions and Devices for Inducing Stasis in Cells" and "Methods, Compositions and Devices for Inducing Stasis in Cells, Tissues, Organs, and Organisms" in the name of Mark. B. Roth filed on Oct. 22, 2004 are hereby incorporated by reference in their entireties.

1. Different Sources

The following are examples of sources from which biological matter may be obtained. Embodiments of the invention include, but are not limited to, these examples.

a. Mammals

In certain aspects of the invention, the mammal is of the Order Monotremata, Marsupialia, Insectivora, Macroscelidia, Dermoptera, Chiroptera, Scandentia, Primates, Xenarthra, Pholidota, Tubulidentata, Lagomorpha, Rodentia, Cetacea, Carnivora, Proboscidea, Hyracoidea, Sirenia, Perissodactyla, or Artiodactyla.

Examples of Monotremata include the Families Tachyglossidae (e.g., Echidnas) and Omithorhynchidae (e.g., Platypus). Examples of Marsupialia include the Families Didelphidae (e.g., Opossums), Microbiotheriidae (e.g., Monito del Monte), Caenolestidae (e.g., Rat Oppossums), Dasyuridae (e.g., Marsupial mice), Myrmecobiidae (e.g., Numbat), Thylacinidae (e.g., Thylacine), Peramelidae (e.g., Bandicoots), Thylacomyidae (e.g., Rabbit Bandicoots), Notoryctidae (e.g., Marsupial Moles), Phalangeridae (e.g., Cuscuses), Petauridae (e.g., Ringtails, Gliders), Burramyidae (e.g., Pygmy Possums), Macropodidae (e.g., Kangaroos, Wallabies), Tarsipedidae (e.g., Honey Possum), Vombatidae (e.g., Wombats), and Phascolarctidae (e.g., Koalas).

Insectivora includes, for example, the Families Solenodontidae (e.g., Solenodons), Tenrecidae (e.g., Tenrecs, Otter-Shrews), Chrysochloridae (e.g., Golden Moles), Erinaceidae (e.g., Hedgehogs, Moonrats), Soricidae (e.g., Shrews), and Talpidae (e.g., Moles, Desmans). The Order Macroscelidia includes the Family Macroscelidia (e.g., Elephant Shrews). The Order Scandentia includes Tupaiidae (e.g., Tree Shrews). The Order Dermoptera includes the Family Cynocephalidea (e.g., Flying Lemurs). Chiroptera includes the Families Pteropodidae (e.g., Fruit Bats, Flying Foxes), Rhinopomatidae (e.g., Mouse-Tailed Bats), Craseonycteridae (e.g., Hog-Nosed or Bumblebee Bat), Emballonuridae (e.g., Sheath-Tailed Bats), Nycteridae (e.g., Slit-Faced Bats), Megadermatidae (e.g., False Vampire Bats), Rhinolophidae (e.g., Horshoe Bats), Noctilionidae (e.g., Bulldog Bats, Fisherman Bats), Mormoopidae, Phyllostomidae (e.g., New World Leaf-Nosed Bats), Natalidae, Furipteridae, Thyropteridae, Myzapodidae, Vespertilionidae (e.g., Common Bats), Mystacinidae (e.g., Short-Tailed Bats), and Molossjdae (e.g., Free-Tailed Bats).

The Order Primates includes the Families Lemuridae (e.g., Lemurs), Cheirogaleidae (e.g., Mouse Lemurs), Indriidae (e.g., *Indri*, Woolly Lemur), Daubentoniidae (e.g., Aye-Aye), Lorisidae (e.g., Lorises, Bushbabies, Galagos), Tarsiidae (e.g., Tarsiers), Cebidae (e.g., New World Monkeys, Marmosets, Tamarins), Hylobatidae (e.g., Gibbons), Pongidae (e.g., Apes), and Hominidae (e.g., Man).

Examples of Xenarthra include Myrmecophagidae (e.g., Anteaters), Bradypodidae (e.g., Three-Toed Sloths), Megalonychidae (e.g., Two-Toed Sloths), and Dasypodidae (e.g., Armadillos). Examples of Pholidota include Manidae (e.g., Pangolins). Examples of Tubulidentata include Orycteropodidae (e.g., Aardvarks). Examples of Lagomorpha include Ochotonidae (e.g., Pikas) and Leporidae (e.g., Hares and Rabbits).

The Order Rodentia includes the Families Aplodontidae (e.g., Mountain Beavers), Sciuridae (e.g., Squirrels, Marmots, Chipmunks), Geomyidae (e.g., Pocket Gophers), Heteromyidae (e.g., Pocket Mice, Kangaroo Rats), Castoridae (e.g., Beaver), Anomaluridae (e.g., Scaly-Tailed Squirrels), Pedetidae (e.g., Springhare), Muridae (e.g., Rats and Mice), Gliridae (e.g., Dormice), Seleviniidae (e.g., Desert Dormouse), Zapodidae (e.g., Jumping Mice), Dipodidae (e.g., Jerboas), Hystricidae (e.g., Old World Porcupines), Erethizontidae (e.g., New World Porcupines), Caviidae (e.g., Guinea Pigs, Maras), Hydrochaeridae (e.g., Capybara), Dinomyidae (e.g., Pacarana), Agoutidae (e.g., Pacas), Dasyproctidae (e.g., Agoutis), Chinchillidae (e.g., Chinchillas, Viscachas), Capromyidae (e.g., Hutias), Myocastoridae (e.g., Nutria), Ctenomyidae (e.g., Tuco-Tucos), Octodontidae (e.g., Octodonts, Degus), Abrocomidae (e.g., Chichilla Rats), Echimyidae (e.g., Spiny Rats), Thryonomyidae (e.g., Cane Rats), Petromyidae (e.g., African Rock Rat), Bathyergidae (e.g., Mole Rat), and Ctenodactylidae (e.g., Gundis).

The Order Cetacea includes the Families Iniidae (e.g., Amazon Popoise), Lipotidae, Platanistidae, Pontoporiidae, Ziphiidae (e.g., Beaked Whales), Physeteridae (e.g., Sperm Whales), Monodontidae (e.g., Beluga Whale, Narwhal), Delphinidae (e.g., Marine Dolphins, Killer Whales), Phocoenidae (e.g., Porpoises), Balaenopteridae (e.g., Rorquals), Balaenidae (e.g., Right Whales), and Eschrichtiidae (e.g., Gray Whales).

The Order Carnivora includes the Families Canidae (e.g., Dogs, Foxes, Wolves, Jackals, Coyotes), Ursidae (e.g., Bears), Procyonidae (e.g., Raccoons, Coatis, Kinkajous, Lesser Pandas), Ailuropodidae (e.g., Giant Pandas), Mustelidae (e.g., Weasels, Skunks, Badgers, Otters), Viverridae (e.g., Civets, Genets), Herpestidae (e.g., Mongooses), Protelidae (e.g., Aardwolf), Hyaenidae (e.g., Hyenas), Felidae (e.g., Cats), Otariidae (e.g., Eared Seals, Sea Lions), Odobenidae (e.g., Walrus), and Phocidae (e.g., Earless Seals).

The Order Proboscidea includes the Family Elephantidae (e.g., Elephants). Hyracoidea includes the Family Procaviidae (e.g., Hyraxes). Sirenia includes the Families Dugongidae (e.g., Dugong) and Trichechidaei (e.g., Manatees). The Order Perissodactyla includes the Families Equidae (e.g., Horses, Asses, Zebras), Tapiridae (e.g., Tapirs), and Rhinocerotidae (e.g., Rhinoceroses). The Order Artiodactyla includes the Families Suidae (e.g., Pigs, Babirusa), Tayassuidae (e.g., Peccaries), Hippopotamidae (e.g., Hippopotamuses), Camelidae (e.g., Camels, Llamas, Vicunas), Tragulidae (e.g., Chevrotains), Moschidae (e.g., Musk Deer), Cervidae (e.g., Deer, Elk, Moose), Giraffidae (e.g., Giraffe, Okapi), Antilocapridae (e.g., Pronghorn), and Bovidae (e.g., Cattle, Sheep, Antelope, Goats).

b. Reptiles

In certain embodiments, the biological material is a reptile or is derived from a reptile. The reptile may be of the Order Chelonia, Pleurodira, Squamata, Rhynchocephalia, or Crocodylia. A reptile of the Order Chelonia may be, for example, a Carettochelyidae, Chelydridae (e.g., Snapping Turtles), Cheloniidae (e.g., Loggerhead Turtles, Green Turtles), Dernatemydidae (e.g., Leatherback Turtles), Emydidae (e.g., Paitned Turtles, Pond Sliders, Pond Turtles, Snail-Eating Turtles, Box Turtles), Kinostemidae (e.g., Stinkpot Turtles), Saurotypidae, Testudinidae (e.g., Galapagos Tortoises, Desert Tortoises, Aldabra Turtles, Spu-Thighed Tortoises, Hermann's Tortoise), Trionychidae (e.g., Chinese Softshells, Spiny Softshells), or a Platysternidae. A reptile of the Order Pleurodira may be, for example, a Chelidae (e.g., Snake-Necked Turtles) or Pelomedusidae (e.g., Helmeted Turtles).

A reptile of the Order Squamata may be, for example, an Agamidae (e.g., Rainbow Lizards, Bearded Dragons, Indian Bloodsuckers, Spiny-Tailed Lizards), Chamaeleontdidae (e.g., Chameleons), Iguanidae (e.g., Anoles, Basilisks, Collared Lizards, Iguanas, Homed Lizards, Chuckwallas, Sagebrush Lizards, Side-Blotched Lizards), Gekkonidae (e.g., Geckos), Pygopodidae, Teiidae (e.g., Race Runners, Tegus), Lacertidae (e.g., Sand Lizards, Ocellated Lizards, Viviparous Lizards, Wall Lizards, Long-Tailed Lizards), Xantuslidae, Scincidae (e.g., Skinks), Cordylidae (e.g., Sungazers), Dibamidae, Xenosauridae, Anguidae (e.g., Slow Worm, Alligator Lizards, Sheltopusik, Glass Lizards), Helodermatidae (e.g., Gila Monster), Lanthanotidae, Varanidae (e.g., Monitors), Leptotyphlopidae, Typhlopidae, Anomalepididae, Aniliidae (e.g., Pipe Snakes), Uropeitidae, Xenopeltidae, Boidae (e.g., Boas, Anacondas, Rock Pythons), Acrochordidae (e.g., Wart Snakes), Colubridae (e.g., Mangrove Snakes, Whip Snakes, Smooth Snakes, Egg-Eating Snakes, Boomslangs, Rat Snakes, Aesculapian Snakes, Four-Lined Snakes, Oriental Beauty Snake, Tentacled Snakes, Hognose Snakes, Kingsnakes, Montpelier Snakes, Grass Snakes, Water Snakes, Garter Snakes, Twig Snakes, Keelback Snakes), Elapidae (e.g., Death Adders, Kraits, Mambas, Coral Snakes, Cobras, Copperhead, Puff Adder), Viperidae (e.g., Vipers, Right Adders, Rattlesnakes, Massasaugas, Adder), Hydrophiidae (e.g., Sea Brait), Amphisbaenidae (e.g., Worm Lizard), Bipedidae, or a Trogonophidae (e.g., Burrowing Lizard).

A reptile of the Order Rhynchocephalia may be, for example, a Sphenodontidae (e.g., Tuataras). A reptile of the Order Crocodylia may be, for example, an Alligatoridae (e.g., Alligators, Caiman), Crocodylidae (e.g., Crocodiles), or a Gavialidae (e.g., Gharials).

c. Amphibians

The biological material of the present invention may be an amphibian or may be derived from an amphibian. The amphibian may be, for example, a frog or a toad. The frog or toad may be, for example, an Arthroleptidae (e.g., screeching frogs), Ascaphidae (e.g., tailed frogs), Brachycephalidae (e.g., gold frogs and shield toads), Bufonidae (e.g., true toads), Centrolenidae (e.g., glass frogs and leaf frogs), Dendrobatidae (e.g., poison-dart frogs), Discoglossidae (e.g., fire-bellied toads), Heleophrynidae (e.g., ghost frogs), Hemisotidae (e.g., shovel-nosed frogs), Hylidae (e.g., New World tree frogs), Hyperoliidae (e.g., African tree frogs), Leiopelmatidae (e.g., New Zealand frogs), Leptodactylidae (e.g., neotropical frogs), Megophryidae (e.g., South Asian frogs), Microhylidae (e.g., microhylid frogs), Myobatrachidae (e.g., Australian frogs), Pelobatidae (e.g., spadefoot toads), Pelodytidae (e.g., parsley frogs), Pipidae (e.g., tongueless frogs), Pseudidae (e.g., paradox frogs), Ranidae (e.g., riparian frogs and true frogs), Rhacophoridae (e.g., Old World tree frogs), Rhinodermatidae (e.g., Darwin's frogs), Rhinophrynidae (e.g., burrowing toad), Sooglossidae (e.g., Seychelle frogs), Caudata (e.g., salamanders), or a Gymnophiona (e.g., caecilians).

The amphibian may be a salamander. The salamander may be, for example, an Ambystomatidae (e.g., mole salamanders), Amphiumidae (e.g., amphiumas), Cryptobranchidae (e.g., giant salamanders and hellbenders), Dicamptodontidae (e.g., Pacific giant salamanders), Hynobiidae (e.g., Asiatic salamanders), Plethodontidae (e.g., lungless salamanders), Proteidae (e.g., mudpuppies and waterdogs), Rhyacotritonidae (e.g., torrent salamanders), Salamandridae (e.g., newts and salamanders), or a Sirenidae (e.g., sirens). Alternatively, the amphibian may be a Caecilian. The Caecilian may be, for example, a Caeciliidae (e.g., caecilians), Ichthyophiidae (e.g., Asiatic tailed caecilians), Rhinatrematidae (e.g., neotropical tailed caecilians), Scolecomorphidae (e.g., African caecilians), Typhlonectidae (e.g., aquatic caecilians), or an Uraeotyphlidae (e.g., Indian caecilians).

d. Birds

The biological material of the present invention may be a bird or may be derived from a bird. The bird may be, for example, an Anseriforme (e.g., waterfowl), Apodiforme (e.g., hummingbirds and swifts), Caprimulgiforme (e.g., nightbirds), Charadriiforme (e.g., shorebirds), Ciconiiforme (e.g., storks), Coliiforme (e.g., mousebirds), Columbiforme (e.g., doves and pigeons), Coraciiforme (e.g., kingfishers), Craciforme (e.g., chacalacas, currasows, guans, megapodes), Cuculiforme (e.g., cuckoos, hoatzin, turacos), Falconiforme (e.g., diurnal birds of prey), Galliforme (e.g., chicken-like birds), Gaviiforme (e.g., loons), Gruiforme (e.g., coots, cranes, rails), Passeriforme (e.g., perching birds), Pelecaniforme (e.g., pelicans), Phoenicopteriforme (e.g., flamingos), Piciforme (e.g., woodpeckers), Podicipediforme (e.g., grebes), Procellariiforme (e.g., tube-nosed seabirds), Psittaciforme (e.g., parrots), Sphenisciforme (e.g., penguins), Strigiforme (e.g., owls), Struthioniforme (e.g., cassowaires, emus, kiwis, ostriches, rheas), Tinamiforme (e.g., tinamous), Trogoniforme (e.g., trogons), or a Turniciforme (e.g., buttonquail).

e. Fish

The biological material of the present invention may be a fish or may be derived from a fish. The fish may be, for example, an Acipenseriforme (e.g., paddlefishes, spoonfishes, and sturgeons), Polypteriforme (e.g., bichirs, birchers, lobed-finned pike, and reed fishes), Atheriniforme (e.g., rainbow fishes and silversides), Beloniforme (e.g., halfbeeks and needlefishes), Beryciforme, Channiforme, Cyprinodontiforme (e.g., killifishes), Dactylopteriforme (e.g., flying gurnards), Gasterosteiforme (e.g., pipefishes and sticklebacks), Mugiliforme (e.g., mullets), Pegasiforme (e.g., dragonfishes and sea moths), Perciforme (e.g., perch-like fishes), Pleuronectiforme (e.g., flatfishes, flounders, and soles), Scorpaeniforme (e.g., scorpion fishes and sculpins), Stephanoberyciforme, Synbranchiforme (e.g., swamp eels), Tetraodontiforme (e.g., cowfishes, filefishes, leatherjackets, puffers, triggerfishes, and trunkfishes), Zeiforme (e.g., boarfishes, dories, and john dories), Atherinomorpha, Clupeiforme (e.g., anchovies and herrings), Aulopiforme, Albuliforme, Anguilliforme (e.g., eels), Elopiforme (e.g., tarpons), Notacanthiformes (e.g., spiny eels and tapirfishes), Saccopharyngiformes, Lampridiforme (e.g., opahs and ribbonfishes), Characiforme (e.g., leporins and piranhas), Cypriniforme (e.g., minnows, suckers, zebra fish), Gonorhynchiforme (e.g., milkfish and shellears), Gymnotiforme, Siluriforme (e.g., catfishes), Aphredoderiforme (e.g., cavefishes and pirate perches), Batrachoidiforme, Gadiforme (e.g., cods and hakes), Gobiesociforme, Lophiiforme (e.g., anglerfishes), Ophidiiforme, Percopsiforme (e.g., troutperches), Polymixiiforme (e.g., beardfishes), Cetomimiforme, Ctenothrissiforme, Esociforme (e.g., mudminnows and pikes), Osmeriforme (e.g., Argentines and smelts), Salmoniforme (e.g., salmons), Myctophiforme (e.g., Latern Fishes), Ateleopodiforme, Stomiiforme, Amiiforme (e.g., bowfins), Semionotiforme (e.g., gars), Syngnathiforme (e.g., pipefishes and seahorses), Ceratodontiforme (e.g., Australian lungfishes), Lepidosireniforme (e.g., South American lungfishes and African lungfishes), or a Coelacanthiforme (e.g., coelacanths).

f. Invertebrates

The biological material maybe an invertebrate or derived from an invertebrate. The invertebrate may be, for example, a Porifera (e.g., sponges), Cnidaria (e.g., jellyfish, hydras, sea anemones, Portuguese man-of-wars, and corals), Platyhelminthe (e.g., flatworms, including planaria, flukes, and tapeworms), Nematoda (e.g., roundworms, including rotifers and nematodes), Mollusca (e.g., mollusks, snails, slugs, octopuses, squids), Annelida (e.g., segmented worms, including earthworms, leeches, and marine worms), Echinodermata (e.g., sea stars, sea cucumbers, sand dollars, sea urchins), Phoronida (e.g., Horseshoe Worms), Tardigrada (e.g., Water Bears), Acanthocephala (e.g., Spiny Headed Worms), Ctenophora (e.g., Comb Jellies), or an Arthropod (e.g., arachnids, crustaceans, millipedes, centipedes, insects).

An Arthropod may be, for example, a Coleoptera (e.g., beetles), Diptera (e.g., true flies), Hymenoptera (e.g., ants, bees, wasps), Lepidoptera (e.g., butterflies, moths), Mecoptera (e.g., scorpion flies), Megaloptera, Neuroptera (e.g., lacewings and relatives), Siphonaptera (e.g., fleas), Strepsiptera (e.g., parasitic insects and twisted-winged parasites), Trichoptera (e.g., caddisflies), Anoplura (e.g., sucking lice), Hemiptera (e.g., true bugs and their relatives), Mallophaga (e.g., biting lice), Psocoptera (e.g., psocids), Thysanoptera (e.g., thrips), Orthoptera (e.g., grasshoppers, locusts), Dermaptera (e.g., earwigs), Dictyoptera, Embioptera (e.g., webspinners), Grylloblattodea, Mantophasmatodea (e.g., gladiators), Plecoptera (e.g., stoneflies), Zoraptera (e.g., zorapterans), Ephemeroptera (e.g., mayflies), Odonata (e.g., dragonflies and damselflies), Phasmatoptera (e.g., walkingsticks), Thysanura (e.g., bristletails), Archaeognatha, Collembola (e.g., snow flies and springtails), Chilopoda (e.g., centipedes), Diplopoda (e.g., millipedes), Pauropoda (e.g., pauropods, pauropodans, and progoneates), Symphyla (e.g., pseudocentipedes and symphylans), Malacostraca (e.g., crabs, krill, pill bugs, shrimp), Maxillopoda, Branchiopoda (e.g., branchiopods), Cephalocarida, Ostracoda (e.g., ostracods), Remipedia, Branchiura, Cirripedia (e.g., barnacles), Arachnida (e.g., arachnids, including amblypygids, spiders, daddy longlegs, harvestmen, microscorpions, book scorpions, false scorpions, pseudoscorpions, scorpions, solpugids, sun spiders, and uropygids), Merostomata (e.g., horseshoe crabs), or a Pycnogonida (e.g., sea spiders).

g. Fungi

The biological material of the present invention may be a fungi or may be derived from a fungi. The fungi may be, for example, an Ascomycota (sac fungi), Basidiomycota (club fungi), Chytridiomycota (chytrids), Deuteromycota, or a Zygomycota. The fungi may be a *Rhizopus, Pilobolus, Arthrobotrys, Aspergillus, Allomyces, Chytridium, Agaricus, Amanita, Cortinarius, Neurospora, Morchella, Saccharomyces, Pichia, Candida, Schizosaccharomyces,* or *Ergot*. In particular embodiments the fungi may be *Saccharomyces cerevisiae, Schizosaccharomyces pombe, Candida albicans,* or *Pichia pastoris*.

h. Plants

The biological material of the present invention may be a plant or may be derived from a plant. The plant may be a Bryophyte (e.g., mosses, liverworts, hornworts), Lycophyte (e.g., club mosses, ground pine), Sphenophyte (e.g., horsetails), Pterophyte (e.g., ferns), Cycadophyte (e.g., cycads), Gnetophyte (e.g., gnetum, ephedra, welwitschia), Coniferophyte (e.g., conifers), Ginkophyte (e.g., ginko), or Anthophyte (e.g., flowering plants). The Anthophyte may be a monocot or a dicot. Non-limiting examples of monocotyledonous plants include wheat, maize, rye, rice, turfgrass, sorghum, millet, sugarcane, lily, iris, agave, aloe, orchids, bromeliads, and palms. Non-limiting examples of dicotyledonous plants include tobacco, tomato, potato, soybean, sunflower, alfalfa, canola, rose, *Arabidopsis*, coffee, citrus fruits, beans, alfalfa, and cotton.

i. Protists

The biological material of the present invention may be a Protist or may be derived from a Protist. The Protist may be a Rhodophyte (e.g., red algae), Phaeophyte (e.g., brown algae, kelp), Chlorophyte (e.g., green algae), Euglenophyte (e.g., euglenoids) Myxomycot (e.g., slime molds), Oomycot (e.g., water molds, downy mildews, potato blight), or Bacillariophyte (e.g., diatoms).

j. Prokaryotes

In certain aspects of the invention, the biological material is a prokaryote or is derived from a prokaryote. In certain embodiments the prokaryote is an Archaea (*archaebacteria*). The *archaebacteria* may be, for example, a Crenarchaeota, Euryarchaeota, Korarchaeota or Nanoarchaeota. In certain aspects the Euryarchaeota is a *Halobacteria, Methanobacteria, Methanococci, Methanomicrobia, Methanosarcinae, Methanopyri, Archeoglobi, Thermoplasmata,* or a *Thermococci*. Specific, non-limiting examples of *archaebacteria* include: *Aeropyrum pernix, Methanococcus jannaschii, Halobacterium marismortui,* and *Thermoplasma acidophilum*.

In certain embodiments the prokaryote is an Eubacteria. The Eubacteria may be, for example, an Actinobacteria, Aquificae, Bacteroidetes, Green sulfur bacteria, Chlamydiae, Verrucomicrobia, Chloroflexi, Chrysiogenetes, Cyanobacteria, Deferribacteres, Deinococcus-Thermus, Dictyoglomi, Fibrobacteres/Acidobacteria, Firmicutes, Fusobacteria, Gemmatimonadetes, Nitrospirae, Omnibacteria, Planctomycetes, Proteobacteria, Spirochaetes, Thermodesulfobacteria, or Thermotogae. Non-limiting examples of Actinobacteria include bacteria of the genera *Actinomyces, Arthrobacter, Corynebacterium, Frankia, Micrococcus, Micromonospora, Mycobacterium, Propionibacterium,* and *Streptomyces*. Specific examples of Actinobacteria include *Mycobacterium leprae, Mycobacterium tuberculosis, Mycobacterium avium, Corynebacterium glutamicum, Propionibacterium acnes,* and *Rhodococcus equi*.

Non-limiting examples of Aquificae include bacteria of the genera *Aquifex, Hydrogenivirga, Hydrogenobacter, Hydrogenobaculum, Thermocrinis, Hydrogenothermus, Persephonella, Sulfurihydrogenibium, Balnearium, Desulfurobacterium,* and *Thermovibrio*. Non-limiting examples of Firmicutes include bacteria of the genera *Bacilli, Clostridia,* and *Molecutes*. Specific examples of Firmicutes include: *Listeria innocua, Listeria monocytogenes, Bacillus subtilis, Bacillus anthracis, Bacillus thuringiensis, Staphylococcus aureus, Clostridium acetobutylicum, Clostridium difficile, Clostridium perfringens, Mycoplasma genitalium, Mycoplasma pneumoniae, Mycoplasma pulmonis, Streptococcus pneumoniae, Streptococcus pyogenes, Streptococcus mutans, Lactococcus lactis,* and *Enterococcus faecalis*.

Non-limiting examples of Chlamydiae/Verrucomicrobia include bacteria such as *Chlamydia trachomatis, Chlamydia pneumoniae,* I *Chlamydia psittaci*. Non-limiting examples of Deinococcus-Thermus include bacteria of the genera *Deinococcus* and *Thermus*.

Proteobacteria are gram-negative bacteria. Non-limiting examples of Proteobacteria include bacteria of the genera *Escherichia, Salmonella, Vibrio, Rickettsia, Agrobacterium, Brucella, Rhizobium, Neisseria, Bordetella, Burkholderi, Buchnera, Yersinia, Klebsiella, Proteus, Shigella, Haemophilus, Pasteurella, Actinobacillus, Legionella, Mannheimia, Coxiella, Aeromonas, Francisella, Moraxella, Pseudomonas, Campylobacter,* and *Helicobacter*. Specific examples of Proteobacteria include: *Rickettsia conorii, Rickettsia prowazekii, Rickettsia typhi, Ehrlichia bovis, Agrobacterium tumefaciens, Brucella melitensis, Rhizobium rhizogenes, Neisseria meningitides, Bordetella parapertussis, Bordetella pertussis, Burkholderi mallei, Burkholderi pseudomallei, Neisseria gonorrhoeae, Escherichia coli, Salmonella enterica, Salmonella typhimurium, Yersinia pestis, Klebsiella pneumoniae, Yersinia enterocolitica, Proteus vulgaris, Shigella flexneri, Shigella sonnei, Shigella dysenterica, Haemophilus influenzae, Pasteurella multocida, Actinobacillus actinomycetemcomitans, Actinobacillus pleuropneumoniae, Haemophilus somnus, Legionella pneumophila, Mannheimia haemolytica, Vibrio cholerae, Vibrio parahaemolyticus, Coxiella burnetii, Aeromonas hydrophila, Aeromonas salmonicida, Francisella tularesis, Moraxella catarrhalis, Pseudomonas aeruginosa, Pseudomonas putida, Campylobacter jejuni,* and *Helicobacter pylori*.

Non-limiting examples of Spirochaetes include bacteria of the families Brachyspiraceae, Leptospiraceae, and Spirochaetaceae. Specific examples of Spirochaetes include *Borrelia burgdorferi*, and *Treponema pallidum*.

2. Different Types of Biological Matter

Tissues contemplated for use in methods and apparatuses of the invention are limited only insofar as they have cells that utilize oxygen to produce energy (and thus, are alive).

Tissue can be from a particular part of the body or organ, such as one from the group consisting of: heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, the tissue can contain one or more of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

Moreover, stasis can be induced in plants or parts of plants, including fruit, flowers, leaves, stems, seeds, cuttings. Plants can be agricultural, medicinal, or decorative. Induction of stasis in plants may enhance the shelf life or pathogen resistance of the whole or part of the plant.

Methods and apparatuses of the invention can be used to induce stasis in tissue. This can serve to protect and/or preserve them or to prevent damage or injury to them. Tissue can be better preserved for research purposes or for transplantation/implantation purposes. For example, organs can be preserved longer, survive preservation better, and/or endure less injury or damage during the preservation process or as a result of the preservation process.

The amount of time that organs for transplant can be preserved varies, with heart and lung being the most time sensitive. Generally, the maximum amounts of time (maximum cold ischemic time) that organs are currently preserved is as follows:

| | |
|---|---|
| Heart and lungs | 4-6 hours |
| Liver | 12-24 hours |
| Pancreas | 12-24 hours |
| Small Intestine | 12 hours |

Thus, the present invention can be used to extend these times up to 48 hours by keeping them in stasis for that long.

3. Assays

Stasis can be measured by a number of ways, including by quantifying the amount of oxygen consumed by a biological sample, the amount of carbon dioxide produced by the sample (indirect measurement of cellular respiration), or characterizing motility.

To determine the rate of consumption of oxygen or the rate of production of carbon dioxide the biological matter is placed into a chamber that is sealed with two openings; for gas import and export. Gas (room air or other gases) is passed into the chamber at a given flow rate and out of the exit port to maintain approximately 1 atmosphere of pressure in the chamber. Before and after exposure to the chamber the gas is passed through a carbon dioxide detector and or an oxygen detector to measure (every second) the amount of each compound in the gas mixture. Comparison of these values over time gives the rate of oxygen consumption or carbon dioxide production.

II. Oxygen Antagonists

Oxygen metabolism is a fundamental requirement for life in aerobic metazoans. Aerobic respiration accounts for the vast majority of energy production in most animals and also serves to maintain the redox potential necessary to carry out important cellular reactions. In hypoxia, decreased oxygen availability results in inefficient transfer of electrons to molecular oxygen in the final step of the electron transport chain. This inefficiency results in both a decrease in aerobic energy production and an increase in the production of damaging free radicals, mainly due to the premature release of electrons at complex III and the formation of $O_2^-$ by cytochrome oxidase (Semenza, 1999). Limited energy supplies and free radical damage can interfere with essential cellular processes such as protein synthesis and maintenance of membrane polarities (Hochachka et al., 1996), and will ultimately lead to cell death.

A. Carbon Monoxide

Carbon monoxide (CO) is a colorless, odorless, and tasteless gas that can be toxic to animals, including humans. According to the Center for Disease Control, more than 450 people unintentionally die from carbon monoxide each year.

It can be toxic to organisms whose blood carries oxygen to sustain its survival. It may be poisonous by entering the lungs through normal breathing and displacing oxygen from the bloodstream. Interruption of the normal supply of oxygen jeopardizes the functions of the heart, brain and other vital functions of the body.

At amounts of 50 parts per million (ppm), carbon monoxide presents no symptoms to humans exposed to it. However, at 200 ppm, within two-three hours the carbon monoxide can cause a slight headache; at 400 ppm, within one to two hours it can cause a frontal headache that may become widespread within three hours; and, at 800 ppm it can cause dizziness, nausea, and/or convulsions within 45 minutes, and render the subject insensible within two hours. At levels of around 1000 ppm, an organism can expire after exposure for more than around 1-2 minutes.

Because of the well-known and well-documented toxic effects of carbon monoxide to an organism, it is thus surprising and unexpected that carbon monoxide can be used to induce stasis of and/or help preserve live biological samples. It is thus contemplated that carbon monoxide can be used for inducing stasis in isolated biological matter, such as blood-free biological matter (because of the effects that carbon monoxide has with respect to hemoglobin, which is a separate pathway than the one involved in inducing stasis).

In addition to exposure to carbon monoxide either to induce stasis or to limit or prevent any damage caused by a stasis-inducing agent, the invention contemplates that carbon monoxide may be used in combination with agents or methods that assist in the preservation and/or transplantation/grafting process of biological materials.

B. Chalcogenide Compounds

Compounds containing a chalcogen element; those in Group 6 of the periodic table, but excluding oxides, are commonly termed "chalcogenides" or "chalcogenide compounds" (used interchangeably herein). These elements are sulfur (S), selenium (Se), tellurium (Te) and polonium (Po). Common chalcogenides contain one or more of S, Se and Te, in addition to other elements. Chalcogenide compounds can be employed as reducing agents.

The present inventor, though not bound by the following theory, believes that the ability of chalcogenides to induce stasis in cells, and to permit modulation of core body temperature in animals, stems from the binding of these molecules to cytochrome oxidase. In so doing, chalcogenides inhibit or reduce the activity of oxidative phosphorylation. The ability of chalcogenides to block autonomous thermoregulation, i.e., to permit core body temperatures of "warm-blooded" animals to be manipulated through control of environmental temperatures, is believed to stem from the same mechanism as set forth above—binding to cytochrome oxidase, and blocking or reducing the activity of oxidative phosphorylation. Chalcogenides may be provided in liquid as well as gaseous forms.

Chalcogenides can be toxic, and at some levels lethal, to mammals. In accordance with the present invention, it is anticipated that the levels of chalcogenide should not exceed lethal levels in the appropriate environment. Lethal levels of chalcogenides may be found, for example in Material Safety Data Sheets for each chalcogenide or from information sheets available from the Occupational Safety and Health Administration (OSHA) of the US Government.

While carbon monoxide and chalcogenide compounds can both induce stasis by acting as an oxygen antagonist, they have different toxic effects that are separate from their abilities to induce stasis. Moreover, the concentrations needed to mediate a stasis effect are different because of the different affinities of cytochrome oxidase. While the affinity of cytochrome oxidase for oxygen is about 1:1 as compared to carbon monoxide, the affinity for $H_2S$ appears on the order of about 300:1 as compared to oxygen. This impacts what toxic effects are observed with a stasis-inducing concentration. Thus, it is contemplated that chalcogenide compounds are particularly suited for inducing stasis of biological matter in whole organisms and of whole organisms.

It also may prove useful to provide additional stimuli to a biological matter before withdrawing the chalcogenide. In particular, it is envisioned that one may subject an animal to increased ambient temperature prior to removing the source of chalcogenide.

1. $H_2S$

Hydrogen sulfide ($H_2S$) is a potentially toxic gas that is often associated with petrochemical and natural gas, sewage, paper pulp, leather tanning, and food processing. The primary effect, at the cellular level, appears to be inhibition of cytochrome oxidase and other oxidative enzymes, resulting in cellular hypoxia. Exposure to extreme levels (500 ppm) results in sudden collapse and unconsciousness, a so-called "knockdown" effect, followed by recovery. Post-exposure effects may persist for years, and include loss of coordination, memory loss, motor dysfunction, personality changes, hallucination and insomia.

Most contact with $H_2S$, however, occurs well below such acute toxicity levels. Nonetheless, there is general concern over longterm contact at sub-acute levels. Some reports exist indicating persistent impairments in balance and memory, as well as altered sensory motor functions may occur in humans following chronic low-level $H_2S$ exposure. Kilburn and Warshaw (1995); Kilburn (1999). Others have reported that perinatal exposure of rats to low (20 or 50 ppm) $H_2S$ for 7 hours per day from gestation through post-natal day 21 resulted in longer dendritic branches with reduced aborization of cerebellar Purkinje cells. Other neurologic defects associated with relatively low levels of $H_2S$ include altered brain neurotransmitter concentrations and altered neurologic responses, such as increased hippocampal theta EEG activity.

Behavioral toxicity was studied in rats exposed to moderate levels of $H_2S$. The results showed that $H_2S$ inhibits discriminated avoidance responses immediately after the end of the exposure (Higuchi and Fukamachi, 1997), and also interferes with the ability of rats to learn a baited radial arm maze task (Partlo et al., 2001). In another perinatal study using 80 ppm $H_2S$, no neuropathological effects or altered motor activity, passive avoidance, or acoustic startle response in exposed rat pups was seen. Dorman et al. (2000). Finally, Struve et al. (2001) exposed rats to $H_2S$ by gas at various levels for 3 hours per day on five consecutive days. Significant reductions in motor activity, water maze performance and body temperature following exposure to 80 ppm or greater $H_2S$ were observed. Taken together, these reports indicate that $H_2S$ can have a variety of effects on the biochemistry of mammalian tissues, but there is no clear pattern of response in terms of behavior.

Typical levels of hydrogen sulfide contemplated for use in accordance with the present invention include values of about 1 to about 150 ppm, about 10 to about 140 ppm, about 20 to about 130 ppm, and about 40 to about 120 ppm, or the equivalent oral, intravenous or transdermal dosage thereof. Other relevant ranges include about 10 to about 80 ppm, about 20 to about 80 ppm, about 10 to about 70 ppm, about 20 to about 70 ppm, about 20 to about 60 ppm, and about 30 to about 60 ppm, or the equivalent oral, intravenous or transdermal thereof. It also is contemplated that, for a given animal in a given time period, the chalcogenide atmosphere should be reduced to avoid a potentially lethal build up of chalcogenide in the subject. For example, an initial environmental concentration of 80 ppm may be reduced after 30 min to 60 ppm, followed by further reductions at 1 hr (40 ppm) and 2 hrs (20 ppm).

2. $H_2Se$, $H_2Te$, and $H_2Po$,

Hydrogen selenide ($H_2Se$) is a key metabolite, formed from inorganic sodium selenite (oxidation state+4) via selenodiglutathione (GSSeSG), through reduction by thiols and NADPH-dependent reductases, and released from selenocysteine by lyase action (Ganther, 1999). Hydrogen selenide provides Se for synthesis of selenoproteins after activation to selenophosphate.

Hydrogen telluride ($H_2Te$) exists as an unstable gas.

3. Other Reducing Agents

In certain embodiments, the reducing agent structure compound is dimethylsulfoxide (DMSO), dimethylsulfide (DMS), methylmercaptan ($CH_3SH$), mercaptoethanol, thiocyanate, hydrogen cyanide, methanethiol (MeSH), or $CS_2$. In particular embodiments, the oxygen antagonist is $CS_2$, MeSH, or DMS. Compounds on the order of the size of these molecules are particularly contemplated (that is, within about 50% of their molecular weights).

Additional compounds that are envisioned as useful for inducing stasis include, but are not limited to, the following structures, many of which are readily available and known to those of skill in the art (identified by CAS number): 104376-79-6 (Ceftriaxone Sodium Salt); 105879-42-3; 1094-08-2 (Ethopropatine HCl); 1098-60-8 (Triflupromazine HCl); 111974-72-2; 113-59-7; 113-98-4 (Penicillin G K$^+$); 115-55-9; 1179-69-7; 118292-40-3; 119478-56-7; 120138-50-3; 121123-17-9; 121249-14-7; 1229-35-2; 1240-15-9; 1257-78-9 (Prochlorperazine Edisylate Salt); 128345-62-0; 130-61-0 (Thioridazine HCl) 132-98-9 (Penicillin V K$^+$); 13412-64-1 (Dicloxacillin Na$^+$ Hydrate); 134678-17-4; 144604-00-2; 146-54-3; 146-54-5 (Fluphenazine 2HCl); 151767-O$_2$-1; 159989-65-8; 16960-16-0 (Adrenocorticotropic Hormone Fragment 1-24); 1982-37-2; 21462-39-5 (Clindamycin HCl); 22189-31-7; 22202-75-1; 23288-49-5 (Probucol); 23325-78-2; 24356-60-3 (Cephapirin); 24729-96-2 (Clindarnycin); 25507-04-4; 26605-69-6; 27164-46-1 (Cefazolin Na$^+$); 2746-81-8; 29560-58-8; 2975-34-0; 32672-69-8 (Mesoridazine Benzene Sulfonate); 32887-01-7; 33286-22-5 (($^+$)-cis-Diltiazem HCl); 33564-30-6 (Cefoxitin Na$^+$); 346-18-9; 3485-14-1; 3511-16-8; 37091-65-9 (Azlocillin Na$^+$); 37661-08-8; 3819-00-9; 38821-53-3 (Cephradine); 41372-

O₂-5; 42540-40-9 (Cefamandole Nafate); 4330-99-8 (Trimeprazine hemi-(⁺)-tartrate Salt); 440-17-5 Trifluoperazine 2HCl; 4697-14-7 (Ticarcillin 2Na⁺); 4800-94-6 (Carbenicillin 2Na⁺); 50-52-2; 50-53-3; 5002-47-1; 51481-61-9 (Cimetidine); 52239-63-1 (6-propyl-2-thiouracil); 53-60-1 (Promazine HCl); 5321-32-4; 54965-21-8 (Albendazole); 5591-45-7 (Thiothixene); 56238-63-2 (Cefuroxime Na⁺); 56796-39-5 (Cefinetazole Na⁺); 5714-00-1; 58-33-3 (Promethazine HCl); 58-38-8; 58-39-9 (Perphenazine); 58-71-9 Cephalothin Na⁺); 59703-84-3 (Piperacillin Na⁺); 60-99-1 (Methotrimeprazine Maleate Salt); 60925-61-3; 61270-78-8; 6130-64-9 (Penicillin G Procaine Salt Hydrate); 61318-91-0 Sulconazole Nitrate Salt); 61336-70-7 Amoxicillin Trihydrate); 62893-20-3 Cefoperazone Na⁺); 64485-93-4 (Cefotaxime Na⁺); 64544-07-6; 64872-77-1; 64953-12-4 Moxalactam Na⁺); 66104-23-2 (Pergolide Mesylate Salt); 66309-69-1; 66357-59-3 (Ranitidine HCl); 66592-87-8 (Cefodroxil); 68401-82-1; 69-09-0 (Chlorpromazine HCl); 69-52-3 (Ampicillin Na⁺); 69-53-4 (Ampicillin); 69-57-8 Penicillin G Na⁺); 70059-30-2; 70356-03-5; 7081-40-5; 7081-44-9 (Cloxacillin Na⁺ H₂O); 7177-50-6 Nafcillin Na⁺ H₂O); 7179-49-9; 7240-38-2 (Oxacillin Na H₂O); 7246-14-2; 74356-00-6; 74431-23-5; 74849-93-7; 75738-58-8; 76824-35-6 (Famotidine); 76963-41-2; 79350-37-1; 81129-83-1; 84-02-6 (Prochlorperazine Dimaleate Salt); 87-08-1 (Phenoxymethylpenicillinic Acid); 87239-81-4; 91-33-8 (Benzthiazide); 91832-40-5; 94841-17-5; 99294-94-7; 154-42-7 (6-Thioguanine); 36735-22-5; 536-33-4 (Ethionamide); 52-67-5 (D-Penicillamine); 304-55-2 (Meso-2,3-Dimercaptosuccinic Acid); 59-52-9 2,3-Dimercapto⁺ propanol 6112-76-1 (6-mercaptopurine); 616-91-1 (N-acetyl-L-cysteine); 62571-86-2 (Captopril); 52-01-7 (spironolactone); and, 80474-14-2 (fluticasone propionate).

C. Other Antagonists

1. Hypoxia and Anoxia

Hypoxia is a common natural stress and several well conserved responses exist that facilitate cellular adaptation to hypoxic environments. To compensate for the decrease in the capacity for aerobic energy production in hypoxia, the cell must either increase anaerobic energy production or decrease energy demand (Hochachka et al., 1996). Examples of both of these responses are common in metazoans and the particular response used depends, in general, on the amount of oxygen available to the cell.

In mild hypoxia, oxidative phosphorylation is still partially active, so some aerobic energy production is possible. The cellular response to this situation, which is mediated in part by the hypoxia-inducible transcription factor, HIF-1, is to supplement the reduced aerobic energy production by upregulating genes involved in anaerobic energy production, such as glycolytic enzymes and glucose transporters (Semenza, 2001; Guillemin et al., 1997). This response also promotes the upregulation of antioxidants such as catylase and superoxide dismutase, which guard against free radical-induced damage. As a result, the cell is able to maintain near normoxic levels of activity in mild hypoxia.

In an extreme form of hypoxia, referred to as "anoxia"—defined here as <0.001 kPa O₂—oxidative phosphorylation ceases and thus the capacity to generate energy is drastically reduced. In order to survive in this environment, the cell must decrease energy demand by reducing cellular activity (Hochachka et al., 2001). For example, in turtle hepatocytes deprived of oxygen, a directed effort by the cell to limit activities such as protein synthesis, ion channel activity, and anabolic pathways results in a 94% reduction in demand for ATP (Hochachka et al., 1996). In zebrafish (Danio rerio) embryos, exposure to anoxia leads to a complete arrest of the heartbeat, movement, cell cycle progression, and developmental progression (Padilla et al., 2001). Similarly, *C. elegans* respond to anoxia by entering into suspended animation, in which all observable movement, including cell division and developmental progression, ceases (Padilla et al., 2002; Van Voorhies et al., 2000). *C. elegans* can remain suspended for 24 hours or more and, upon return to normoxia, will recover with high viability. This response allows *C. elegans* to survive the hypoxic stress by reducing the rate of energetically expensive processes and preventing the occurrence of damaging, irrevocable events such as aneuploidy (Padilla et al., 2002; Nystul et al., 2003).

One recently discovered response is the hypoxia-induced generation of carbon monoxide by heme oxygenase-1 (Dulak et al., 2003). Endogenously produced carbon monoxide can activate signaling cascades that mitigate hypoxic damage through anti-apoptotic (Brouard et al., 2003) and anti-inflammatory (Otterbein et al., 2000) activity, and similar cytoprotective effects can be achieved in transplant models by perfusion with exogenous carbon monoxide (Otterbein et al, 2003; Amersi et al., 2002). At higher concentrations, carbon monoxide competes with oxygen for binding to iron-containing proteins, such as mitochondrial cytochromes and hemoglobin (Gorman et al., 2003), though the cytoprotective effect that this activity may have in hypoxia has not been investigated.

Despite the existence of these sophisticated defense mechanisms against hypoxic damage, hypoxia is still often a damaging stress. For example, mammals have both heme oxygenase-1 and HIF-1, and some evidence suggests that suspended animation is possible in mammals as well (Bellamy et al., 1996; Alam et al., 2002). Yet, hypoxic damage due to trauma such as heart attack, stroke or blood loss is a major cause of death. The understanding of the limitations of the two fundamental strategies for surviving hypoxic stress, remaining animated or suspending animation, is hampered by the fact that it has been based on studies in a variety of systems under a variety of conditions.

"Hypoxia" occurs when the normal physiologic levels of oxygen are not supplied to a cell or tissue. "Normoxia" refers to normal physiologic levels of oxygen for the particular cell type, cell state or tissue in question. "Anoxia" is the absence of oxygen. "Hypoxic conditions" are those leading to cellular hypoxia. These conditions depend on cell type, and on the specific architecture or position of a cell within a tissue or organ, as well as the metabolic status of the cell. For purposes of the present invention, hypoxic conditions include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%; alternatively, these numbers could represent the percent of atmosphere at 1 atmosphere of pressure (101.3 kPa). An oxygen concentration of zero percent defines anoxic conditions. Thus, hypoxic conditions include anoxic conditions, although in some embodiments, hypoxic conditions of not less than 0.5% are implemented. As used herein, "normoxic conditions" constitute oxygen concentrations of around 20.8% or higher.

Standard methods of achieving hypoxia or anoxia are well established and include using environmental chambers that rely on chemical catalysts to remove oxygen from the chamber. Such chambers are available commercially from, for example, BD Diagnostic Systems (Sparks, Md.) as GASPAK Disposable Hydrogen+Carbon Dioxide Envelopes or BIO-BAG Environmental Chambers. Alternatively, oxygen may be depleted by exchanging the air in a chamber with a non-oxygen gas, such as nitrogen. Oxygen concentration may be determined, for example using a FYRITE Oxygen Analyzer (Bacharach, Pittsburgh Pa.).

III. Preservation Applications

Stasis can be induced in any cell, tissue, or organism as discussed above. This includes plants or parts of plants, including fruit, flowers, leaves, stems, seeds, cuttings. Plants can be agricultural, medicinal, or decorative. Induction of stasis in plants may enhance the shelf life or pathogen resistance of the whole or part of the plant.

In embodiments of the invention, an organism or part thereof can be exposed to an oxygen antagonist for about, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, 1, 2, 3, 4, 5, 6, 7, 8, 9, 10, 11, 12, 13, 14, 15, 16, 17, 18, 19, 20 or more years, and any combination or range derivable therein.

A. Transplanted Tissue and Organs

Though the first successful kidney transplant was performed in 1954 and the first heart and liver transplants were conducted in 1967, every year, thousands of people die in need of an organ transplant. Due to a variety of causes, they need hearts, lungs, kidneys, and livers. In addition, there are patients who could use a pancreas or a cornea. While there is a constant need for organ donors, another significant hurdle in providing those in need of an organ transplant with an organ is the limitations in current organ preservation techniques. For example, it is widely believed that a human heart must be transported within four hours for there to be any chance of the subsequent transplantation to be a success.

The two most frequently used methods for preserving/transporting hearts for transplantation are hypothermic storage and continuous perfusion. In the former method, the heart is arrested, removed from the donor, and then rapidly cooled and transported in cold storage. In the latter method, the following steps are typically employed: 1) pulsatile flow; 2) hypothermia; 3) membrane oxygenation, and 4) a perfusate containing both.

To improve the prospect of a successful transplant, techniques for better preserving an organ for transplantation have been developed. Two general areas of development have occurred, one in the area of preservation solutions and the other in the area of organ containers.

In certain contexts, such as transplant, adverse consequences of wound healing may impair or prevent proper engraftment of transplanted tissue. In the context of the present invention, it is envisioned that donated and recipient tissues will be treated post-transplantation with an oxygen antagonist, as discussed above with respect to wound healing, in an effort to inhibit biological processes such as inflammation, apoptosis and other wound healing/pre-transplantation events that damage engrafted tissues.

Because oxygen exchange with the air is very poor with solid tissue, it will be beneficial in some embodiments to provide the oxygen antagonist to the tissue or organ using the vasculature to deliver the oxygen antagonist to the inside of the cell. For example, a saline solution containing carbon monoxide can be administered to a donor subject prior to retrieving the tissue or organ for transplantation.

B. Other Preservation Agents

A variety of preservation solutions have been disclosed in which the organ is surrounded or perfused with the preservation solution while it is transported. One of the most commonly used solution is ViaSpan® (Belzer UW), which employed with cold storage. Other examples of such solutions or components of such solutions include the St. Thomas solution (Ledingham et al., J. Thorac. Cardiobasc. Surg. 93: 240-246, 1987), Broussais solution, UW solution (Ledingham et al., Circulation 82 (Part 2) IV351-8, 1990), Celsior solution (Menasche et al., Eur. J. Cardio. Thorax. Surg. 8: 207-213, 1994), Stanford University solution, and solution B20 (Bernard et al., J. Thorac. Cardiovasc. Surg. 90: 235-242, 1985), as well as those described and/or claimed in U.S. Pat. Nos. 6,524,785; 6,492,103; 6,365,338; 6,054,261; 5,719,174; 5,693,462; 5,599,659; 5,552,267; 5,405,742; 5,370,989; 5,066,578; 4,938,961; and, 4,798,824.

In addition to solutions, other types of materials are also known for use in transporting organs and tissue. These include gelatinous or other semi-solid material, such as those described, for example, in U.S. Pat. No. 5,736,397.

Some of the systems and solutions for organ preservation specifically involve oxygen perfusion in the solution or system to expose the organ to oxygen because it is believed that maintaining the organ or tissue in an oxygenated environment improves viability. See Kuroda et al., (Transplantation 46(3): 457-460, 1988) and U.S. Pat. Nos. 6,490,880; 6,046,046; 5,476,763; 5,285,657; 3,995,444; 3,881,990; and, 3,777,507. Isolated hearts that are deprived of oxygen for more than four hours are believed to lose vigor and not be useful in the recipient because of ischemic/reperfusion injury. See U.S. Pat. No. 6,054,261.

Moreover, many, if not all, of the solutions and containers for organ preservation and transplantation involve hypothermia (temperature below room temperature, often near but not below 0° C.), which has been called the "bed rock of all useful methods of organ and tissue preservation." U.S. Pat. No. 6,492,103.

To improve the prospect of a successful transplant, techniques for better preserving an organ for transplantation have been developed. Two general areas of development have occurred, one in the area of preservation solutions and the other in the area of organ containers.

Moreover, many, if not all, of the solutions and containers for organ preservation and transplantation involve hypothermia (temperature below room temperature, often near but not below 0° C.), which has been called the "bed rock of all useful methods of organ and tissue preservation." U.S. Pat. No. 6,492,103.

In the field of organ transplantation, certain conditions are believed to be related to the condition of the organ and prognosis for a successful transplantation: 1) minimization of cell swelling and edema; 2) prevention of intracellular acidosis; 3) minimization of ischemic damage; and 4) provision of substrate for regeneration of high energy phosphate compounds and ATP during reperfusion. Ischemic/reperfusion injury in organ transplantation is especially problematic because the harvested organ is removed from the body, isolated from a blood source, and thereby deprived of oxygen and nutrients for an extended period of time (U.S. Pat. No. 5,912,019). In fact, one of the most critical problems in transplantation today is the relatively high incidence of delayed graft function (DGF) due to acute tubular necrosis (ATN) after surgery. Current methods still experience problems in these areas, which highlights the importance of the present invention.

Nonetheless, the present invention can be used in conjunction with other preservation compositions and methods. As discussed in U.S. Pat. Nos. 5,952,168, 5,217,860, 4,559,258 and 6,187,529 (incorporated specifically by reference), biological materials can be preserved, for example, for keeping transplantable or replaceable organs long-term.

Cells, tissue/organs, or cadavers can be given compounds that enhance or maintain the condition of organs for transplantation. Such methods and compositions include those described in U.S. Pat. Nos. 5,752,929 and 5,395,314.

Moreover, methods of the present invention can include exposing biological matter to preservation solutions, such as those discussed, in addition to exposure to an oxygen antagonist.

It is contemplated that any agent or solution used with a biological sample that is living and that will be used as a living material will be pharmaceutically acceptable or pharmacologically acceptable. The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared either as liquid solutions or suspensions; solid forms suitable for solution in, or suspension in, liquid prior to use can also be prepared.

Organs for transplants may be monitored to assess their condition, particularly with respect to use as a transplant. Such methods are described in U.S. Pat. No. 5,699,793.

A number of drugs can be administered to a patient after receiving an organ transplant to assist in the recovery process. Such drugs include compounds and agents that reduce or inhibit an immune response against the donated organ.

Moreover, additional drugs are continually being researched and offered for use in organ transplants, such as those described in U.S. Pat. No. 6,552,083 (inhibitory agent comprising N-(3,4-dimethoxycinnamoyl)anthranililc acid) and 6,013,256 (antibodies that bind the IL-2 receptor, such as a humanized anti-Tax antibody).

C. Preservation Apparatuses

Systems or containers for transporting organs and tissues have also been developed through the years. Any of these embodiments may be combined with apparatuses of the invention, which allow for use with oxygen antagonists.

Most involve cooling systems for implementation, for example, those described in U.S. Pat. Nos. 4,292,817, 4,473,637, and 4,745,759, which employ active refrigeration with a cooling liquid that is pumped through the system. Several sophisticated devices have been designed involving multiple chambers or dual containers, such as is U.S. Pat. Nos. 5,434,045 and 4,723,974.

Some constitute a system in which an apparatus is devised for perfusion of the organ or tissue in a preservation solution, as is described in U.S. Pat. Nos. 6,490,880; 6,100,082; 6,046,046; 5,326,706; 5,285,657; 5,157,930; 4,951,482; 4,502,295; and, 4,186,565.

Some of the systems and solutions for organ preservation specifically involve oxygen perfusion in the solution or system to expose the organ to oxygen because it is believed that maintaining the organ or tissue in an oxygenated environment improves viability. See Kuroda et al., (Transplantation 46(3): 457-460, 1988) and U.S. Pat. Nos. 6,490,880; 6,046,046; 5,476,763; 5,285,657; 3,995,444; 3,881,990; and, 3,777,507. Isolated hearts that are deprived of oxygen for more than four hours are believed to lose vigor and not be useful in the recipient because of ischemic/reperfusion injury. See U.S. Pat. No. 6,054,261.

IV. Screening Applications

In still further embodiments, the present invention provides methods for identifying oxygen antagonists and molecules that act in a like fashion with respect to inducing stasis. In some cases, the oxygen antagonist being sought works like a chalcogenide compound in reducing core body temperature or preserving viability in hypoxic or anoxic environments that would otherwise kill the biological matter if it weren't for the presence of the oxygen antagonist. These assays may comprise random screening of large libraries of candidate substances; alternatively, the assays may be used to focus on particular classes of compounds selected with an eye towards attributes that are believed to make them more likely to act as oxygen antagonists. For example, a method generally comprises:

(a) providing a candidate modulator;
(b) admixing the candidate modulator with a biological matter;
(c) measuring one or more cellular responses characteristic of oxygen antagonist treatment; and
(d) comparing the one or more responses with the biological matter in the absence of the candidate modulator.

Assays may be conducted with isolated cells, tissues/organs, or intact organisms.

It will, of course, be understood that all the screening methods of the present invention are useful in themselves notwithstanding the fact that effective candidates may not be found. The invention provides methods for screening for such candidates, not solely methods of finding them. However, it will also be understand that a modulator may be identified as an effective modulator according to one or more assays, meaning that the modulator appears to have some ability to act as an oxygen antagonist, such as by inducing stasis in a biological matter. Screening, in some embodiments, involves using an assay described in the Examples to identify a modulator.

An effective modulator may be further characterized or assayed. Moreover, the effective modulator may be used in an in vivo animal or animal model (as discussed below) or be used in further in vivo animals or animal models, which may involve the same species of animals or in different animal species.

Furthermore, it is contemplated that modulator identified according to embodiments of the invention may also be manufactured after screening. Also, biological matter may be exposed to or contacted with an effective modulator according to methods of the invention, particularly with respect to therapeutic or preservation embodiments.

A. Modulators

As used herein the term "candidate substance" refers to any molecule that may induce stasis in biological matter by, for example, altering core body temperature. The candidate substance may be a protein or fragment thereof, a small molecule, or even a nucleic acid molecule. One may also acquire, from various commercial sources, small molecule libraries that are believed to meet the basic criteria for useful drugs in an effort to "brute force" the identification of useful compounds. Screening of such libraries, including combinatorally generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, siRNAs, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventor also contemplates that other structurally similar compounds may be formulated to mimic the key portions of the structure of the modulators. Such compounds, which may include peptidomimetics of peptide modulators, may be used in the same manner as the initial modulators.

B. In Vivo Assays

In vivo assays involve the use of various animal models. Due to their size, ease of handling, and information on their physiology and genetic make-up, mice are a preferred embodiment. However, other animals are suitable as well, including rats, rabbits, hamsters, guinea pigs, gerbils, woodchucks, mice, cats, dogs, sheep, goats, pigs, cows, horses and monkeys (including chimps, gibbons and baboons). Fish are also contemplated for use with in vivo assays, as are nematodes. Assays for modulators may be conducted using an animal model derived from any of these species.

In such assays, one or more candidate substances are administered to an animal, and the ability of the candidate substance(s) to induce stasis, reduce core body temperature, or endow on the biological material the ability to survive hypoxic or anoxic environmental conditions, as compared to an inert vehicle (negative control) and $H_2S$ (positive control), identifies a modulator. Treatment of animals with test compounds will involve the administration of the compound, in an appropriate form, to the animal. Administration of the candidate compound (gas or liquid) will be by any route that could be utilized for clinical or non-clinical purposes, including but not limited to oral, nasal (inhalation or aerosol), buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

VII. Modes of Administration and Pharmaceutical Compositions

An effective amount of a chalcogenide pharmaceutical composition, generally, is defined as that amount sufficient to detectably ameliorate, reduce, minimize or limit the extent of the condition of interest. More rigorous definitions may apply, including elimination, eradication or cure of disease.

A. Exposure

The routes of administration of an oxygen antagonist will vary, naturally, with the cell type, however, generally cells will be exposed to an oxygen antagonist by incubating them with oxygen antagonist (which may be a gas, liquid, or semi-solid liquid), immersing them in the oxygen antagonist (which may be a liquid or semi-solid liquid), injecting them with the oxygen antagonist (which may be a gas, liquid or semi-solid liquid), or perfusing them with the oxygen antagonist (which may be a liquid or semi-solid liquid). When the oxygen antagonist is a gas, it is contemplated that the gas may be blown onto the cells, or the cells may be exposed to the gas in a closed or significantly closed container or chamber.

Apparatuses discussed herein can be used to expose cells to an oxygen antagonist. It is contemplated that the oxygen antagonist can be cycled in and out of a chamber or container in which the cells are, or that the amount of the oxygen antagonist to which the cells are exposed can vary periodically or intermittently.

B. Formulations

Solutions of the active compounds may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Perfusion Systems

A perfusion system for cells may be used to expose a tissue or organ to an oxygen antagonist in the form of a liquid or a semi-solid. Perfusion refers to continuous flow of a solution through or over a population of cells. It implies the retention of the cells within the culture unit as opposed to continuous-flow culture, which washes the cells out with the withdrawn media (e.g., chemostat). Perfusion allows for better control of the culture environment (pH, $pO_2$, nutrient levels, oxygen antagonist levels, etc.) and is a means of significantly increasing the utilization of the surface area within a culture for cell attachment.

The technique of perfusion was developed to mimic the cells milieu in vivo where cells are continuously supplied with blood, lymph, or other body fluids. Without perfusion of a physiological nutrient solution, cells in culture go through alternating phases of being fed and starved, thus limiting full expression of their growth and metabolic potential. In the context of the present invention, a perfusion system may also be used to perfuse cells with an oxygen antagonist to induce stasis.

Those of skill in the art are familiar with perfusion systems, and there are a number a perfusion systems available commercially. Any of these perfusion systems may be employed in the present invention. One example of a perfusion system is a perfused packed-bed reactor using a bed matrix of a non-woven fabric (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 μm to 100 μm, providing for a high internal volume with pore volumes corresponding to 1 to 20 times the volumes of individual cells.

The perfused packed-bed reactor offers several advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium, which facilitates subsequent purification steps. This technology is explained in detail in WO 94/17178 (Aug. 4, 1994, Freedman et al.), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plates joined to create thin sealed laminar flow spaces between adjacent plates.

The Cellcube™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Other commercially available perfusion systems include, for example, CellPerf® (Laboratories MABIO International, Tourcoing, France) and the Stovall Flow Cell (Stovall Life Science, Inc., Greensboro, N.C.)

The timing and parameters of the production phase of cultures depends on the type and use of a particular cell line. Many cultures require a different media for production than is required for the growth phase of the culture. The transition from one phase to the other will likely require multiple washing steps in traditional cultures. However, one of the benefits of a perfusion system is the ability to provide a gentle transition between various operating phases. The perfusion system can also facilitate the transition from a growth phase to a static phase induced by an oxygen antagonist. Likewise, the perfusion system can facilitate the transition from a static phase to a growth phase by replacing the solution comprising an oxygen antagonist with, for example, a physiological nutrient media.

D. Delivery of Gases

1. Respiration System

In another embodiment of the present invention, gases are delivered to cells, tissues, organs, organ systems or organisms. The general features of systems that provide gases include a reservoir for the source gas operably connected to a chamber of sufficient size/shape to permit enclosure of the appropriate subject matter. The system will also comprise means for controlling introduction of the gas, and optionally its evacuation from the chamber. Such means may comprise one or more valves, pumps, fans or vents, or combinations thereof. In addition, such features may be automated and controlled by computers and computer programs.

Figure 9:
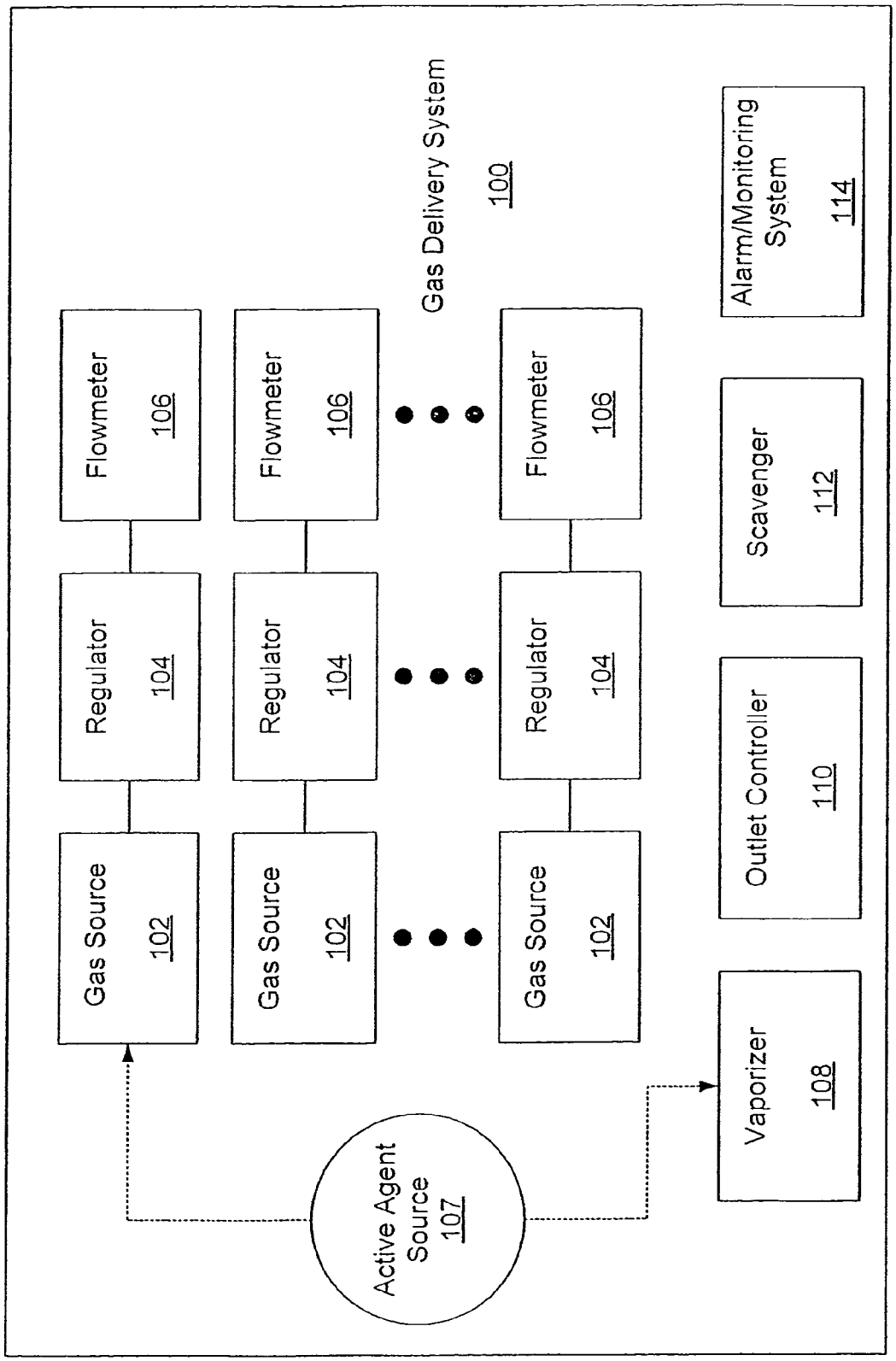
FIG. 9 is a block diagram illustrating a respiration gas delivery system according to embodiments of the present invention.

An exemplary gas delivery system 100 is illustrated in FIG. 9. The delivery system 100 is suited for delivering breathable gases, including an active agent, to the respiration system of a subject. It can be modified for use with tissue instead of an organism. The gas delivery system 100 includes one or more gas sources 102. Each of the gas sources 102 is connected to a regulator 104 and a flowmeter 106. The gas delivery system 100 also includes an active agent source 107, an optional vaporizer 108, an outlet controller 110, a scavenger 112, and an alarm/monitoring system 114.

The delivery system 100 may include certain elements generally used in an anesthesia delivery machine. For example, anesthesia delivery machines generally include a high pressure circuit, a low pressure circuit, a breathing circuit, and a scavenging circuit. As described in FIGS. 10-11, one or more of the gas sources 102, the vaporizer 108, the outlet controller 110, the scavenger 112, and/or the alarm/monitoring system 114 may be provided as part of a device having a high pressure, low pressure, breathing, and/or scavenging circuit, and these elements may be similar to those generally used in an anesthesia delivery machine. Anesthesia delivery machines are described, for example, in U.S. Pat. Nos. 4,034,753; 4,266,573; 4,442,856; and 5,568,910, the contents of which are hereby incorporated by reference in their entireties.

The gas sources 102 may be provided by tanks of compressed gas; however, it should be understood that the gas sources 102 can be either a gas or a liquid source that is converted to a gas. For example, the vaporizer 108 can be used to vaporize a liquid gas source. The regulators 104 include valves that reduce the pressure of each of the gas sources 102. The decompressed gas then passes through one of the flowmeters 106, which measures and controls the flow of gas from each of the respective gas sources 102.

The gas sources 102 may be carrier gases that are used to deliver the active agent 107. The carrier gases may be selected to provide a desired environment for a subject to which the active agent from the source 107 is delivered. For example, if the active agent is delivered to a patient as a breathable gas, the carrier gases can include oxygen, nitrous oxide, or air in sufficient quantities to satisfy the needs of the patient. Other inert or active gases may be used.

In some embodiments, one of the gas sources 102 includes the active agent source 107. The active agent from the source 107 may be a liquid gas source that is vaporized by the vaporizer 108 or the active agent may be a gaseous source, such as a compressed gas under high pressure. The active agent can be mixed with one or more of the gas sources 102. The outlet controller 110 controls the amount of the gas mixture that is provided to the subject.

The scavenger 112 is a device or system that scavenges and/or ventilates the gases that are provided to the subject. For example, if the active agent from the source 107 is provided as a breathable gas to a patient, the scavenger 112 can be used to remove the waste gases of the inhalant (such as the active agent), unused oxygen, and exhaled carbon dioxide.

The alarm/monitoring system 114 includes sensors that monitor the gas flow and/or gas content at one or more locations within the delivery system 100. For example, the flow or amount of oxygen may be monitored when the active agent from the source 107 is provided as a breathable gas to a patient to ensure that the carrier gases include sufficient oxygen for the patient. The alarm/monitoring system 114 also includes a user interface that is configured to provide an audio or visual alarm or monitoring information to a user of the delivery system 100, such as a visual display, a light, or audio alarm. The alarm/monitoring system 114 can be configured to notify the user when a predetermined condition is met and/or to provide information regarding gas levels.

Figure 10:
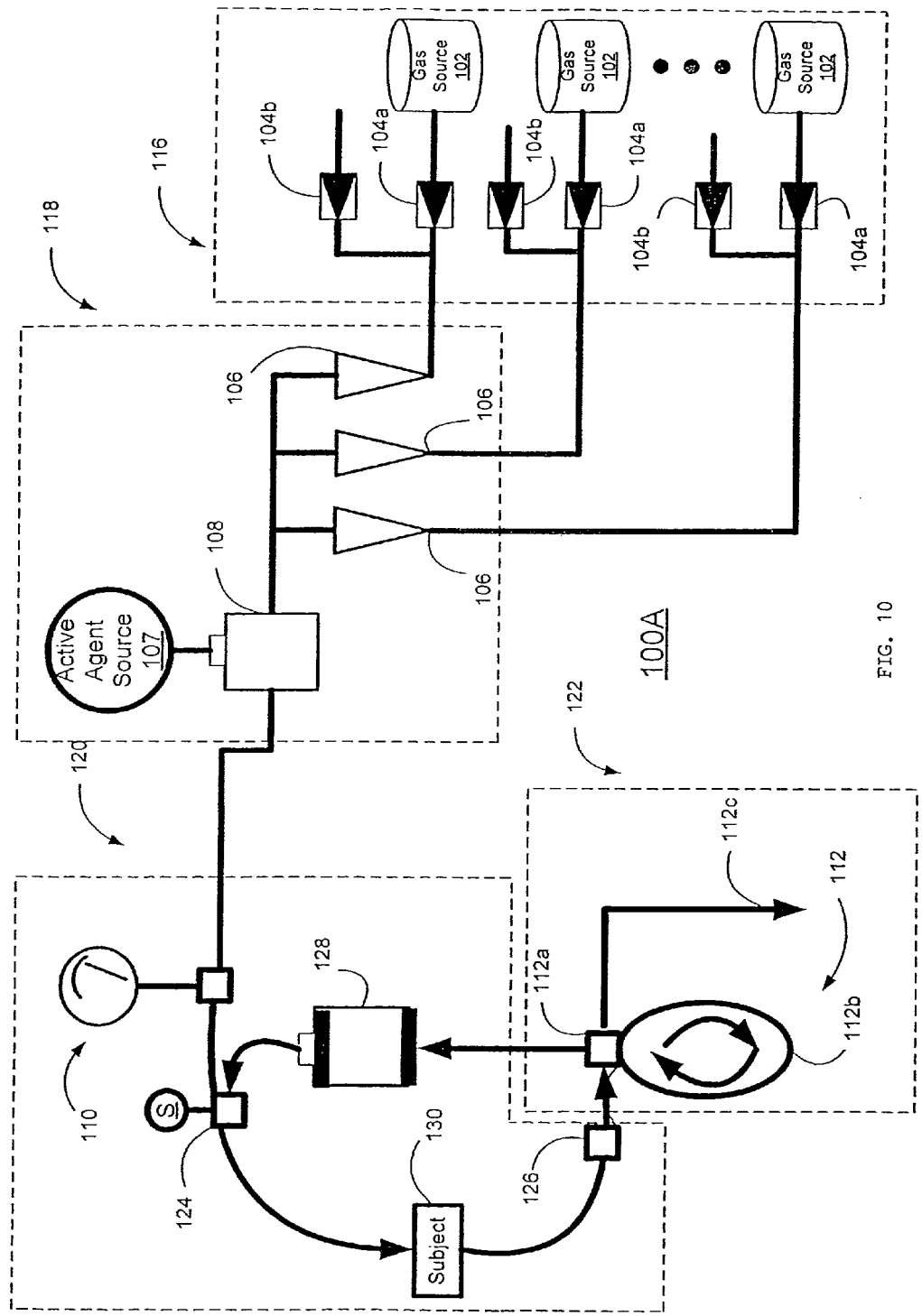
FIG. 10 is a schematic drawing illustrating a respiration gas delivery system according to embodiments of the present invention.

With reference to FIG. 10, a system 100A includes a high pressure circuit 116, a low pressure circuit 118, a breathing circuit 120, and a scavenging circuit 122.

The high pressure circuit 116 includes the compressed gas sources 102, which are connected to regulator valves 104b, 104a. The regulator valves 104a control the amount of gas that flows from each of the gas sources 102, and the regulator valves 104b may be opened to increase the pressure of the gas, for example, by providing an opening to the surrounding atmosphere.

The low pressure circuit 118 includes the flowmeters 106, the active agent source 107, and the vaporizer 108. A gas mixture from the gas sources 102 is provided by the flowmeters 106, which control the amount of each of the gases from the gas sources 102. As illustrated in FIG. 10, the active agent source 107 is a liquid. The active agent source 107 is vaporized by the vaporizer 108 and added to the gas mixture.

The breathing circuit 120 includes the outlet controller 110, two one-way valves 124, 126 and an absorber 128. The scavenger circuit 122 includes a valve 112a, a reservoir 112b, and an outlet 112c. A subject 130 receives the gas mixture from the outlet controller 110 and the resulting gas is ventilated by the scavenger circuit 122. More specifically, the outlet controller 110 controls the amount of the gas mixture that is delivered to the subject 130 via the one-way valve 124. Expired gases flow through the one-way valve 126 to the valve 112a and to the reservoir 112b. Excess gases exit through the outlet 112c of the scavenger 112. Some of the gases may be recycled and flow through the absorber 128 and into the breathing circuit 120. The absorber 128 may be a carbon dioxide absorbing canister for reducing carbon dioxide gases from exhaled gases. In this configuration, expired oxygen and/or active agent may be re-circulated and reused.

Figure 11:
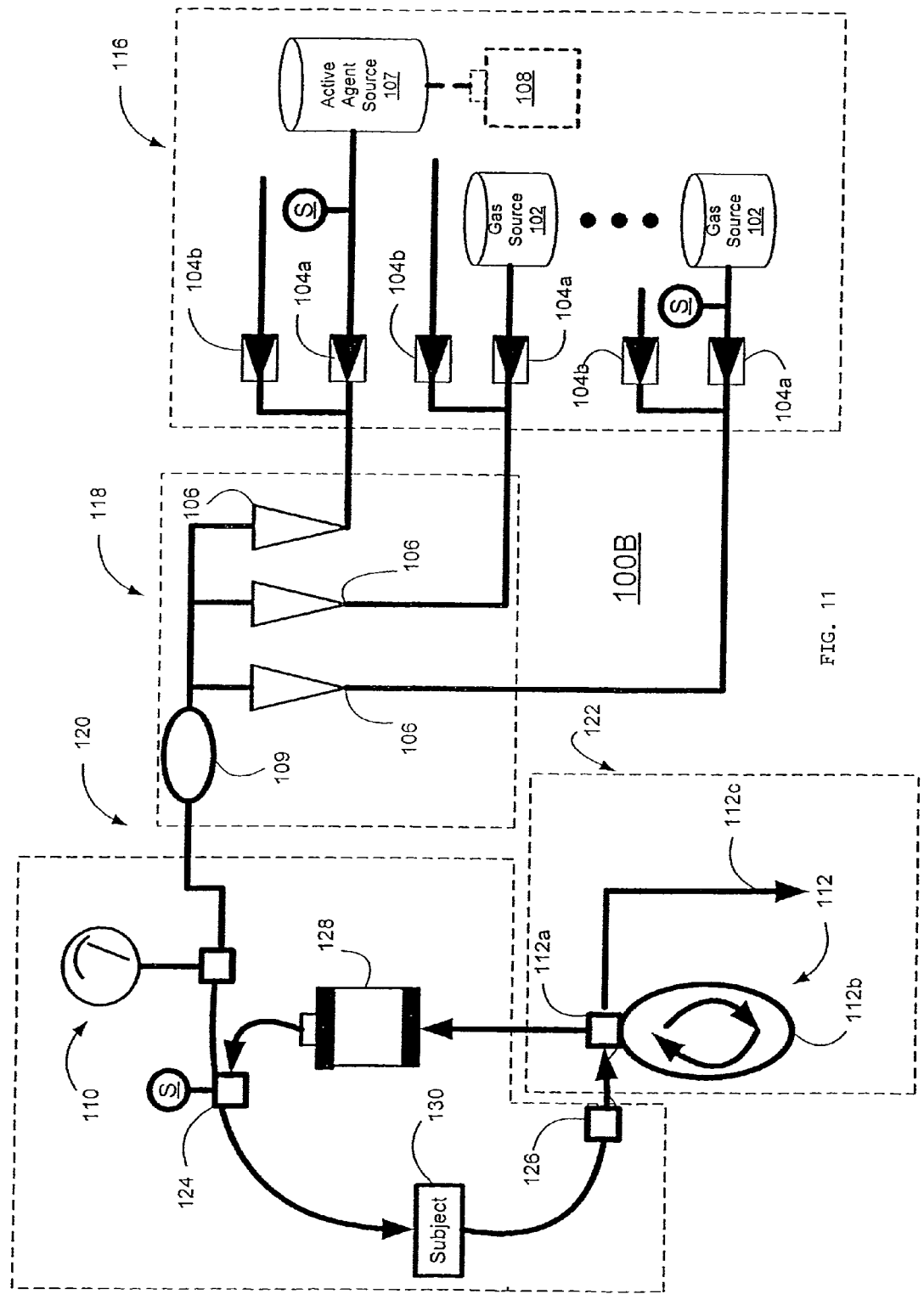
FIG. 11 is a schematic drawing illustrating a respiration gas delivery system according to further embodiments of the present invention.

One or more sensors S may be added at various positions in the system 100A. The sensors S sense and/or monitor the gases in the system 100A. For example, if one of the gas sources 102 is oxygen, one of the sensors S may be an oxygen sensor configured and positioned to monitor the oxygen in the system 100A so that the patient receives a suitable amount of oxygen. The sensors S are in communication with the alarm/monitoring system 114 (see FIG. 9). If undesirable or dangerous gas levels are present in the system 100, the alarm/monitoring system 114 may alert a user of the system 100A so that appropriate action may be taken, such as increasing the oxygen levels given to the subject 130 or disconnecting the subject 130 from the delivery system With reference to FIG. 11, a system 100B is shown in which the active agent source 107 is connected to two of the regulator valves 104b, 104a. If the active agent source 107 is a liquid gas source, an optional vaporizer 108 is provided to vaporize the liquid gas source. If the active agent source 107 is gaseous (e.g., a high pressure gas), then the vaporizer 108 may be omitted. The active agent from the source 107 is mixed with the other gas sources 102 in the low pressure circuit 118 in amounts that are controlled by the flowmeters 106. The low pressure circuit 118 includes a gas reservoir 109 that contains any overflow of the gas mixture as it flows to the breathing circuit 120. It should be understood that the active agent source 107 and/or any of the gas sources 102 may be provided as a liquid gas source with a vaporizer. The elements of the system 100B illustrated in FIG. 11 are essentially the same as those described above with respect to FIG. 10 and will not be described further.

Figure 12:
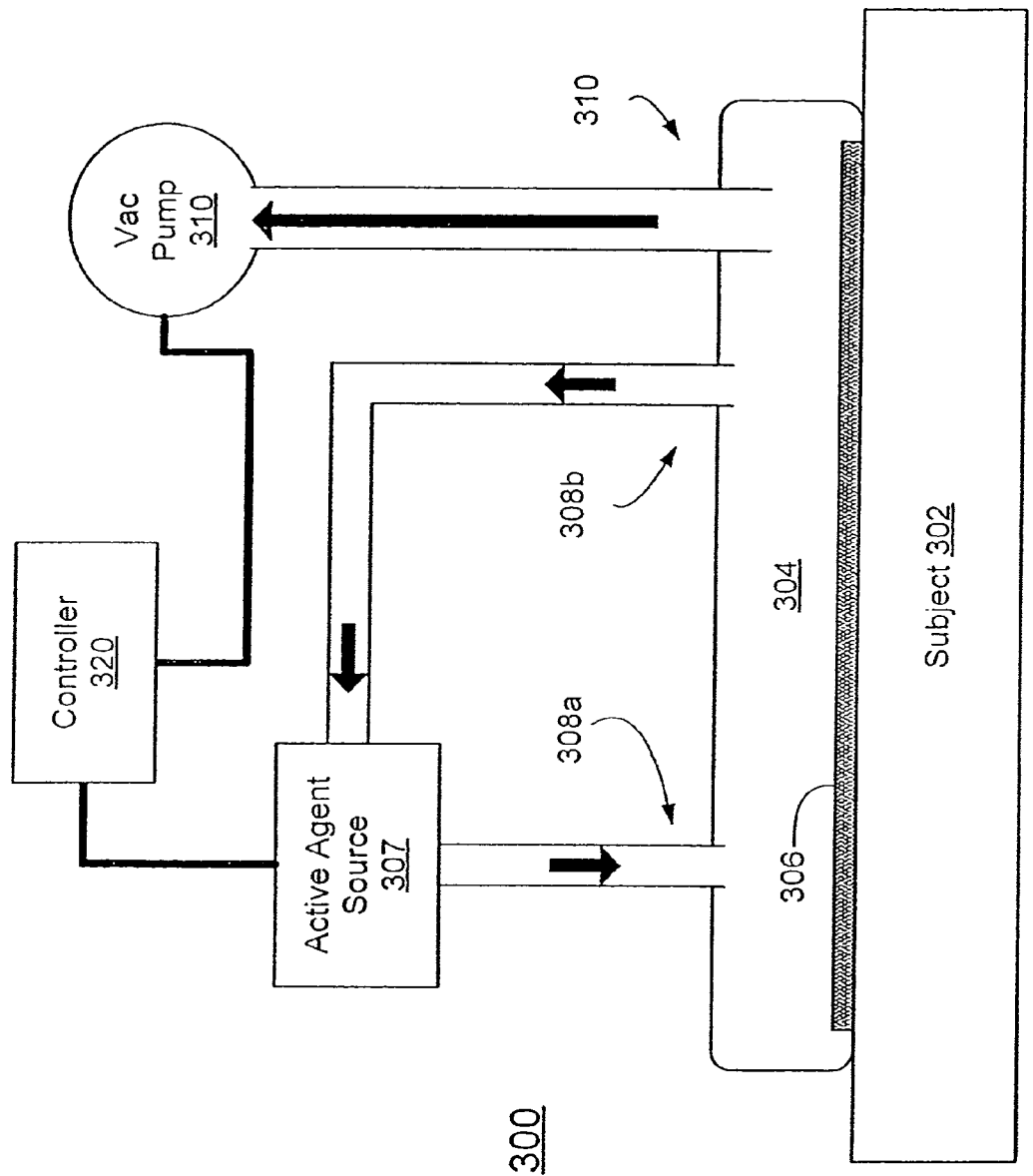
FIG. 12 is a flowchart illustrating operations according to embodiments of the present invention.

Methods according to embodiments of the present invention which may be carried out using the systems 100, 100A, 100B are illustrated in FIG. 12. A mixture of one or more breathable gas sources is provided (Block 202). The breathable gas sources may be obtained from the gas sources 102 as described with respect to FIGS. 9-11. A predetermined amount of the active agent is added to the gas mixture (Block 204), such as is shown with respect to the active agent source 107 in FIGS. 9-11. The gas mixture is administered to the subject 120 (Block 306). Exhaled gases are ventilated and/or recycled (Block 208), for example, by the scavenger 112. Although the methods of FIG. 12 are described with respect to the systems 100, 100A, 100B of FIG. 9-11, it should be understood that any suitable system or device may be used to carry out the steps in FIG. 12.

2. Reduced Pressure Delivery System

Figure 13:
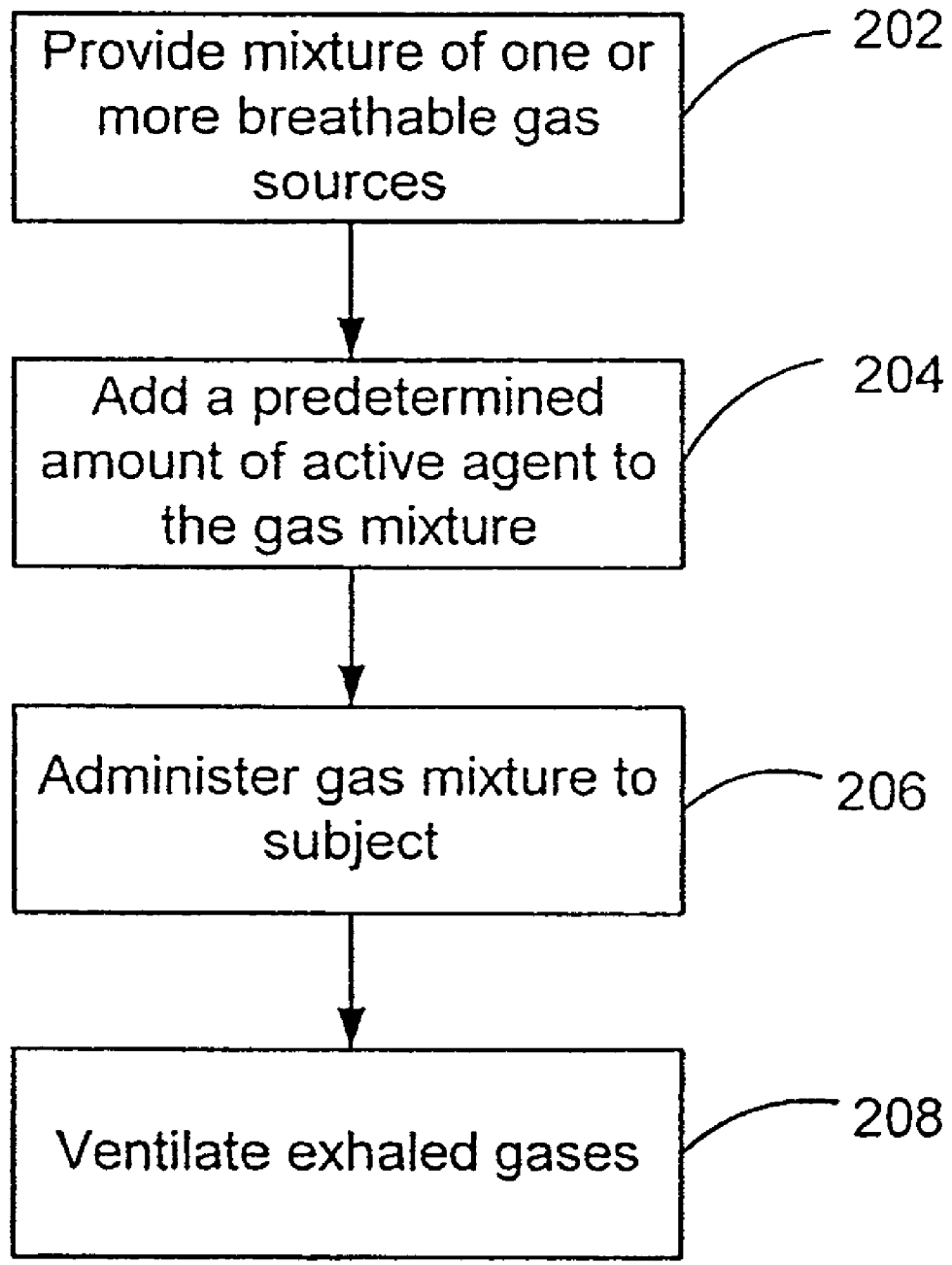
FIG. 13 is a schematic drawing illustrating a tissue treatment gas delivery system according to embodiments of the present invention.

Embodiments of a gas delivery system 300 are illustrated with respect to FIG. 13. The gas delivery system 300 is positioned on a subject 302. The gas delivery system 300 is particularly suited to deliver an active agent in a gas mixture to the tissue of a subject 302, for example, wound tissue.

The system 300 includes a reduced pressure chamber 304 having a screen 306 that covers the treatment area of the subject 302. The reduced pressure chamber 304 is connected to a vacuum pump 310 by a pump outlet 310a. The reduced pressure chamber 304 includes an inlet 308a and an outlet 308b, which are in turn connected to an active agent source 307. A controller 320 is connected to the active agent source 307 and the vacuum pump 310. Reduced pressure chambers and vacuum pump systems are discussed in U.S. Pat. Nos. 5,645,081 and 5,636,643, the contents of which are hereby incorporated by reference in their entireties.

The reduced pressure chamber 304 is configured to enclose an area of the subject 302 to provide a fluid-tight or gas-tight enclosure to effect treatment of the area with reduced or negative pressure and the active agent source 307. The pressure chamber 304 can be affixed to the subject 302 with a cover (not shown), such as a flexible, adhesive, fluid impermeable polymer sheet. The cover can have an adhesive backing that functions to cover the skin around the periphery of the area being treated and to provide a generally gas-tight or fluid-tight seal and to hold the chamber 304 in position.

The screen 306 is positioned over the treatment area of the subject 302. For example, if the treatment area of the subject 302 includes a wound, the screen 306 can be positioned over the wound to prevent its overgrowth. The size and configuration of the screen 306 can be adjusted to fit the individual treatment area, and may be formed from a variety of porous materials. The material should be sufficiently porous to allow oxygen any other gases, such as gases from the active agent source 307, to reach the treatment area. For example, the screen 306 can be in the form of an open-cell polymer foam, such as a polyurethane foam, which is sufficiently porous to allow gas flow to and/or from the treatment area. Foams may be used that vary in thickness and rigidity, although it may be desirable to use a spongy material for the patient's comfort if the patient must lie upon the appliance during treatment. The foam may also be perforated to enhance gas flow and to reduce the weight of the system 300. The screen 306 may be cut to an appropriate shape and size to fit within the treatment area, or alternatively, the screen 306 may be sufficiently large to overlap the surrounding skin.

The vacuum pump 310 provides a source of suction within the reduced pressure chamber 304. The active agent source 307 provides an amount of the active agent to the reduced pressure chamber 304. The controller 320 controls the amount of vacuum applied to the reduced pressure chamber 304 by the vacuum pump 310 and the amount of the active agent that is supplied to the chamber 304 by the active agent source 307.

It should be understood that the controller 320 can apply a vacuum and/or the active agent in a substantially constant manner, cyclically, or using various fluctuations or patterns or any combination thereof. In some embodiments, the active agent is supplied by the active agent source 307 alternatively with the vacuum pumping action of the vacuum pump 310. That is, the controller 320 alternatively activates the vacuum pump 310 while deactivating the active agent source 307 and then activates the active agent source 307 while deactivating the vacuum pump 310. The pressure in the reduced pressure chamber 304 is allowed to fluctuate. In other embodiments, a substantially constant pressure is maintained by the vacuum pump 310 and the active agent source 307 provides a substantially constant amount of active agent to the chamber 304 in the reduced pressure environment. In some embodiments, a substantially constant pressure is maintained by the vacuum pump 310 and the amount of the active agent varies in a cyclical manner. In other embodiments, the pressure in the reduced pressure chamber 304 is made to fluctuate by the vacuum pump 310, and the amount of active agent supplied by the source 307 also fluctuates. The fluctuations of either the vacuum pump 310 and the resulting pressure in the chamber 304 or the amount of active agent supplied by the source 307 may be cyclical or not cyclical.

Figure 14:
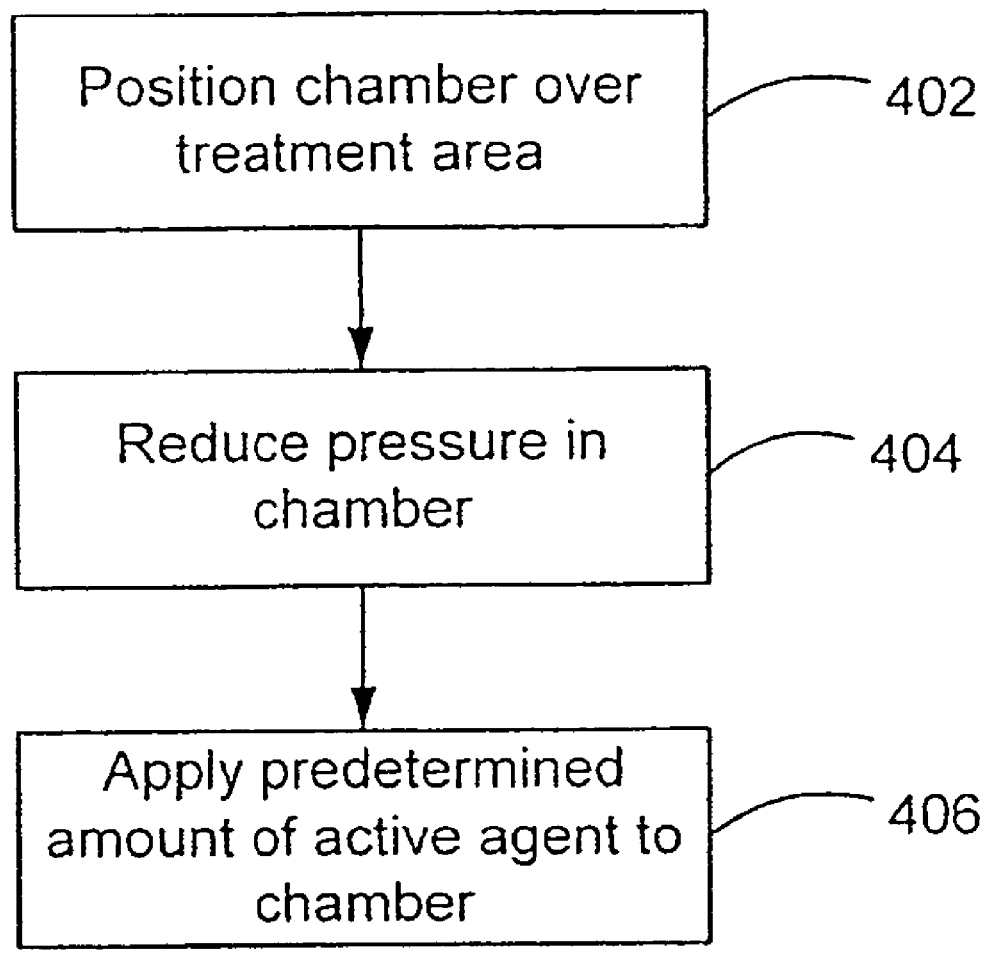
FIG. 14 is a flowchart illustrating operations according to embodiments of the present invention.

Methods according to embodiments of the present invention which may be carried out using the system 300 are illustrated in FIG. 14. The chamber 304 is positioned over the treatment area of the subject 302 (Block 402). Pressure is reduced in the chamber 304 by the vacuum pump 310 (Block 404). A predetermined amount of active agent from the active agent source 307 is applied to the chamber (Block 406). Although the methods of FIG. 6 are described with respect to the system 300 of FIG. 5, it should be understood that any suitable system or device may be used to carry out the steps in FIG. 14. For example, the outlet 308b may be omitted and the active agent may be supplied to the chamber 304 by the single inlet 308a. Other gases may also be added to the chamber 304, for example, using a single inlet or an inlet and an outlet, such as is illustrated with respect to the active agent source 307 and the inlet 308a and the outlet 308b. In some embodiments, the vacuum pump 310 is attached to an additional collection container between the pump 310 and the chamber 304 for collecting exudates from the treatment area, for example, as described in U.S. Pat. No. 5,636,643.

Negative pressure gas delivery systems 300 as illustrated in FIG. 13 are useful for treating a variety of areas for treatment, and, in particular, for treating wounds. Wounds that may be treated using the system 300 include infected open wounds, decubitus ulcers, dehisced incisions, partial thickness burns, and various lesions to which flaps or grafts have been attached. Treatment of a wound can be carried out by securing a gas delivery system to the treatment site as previously shown and described, maintaining a substantially continuous or cyclical reduced pressure within the reduced pressure chamber 304 and supplying the active agent to the chamber 304 in a substantially continuous or cyclical fashion until the wound has reached a desired improved condition. A selected state of improved condition may include formation of granulation tissue sufficient for the attachment of a flap or graft, reduction of microbial infection in the wound, arrest or reversal of burn penetration, closure of the wound, integration of a flap or graft with the underlying wounded tissue, complete healing of the wound, or other stages of improvement or healing appropriate to a given type of wound or wound complex. The gas delivery system may be changed periodically, such as at 48 hrs intervals, during treatment, particularly when using a gas delivery system incorporating a screen on or in the wound. The method may be practiced using a negative or reduced pressure ranging from 0.01 to 0.99 atmospheres, or the method may be practiced using a negative or reduced pressure ranging between 0.5 to 0.8 atmospheres. The time period for use of the method on a wound may be at least 12 hrs, but can be, for example, extended for one or more days. There is no upper limit beyond which use of the method is no longer beneficial; the method can increase the rate of closure up to the time the wound actually closes. Satisfactory treatment of various types of wounds may be obtained via the use of reduced pressures equivalent to about 2 to 7 in. Hg below atmospheric pressure.

Supplying reduced pressure to the gas delivery system in an intermittent or cyclic manner, such as described above, may be useful for treating wounds in the presence of the active agent. Intermittent or cyclic supply of reduced pressure to a gas delivery system may be achieved by manual or automatic control of the vacuum system. A cycle ratio, the ratio of "on" time to "off" time, in such an intermittent reduced pressure treatment may be as low as 1:10 or as high as 10:1. A typical ratio is approximately 1:1 which is usually accomplished in alternating 5 minute intervals of reduced pressure supply and non-supply.

A suitable vacuum system includes any suction pump capable of providing at least 0.1 pounds of suction to the wound, or up to three pounds suction, or up to fourteen (14) pounds suction. The pump can be any ordinary suction pump suitable for medical purposes that is capable of providing the necessary suction. The dimension of the tubing interconnecting the pump and the reduced pressure appliance is controlled by the pump's ability to provide the suction level needed for operation. A ¼ inch diameter tube may be suitable.

Embodiments of the present invention also include methods of treating damaged tissue which include the steps of applying negative pressure to a wound and the active agent for a selected time and at a selected magnitude sufficient to reduce bacterial density in the wound. Open wounds are almost always contaminated with harmful bacteria. Generally a bacterial density of $10^5$ bacterial organisms per gram of tissue is regarded as infected. It is generally accepted that at this level of infection, grafted tissue will not adhere to a wound. These bacteria must be killed, either through the wound host's natural immune response or through some external method, before a wound will close. The application of negative pressure and active agent to a wound may reduce the bacterial density of the wound. It is believed that this effect may be due to the bacteria's incompatibility with a negative pressure environment or the increased blood flow to the wound area in combination with exposure to the active agent, as blood brings with it cells and enzymes to destroy the bacteria. Methods according to embodiments of the present invention can be used to reduce bacterial density in a wound by at least half. In some embodiments, it can be used to reduce bacterial density by at least 1,000-fold or by at least 1,000,000-fold.

Embodiments of the present invention also include methods of treating a burn which include the steps of applying negative pressure and the active agent to the burn over an area with predetermined reduced pressure and for a time sufficient to inhibit formation of a full thickness burn. A partial thickness burn, one which has a surface layer of dead tissue and an underlying zone of stasis, is often sufficiently infected so that it will transform within 24-48 hrs into a full thickness burn, one in which all epidermal structures are destroyed. The application of negative pressure and an amount of the active agent to the wound may prevent the infection from becoming sufficiently severe to cause destruction of the underlying epidermal structures. The magnitude, pattern, and duration of pressure application can vary with the individual wound.

Embodiments of the present invention also include methods for enhancing the attachment of living tissue to a wound which comprises the steps of first joining the living tissue to the wound to form a wound-tissue complex, then applying a negative or reduced pressure of selected magnitude and an amount of the active agent to the wound-tissue complex over an area sufficient to promote migration of epithelia and subcutaneous tissue toward the complex, with the negative pressure and exposure to the active agent being maintained for a selected time period sufficient to facilitate closure of the wound. Attachment of living tissue to a wound is a common procedure that can take many forms. For example, one common technique is the use of a "flap," a technique in which skin tissue from an area adjacent to the wound is detached on three sides but remains attached on the fourth, then is moved onto the wound. Another frequently used technique is an open skin graft in which skin is fully detached from another skin surface and grafted onto the wound. The application of negative pressure and active agent to the wound-graft complex reduces bacterial density in the complex and improves blood flow to the wound, thereby improving the attachment of the grafted tissue.

VIII. Combination Therapies

The compounds and methods of the present invention may be used in the context of a number of therapeutic applications, particularly organ transplants or skin grafts. In order to increase the effectiveness of a treatment with the compositions of the present invention, such as oxygen antagonists, it may be desirable to combine these compositions with other agents effective in the treatment of the underlying diseases and conditions or to promote acceptance of the transplant (secondary therapy). For example, immunosuppressants may be administered in conjunction with transplanting the organ or tissue.

Various combinations may be employed; for example, an oxygen antagonist, such as $H_2S$, is "A" and the secondary therapy is "B":

| A/B/A | B/A/B | B/B/A | A/A/B | A/B/B | B/A/A | A/B/B/B | B/A/B/B |
|---|---|---|---|---|---|---|---|
| B/B/B/A | | B/B/A/B | A/A/B/B | A/B/A/B | A/B/B/A | | B/B/A/A |
| B/A/B/A | | B/A/A/B | A/A/A/B | B/A/A/A | A/B/A/A | | A/A/B/A |

Administration of the oxygen antagonists of the present invention to biological matter will follow general protocols for the administration of that particular secondary therapy, taking into account the toxicity, if any, of the oxygen antagonist treatment. It is expected that the treatment cycles would be repeated as necessary. It also is contemplated that various standard therapies, as well as surgical intervention, may be applied in combination with the described therapies.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preservation of Nematodes in Carbon Monoxide

The atmosphere contains 210,000 ppm oxygen. Exposure to low levels of oxygen, or hypoxia, results in cellular damage and death in humans. In the nematode, *C. elegans*, oxygen concentrations between 100 ppm and 1000 ppm are also lethal. By critically studying the response of nematodes to a range of oxygen tensions, it was found that oxygen concentrations below 10 ppm and above 5000 ppm are not lethal. In 10 ppm oxygen balanced with nitrogen, nematodes enter into a state of reversible suspended animation in which all aspects of animation observable under the light microscope ceases (Padilla et al., 2002). In oxygen concentrations of 5000 ppm (balanced with nitrogen) and above, nematodes progress through their life cycle normally. In a search for drugs that protect nematodes against hypoxic damage, carbon monoxide was tested.

To achieve specific atmospheric conditions the following apparatus was used: a glass syringe barrel having a tip with a locking device such as a LUER-LOK with the large opening of the barrel sealed with a custom-machined steel and rubber fitting to make an airtight seal was locked to via locking device to the inlet port of an environmental chamber having an inlet and an outlet port each fitted with a locking devices such as a LUER-LOK fitting. A defined gas was humidified and provided to the environmental chamber by first venting the gas from a compressed tank (Byrne Specialty Gas, Seattle, Wash.) through a gas washing bottle (500 ml Kimex) filled with double distilled water. The gas washing bottle was connected to the environmental chamber past a gas-flow meter. A gas flow meter was used to provide a regulated 70 cc/min flow through the environmental chamber throughout the 24 hr incubation.

To test whether induced, reversible stasis could be achieved in *C. elegans* nematodes, 2-cell *C. elegans* embryos, L3 larvae or adult nematodes were collected and exposed to either an environment of effectively 100% CO, an environment of 100% $N_2$, an environment comprising 500 ppm oxygen balanced with carbon monoxide, or to environments comprising 100, 500 or 1000 ppm oxygen balanced with nitrogen at room temperature. Nematodes were visualized using differential interference contrast microscopy (also known as Nomarski optics). Images were collected and analyzed using NIH image and Adobe Photoshop 5.5. Embryos are approximately 50 µm in length.

Results of these experiments showed that 100% carbon monoxide was not lethal and induced reversible suspended animation. Nematodes did not survive 500 ppm oxygen balances with nitrogen, however, those treated with 500 ppm oxygen balanced with carbon monoxide entered into suspended animation and survived. See below:

Example 2

Preservation of Human Skin in Carbon Monoxide

Carbon monoxide is extraordinarily toxic to humans because it strongly competes with oxygen for binding to hemoglobin, the primary molecule that distributes oxygen to tissues. The fact that nematodes, which do not have hemoglobin, are resistant to carbon monoxide and even protected against hypoxic damage by this drug suggested the possibility that carbon monoxide would protect against hypoxic damage in human tissue in situations where blood is not present, such as in tissue transplant or blood free surgical fields. To tested this hypothesis using human skin.

Three human foreskins were obtained for this purpose. The foreskin tissue was preserved in keratinocyte growth medium (KGM) containing insulin, EGF (0.1 ng/ml), hydrocortisone (0.5 mg/ml) and bovine pituitary extract (approx. 50 micrograms/ml of protein). Foreskins were rinsed in PBS, and excess fatty tissue was removed. Each foreskin sample was divided into 2 equal pieces. Each piece was placed into a separate container containing a solution of PBS with 24 mg/ml of Dispase II (from *Bacillus Polymyxa* EC 3.4.24.4: Roche Diagnostics Corp., Indianapolis, Ind.). One container (containing a foreskin piece in PBS with Dispase II) was kept in a humid chamber in a fume hood. The other container (with the other half of the foreskin in PBS with Dispase II) was placed in the same fume hood in an environmental chamber perfused with humidified 100% CO. Both samples were maintained at room temperature for 24 hrs. Methods used to establish defined atmospheric conditions were identical to those used in Example 1.

Following the 24 hr exposure to normoxia or 100% CO, keratinocytes were isolated from the foreskins according to the method described by Boyce et al. (1983; 1985; each of which is incorporated herein by reference in its entirety). Briefly, the epidermis from each foreskin sample was removed to a fresh dish containing PBS. The epidermis was minced and homogenized prior to incubation in 3 ml of 0.05% Trypsin, 1 mM EDTA for 5 minutes, at room temperature, to separate basal cells from the epidermis. After incubation, 6 ml of 400 µg/ml (micrograms per ml) Soybean Trypsin Inhibitor, 1 mg/ml BSA was added and the samples were centrifuged at 900 RPM. The supernatant from each sample was discarded and the sample pellets were resuspended in 10 ml of KGM. Each sample was split into two 10 cm plates each of which contained 5 ml KGM and 100 µl of HEPES pH 7.3 (N-2-hydroxyethylpiperazine-N'-2-ethane sulfonic acid). The plates were incubated in a 37° C. incubator perfused with 95% room air, 5% carbon dioxide for five days.

Cells were inspected visually using an inverted phase contrast microscope. All three of the keratinocyte populations exposed to normoxia showed little or no growth. All three of the keratinocyte populations exposed to 100% CO showed significant growth. Quantitation of the number of viable keratinocytes as judged by colony formation was quantified for two of the three foreskins. See FIG. 1.

TABLE 1

Quantitation of Colony Formation

| Foreskin | Atmosphere | Total colonies |
|---|---|---|
| 1 | 100% CO | 542 colonies (many of which were very large) |
| 1 | Normoxia | 2 colonies (both small) |
| 2 | 100% CO | 780 colonies (many of which were very large) |
| 2 | Normoxia | 0 colonies |

Example 3

More Information Related to Example 1

The following example contains information that overlaps and extends the information disclosed in Example 1.

A. Materials and Methods

Environmental chambers and apparatuses. Oxygen deprivation experiments were carried out using a custom atmospheric chamber designed by W. Van Voorhies (Van Voorhies et al., 2000). The chamber is a 30 mL glass syringe (Fisher #14-825-10B) fitted with a custom steel stopper that is lined with two viton o-rings to ensure a tight seal. The stopper is bored through and has a steel lure lock on the exterior face so that a hose carrying compressed gas can be attached. A defined gas mixture is delivered to the chamber at a constant pressure and flow rate from compressed tanks by passing first through a rotameter (Aalborg, flow-tube number 032-41ST) or mass flow controller (Sierra Instruments #810) to monitor flow rate and then through a 500 ml gas washing bottle (Fisher #K28220-5001) containing 250 ml water to hydrate the gas. ¼" OD nylon (Cole-Parmer #P-06489-06) or FEP (Cole-Parmer #A-06450-05) tubing was used and connections between tubing and the regulators and between the tubing and the rotameters were made with brass John-Guest-type fittings (Byrne Gas). All other connections were made with either microflow quick-connect fittings (Cole-Parmer #A-06363-57, #A-06363-52) or standard lure fittings (Cole-Parmer #A-06359-37, #A-06359-17).

Viability of nematodes in hypoxia. Bristol strain N2 were continuously maintained at 20° C. with care taken to ensure the population did not starve. Log-phase, adult *C. elegans* were picked into a drop of sterile water containing 100 µg/ml ampicillin, 15 µg/ml tetracycline and 200 µg/ml streptomycin on a glass plate. Adults were chopped with a razor blade and 2-cell embryos were picked using a mouth pipet. 30-60 2-cell embryos were transferred to a small glass boat (custom made to fit atmospheric chambers, Avalon Glass Works, Seattle Wash.) filled with 3 ml of 1% agarose in M9. Boats were then placed into a humid chamber for 2 hours to allow the embryos to age and then placed into the environmental chamber. The environmental chambers were continuously perfused at room temperature with either pure $N_2$ (grade 4.5), 100 ppm $O_2/N_2$, 500 ppm $O_2/N_2$, 1000 ppm $O_2/N_2$, or 5000 ppm $O_2/N_2$ at 70 cc/min for 24 hrs. Following exposure, agarose chunks containing the embryos were cut out of the boat and placed with embryos facing up onto a medium-sized NGM plate seeded with *E. coli* (OP50). Embryos were scored for hatching 24 hours after exposure and hatched L1's were transferred to the surface of the NGM plate and followed to adulthood. Animals that could not be accounted for were dropped from the total. All gases were supplied by Byrne Gas (Seattle, Wash.). The pure $N_2$ was guaranteed to contain less than 10 ppm impurities and all $O_2/N_2$ mixtures were certified to ±2% of the oxygen content (e.g., 100 ppm $O_2/N_2$ was certified to contain between 98 ppm $O_2$ and 102 ppm $O_2$). Parts per million to kPa conversion was based on 1 million parts=101 kPa at 1 atmosphere.

Viability of nematodes in carbon monoxide based atmospheres. 30-60 embryos were harvested from continuously maintained Bristol N2 and hif-2(ia04) strains as described above. Environmental chambers were continuously perfused at room temperature with pure CO (grade CP) or 500 ppm $O_2/CO$ at 70 cc/min for 24 hrs. To achieve 2500 ppm $O_2/CO$ or 2500 ppm $O_2/N_2$, 5000 ppm $O_2/N_2$ was mixed at a 1:1 ratio with either pure CO or pure $N_2$ using two mass flow controllers (Sierra Instruments 810) to precisely monitor flow. Each gas was delivered into a 3-way valve (Cole-Parmer #A-30600-23) at 50 cc/min and the resulting mixture was then passed through a gas washing bottle and into an environmental chamber throughout the 24 hour exposure. All gases were supplied by Byrne Gas (Seattle, Wash.). The 500 ppm $O_2/CO$ mixture was certified to 2% of the oxygen content and contained 7000 ppm $N_2$ to ensure a consistent $O_2/CO$ ratio throughout the use of the tank.

Cell biological analysis. To determine the extent of developmental progression in nitrogen-based atmospheres (Table 2), 2-cell embryos were exposed to various degrees of hypoxia as described above and were either immediately photographed, or photographed following a 12 hr recovery period in a humid chamber. To determine whether embryos arrested in carbon monoxide-based atmospheres, 2-cell embryos were aged in room air for two hours and were either photographed immediately or put into 100% carbon monoxide or 0.05 kPa $O_2/CO$ for 24 hours and photographed immediately following the exposure. In all cases, DIC microscopy was done by placing embryos under a cover slip on a thin 1% agarose pad and viewing on a Zeiss axioscope. Photographs were taken using RS Image and Adobe Photoshop software.

B. Results

Figure 2:
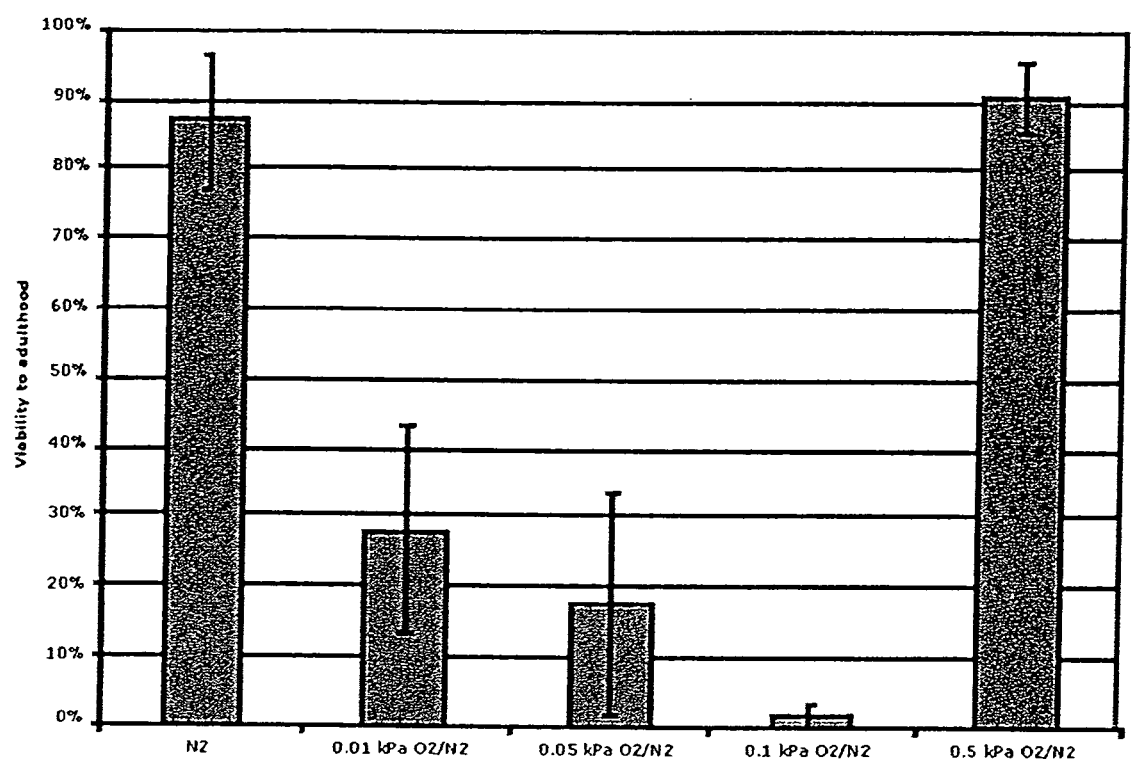
FIG. 2-Discontinuity of survivability in hypoxia. Viabilities to adulthood were assayed following exposure to 24 hours of anoxia ($N_2$), intermediate hypoxia (0.01 kPa $O_2$, 0.05 kPa $O_2$ or 0.1 kPa $O_2$) or mild hypoxia (0.5 kPa $O_2$) in wild-type embryos. All data points are the result of at least 3 independent experiments and worms that could not be accounted for were dropped from the total.

HIF-1 has been previously reported to be required in *C. elegans* in mild hypoxia (0.5 kPa $O_2$ (Padilla et al., 2002) and 1 kPa $O_2$ (Jiang et al., 2001)) and suspended animation is known to be possible in anoxia (>0.001 kPa $O_2$) (Padilla et al., 2002). To precisely define the ranges in which each of these responses are active, the viability of wild-type *C. elegans* embryos was determined following exposure to various oxygen tensions between mild hypoxia and anoxia for 24 hrs. Embryos exposed to anoxia entered suspended animation as previously reported, and thus survived the exposure with high viability. Embryos in 0.5 kPa $O_2$ remained animated throughout the exposure and also survived with high viability. However, embryos exposed to an intermediate range of oxygen tensions between mild hypoxia and anoxia (0.1 kPa $O_2$ to 0.01 kPa $O_2$) surprisingly did not survive (FIG. 2).

Embryos did not hatch during exposure to this intermediate range of hypoxia, indicating that they did not successfully execute the HIF-1 mediated response. To determine if they appeared suspended, it was examined whether embryos in this intermediate range arrested embryogenesis during the exposure. Embryos in lethal oxygen tensions did not arrest embryogenesis, and increased amounts of oxygen correlated with an increase in the extent of developmental progression in the embryo (Table 2). Upon reoxygenation, the majority of these embryos failed to hatch and many of those that did hatch arrested as abnormal L1s. These data show that this intermediate range of hypoxia is a unique stress in which oxygen levels are neither sufficiently high to facilitate continued animation nor sufficiently low to induce suspended animation.

Figure 3:
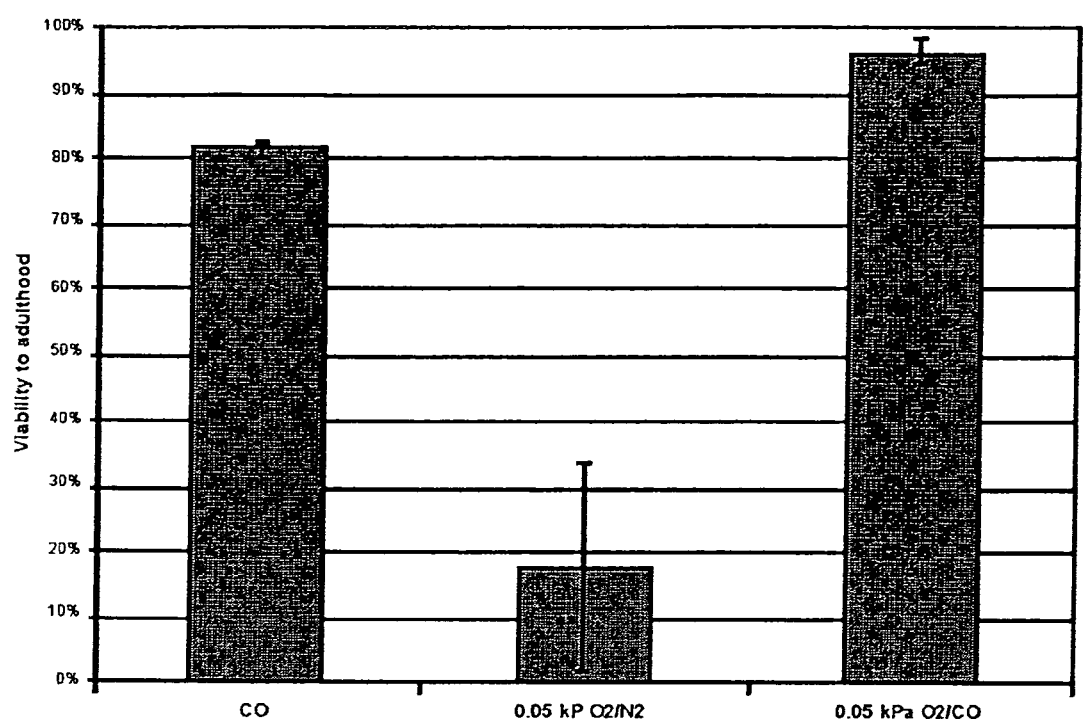
FIG. 3—Carbon monoxide protects against hypoxia. Viabilities to adulthood were assayed following exposure to 24 hours of pure carbon monoxide, 0.05 kPa $O_2/N_2$ or 0.05 kPa $O_2$/CO in wild-type embryos. All data points are the result of at least 3 independent experiments and worms that could not be accounted for were dropped from the total.

Based on these findings, it was hypothesized that if carbon monoxide, a competitive inhibitor of oxygen binding, could induce suspended animation in the presence of low levels of oxygen, it would provide protection against this lethal range of hypoxia. To examine this possibility, the viability of *C. elegans* embryos in various concentrations of carbon monoxide was first determined. Despite the toxic effects that high levels of carbon monoxide can have in some systems, *C. elegans* embryos was found to be remarkably tolerant to a wide range of carbon monoxide tensions. In fact, *C. elegans* embryos can withstand a continuous exposure to 101 kpa CO (100% CO) for 24 hrs with high viability (81.5% survival to adulthood, FIG. 3). Notably, in 101 kPa CO, embryos did not progress through embryogenesis during the exposure, indicating that they entered into suspended animation. To test whether carbon monoxide could protect embryos in the presence of lethal oxygen tensions, the viability of embryos exposed to 0.05 kPa $O_2$ balanced with carbon monoxide was determined. In contrast to embryos exposed to 0.05 kPa $O_2$ balanced with $N_2$ (most of which do not survive), these embryos recovered with 96.2% viability to adulthood (FIG. 3). Moreover, like embryos treated with 101 kPa CO, embryos in 0.05 kPa $O_2$ balanced with carbon monoxide arrested embryogenesis, indicating that they entered into suspended animation. Therefore, carbon monoxide can protect against hypoxic damage in the presence of lethal oxygen tensions by inducing suspended animation.

To further examine the range of oxygen tensions that can be protected by excess carbon monoxide, embryos lacking HIF-1 function (the hif-1(ia04) strain) were used to address whether protection against hypoxic damage was also possible in mild hypoxia. After testing various oxygen tensions between 0.1 kPa $O_2$ and 1 kPa $O_2$ balanced with nitrogen, it was found that the maximal requirement for HIF-1 was in 0.25 kPa $O_2$ balanced with nitrogen. In this atmosphere, wild-type embryos progress normally through development and exhibit high viability, but hif-1(ia04) embryos do not complete embryogenesis and exhibit 100% lethality (Table 3). Therefore, it was examined whether carbon monoxide could protect hif-1(ia04) embryos in 0.25 kPa $O_2$. In 0.25 kPa $O_2$ balanced with carbon monoxide, both wild-type and hif-1 (ia04) embryos entered into suspended animation and survived the exposure with high viabilities (78.7% and 84.0% survival to adulthood, respectively) (Table 3). Thus, the induction of suspended animation by carbon monoxide is possible at oxygen tensions as high as 0.25 kPa $O_2$, and carbon monoxide can protect against mild hypoxia, even in the absence of HIF-1 function.

TABLE 2

Quantitation of developmental progression in hypoxia

| Atmosphere | Percent of embryos within range | Range of embryogenesis (min post 2-cell stage) | N |
|---|---|---|---|
| >0.001 kPa $O_2/N_2$ | 100% ± 0.0 | 20-40 min | 35 |
| 0.01 kPa $O_2/N_2$ | 92.9% ± 6.0 | 40-80 min | 115 |
| 0.05 kPa $O_2/N_2$ | 97.7% ± 2.0 | 100-140 min | 108 |
| 0.1 kPa $O_2/N_2$ | 91.4% ± 1.3 | 300-340 min | 60 |

Wild-type 2-cell embryos were placed into various degrees of hypoxia for 24 hrs and scored for the extent to which they progressed through embryogenesis. Exposure to atmospheres containing increased amounts of oxygen resulted in increased progression through embryogenesis. The percent of embryos that arrested within a given 20-40 minute range of embryogenesis was determined. Data are the result of 3 independent experiments.

TABLE 3

Carbon monoxide protects hif-1 embryos against mild hypoxia

| | 0.25 kPa $O_2/N_2$ | n | 0.25 kPa $O_2$/CO | N |
|---|---|---|---|---|
| N2 | 94.2% ± 1.2 | 49 | 78.7% ± 21.9 | 109 |
| hif-1(ia04) | 0.0% ± 0.0 | 68 | 83.9% ± 13.8 | 108 |

Viabilities to adulthood were assayed following exposure to 24 hrs of 0.25 kPa $O_2/N_2$ or 0.25 kPa $O_2$/CO in wild-type and hif-1(ia04) embryos. All data points are the result of at least 3 independent experiments and worms that could not be accounted for were dropped from the total.

Viability of Nematodes in Response to Hypothermia.

Figure 15:
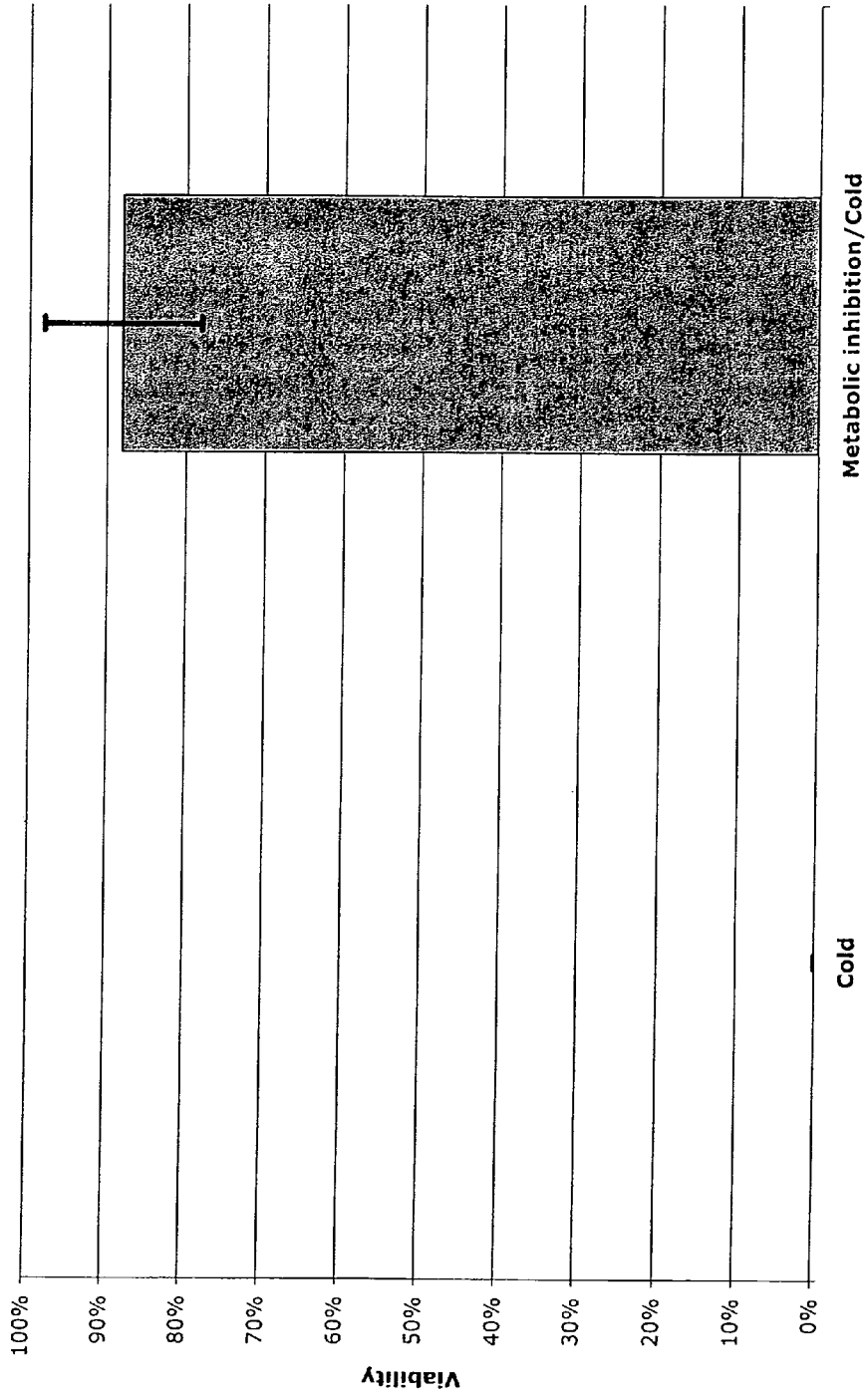
FIG. 15 Metabolic inhibition protects against hypothermia-induced death in Nematodes. Nematodes exposed to cold temperatures (4° C.) are unable to survive after 24 hours. However, if kept in anoxic conditions during the period of hypothermia (and for a 1 hour period before and after), a substantial proportion of the nematodes survive.

Viability of nematodes is also temperature sensitive, with 100% of a population being dead after a 24 hr exposure to cold temperature (4° C.; FIG. 15). However, if the nematodes are induced into stasis by equilibration into anoxic conditions (<10 ppm oxygen) for 1 hr prior to the temperature drop, a substantial proportion of them survive after a 24 hr exposure to 4° C. (FIG. 15). In this experiment, the nematodes were kept in stasis during the period of hypothermia, and for one hour after they have been returned to room temperature. Anoxic conditions (pure $N_2$), growth conditions, and viability measurements are described below.

Example 4

Reduction of Core Body Temperature and Respiration in Mice

A. Materials and Methods

Implantation of telemetry devices. Female C57BL/6J mice (Jackson Laboratories—Bar Harbor, Me.) were implanted with telemetry devices (PDT-4000 HR E-Mitter—MiniMitter Inc.—Bend, Oreg.) according to standard protocol provided by the manufacturer. Mice were allowed to recover for several weeks to permit body temperature and heart rate signals to stabilize. Core body temperature, heart rate, and movement of the mice were continuously monitored via the telemetry devices and recorded using VitalView software (provided by MiniMitter). Ambient temperature was monitored using a HOBO (Onset Computer Corp.—Pocasset, Mass.) and the data analyzed using BoxCar software (provided by Onset Computer Corp.).

Exposure of Mice to Regulated Atmosphere. Each mouse was exposed to 1 L/min of either (a) an atmosphere containing 500 ppm $H_2S$ balanced nitrogen (Byrne Specialty Gas—Seattle, Wash.) mixed with room air (using a 3 channel gas proportioner meter from Aalborg—Orangeburg, N.Y.) to give a final concentration of 80 ppm $H_2S$ and 17% $O_2$, or (b) an atmosphere of nitrogen mixed with room air to give a final concentration of 17% $O_2$. $H_2S$ and $O_2$ measurements were taken using an Innova GasTech GT series portable gas monitor (Thermo Gas Tech—Newark, Calif.).

Prior to and during exposure to testing in regulated and unregulated atmospheres, the mice were placed in a gassing chamber comprising a glass cage (with drinking water and no food) fitted with import and export tubes of FEP tubing from Cole-Parmer (Vernon Hills, Ill.) for introduction and venting of the atmosphere. The cage was sealed with a lid using Dow Corning silicone vacuum grease (Sigma—St. Louis, Mo.). The gas from each cage was vented through the export tube into the chemical hood. To ensure that the system was gas-tight, a GasTech GT portable monitor was used to detect leaks.

Respirometry. In some experiments, the consumption of oxygen was measured by use of a PA-10a $O_2$ analyzer (Sable Systems) which was used according to manufacturers instructions. Similarly, the carbon dioxide being produced by the animals was monitored using a LI-7000 $CO_2/H_2O$ analyzer (Li-Cor company) used according to the manufacturers instructions. These instruments were placed in line with the environmental chambers such that they sample the gas import and export tubing.

Regulation of Ambient Temperature. Mice were housed in a Shel Lab low temperature diurnal illumination incubator (Sheldon Manufacturing Inc.—Cornelius, Oreg.) to regulate both temperature and light cycle (8 AM lights on, 8 PM lights off) for the mice. Mice were exposed to regulated atmosphere as described above. When the mice were exposed to the regulated atmosphere, the temperature inside the incubator was dropped to the desired temperature, for example, to 10° C. or 15° C. The mice were maintained in the regulated atmosphere and at the lowered temperature for six hours. The atmosphere in the gassing chamber was replaced with room air and the the mice were returned to normal room temperature (22° C.) and allowed to recover.

B. Results

Baseline Data. To determine the response of mice to sublethal doses of hydrogen sulfide, the inventor first established baselines of core temperature, heart rate and movement by recording data over a one-week period from four mice with implanted transceivers in the incubator held at ambient temperature and perfused with room air. The baseline data demonstrated that the mice have a circadian rhythm with peak of activity in the evening just after the lights are turned off, and in the early morning just before the lights are turned on. The core temperature varied from a high of 37° C. during their active periods to a low of 33.5° C. during their inactive periods. The heart rate varied from 750 bpm (beats per minute) during their active periods to 250 bpm during their inactive periods. Heart rate is likely to be correlated with core temperature (higher temp higher heart rate). Likewise gross motor movement was highest during the evening and just before dawn.

Exposure of Mice to Regulated Atmospheres at Room Temperature. The first trial of the exposure of a mouse to hydrogen sulfide involved first placing the mouse into the gassing chamber held at 27° C. in the incubator for one hour. After the hour, the chamber was perfused with 80 ppm as generally described above and the temperature of the incubator was lowered to 18° C. for the duration of the experiment. While no immediate changes in heart rate and gross motor movement were detected, a dramatic decrease in core temperature was observed. The experiment was allowed to proceed for 90 min. during which time the core temperature dropped to 28.6° C.—five degrees below the lowest recording for any of the four mice in the baseline study described above. During recovery after the chamber was perfused with room air, the inventor noticed that the animal at first was relatively immobile (easy to catch); however within 60 min. it had returned to a normal range of core temperature and activity. A second mouse was exposed to the same protocol; however this time the gassing at 80 ppm was conducted for 3 hrs. During this time, the inventor noted that heart rate dropped significantly from 600 bpm to 250 bpm, gross motor movement showed almost no activity, and the core temperature dropped to 18.6° C.

Figure 4A:
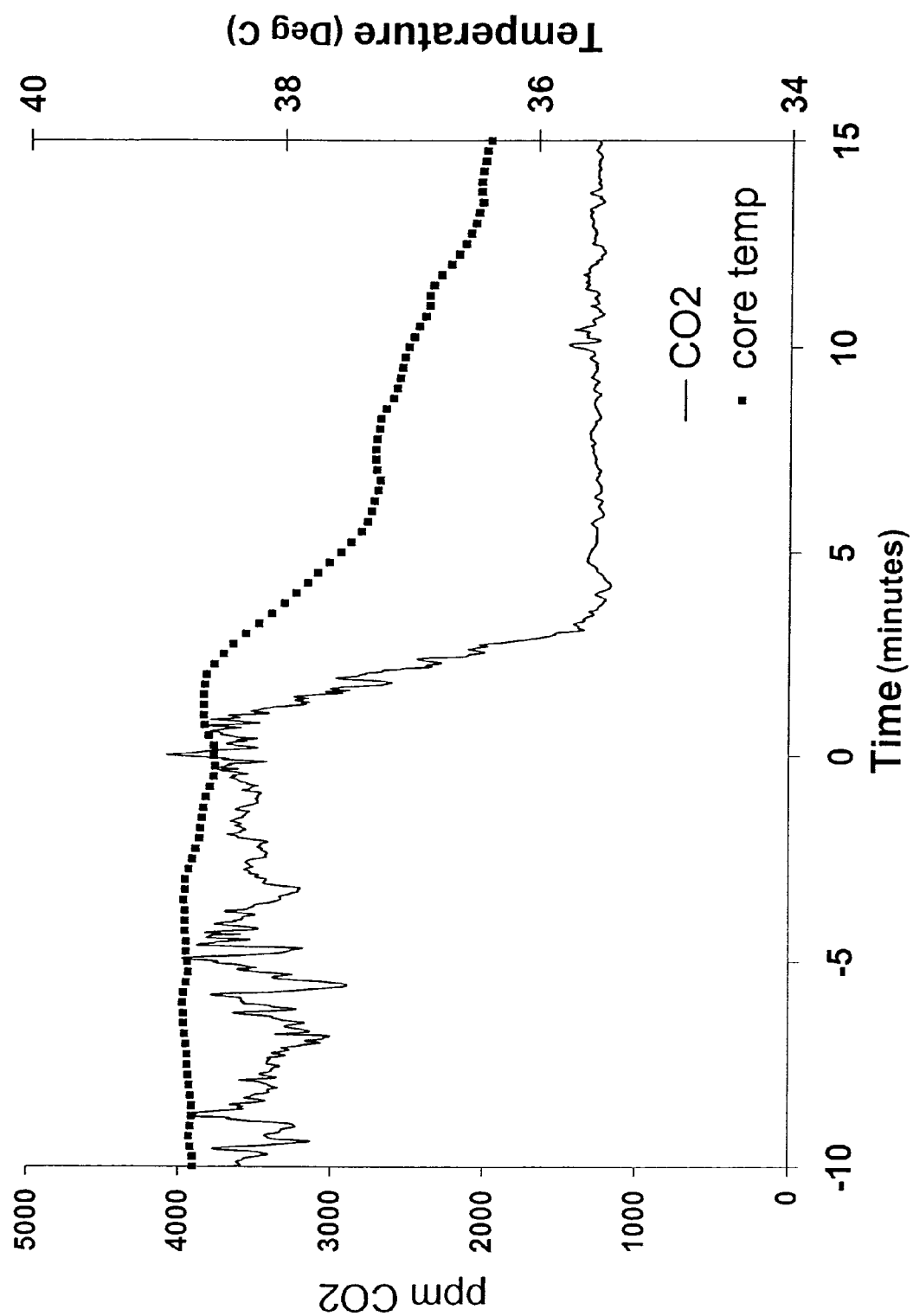
FIG. 4A—Metabolic rate decreases before body core temperature when mice are exposed to hydrogen sulfide. Exposure of mice to 80 ppm (at 0 minutes on the X axis) results in an approximately 3 fold decrease in $CO_2$ production (black line) in less than five minutes. This precedes the drop in core temperature of the animal toward the ambient temperature (gray line).

Changes in respiration accompany the drop in core temperature. Exposure of the mice to 80 ppm $H_2S$ results in decreased metabolic rate as well, as determined by measuring oxygen consumption and carbon dioxide production. For example, a mouse that had core temperature and carbon dioxide production measured simultaneously, demonstrated a rapid reduction in carbon dioxide production preceding the drop in core temperature of the animal (FIG. 4A). The approximately three-fold reduction in carbon dioxide production established a new baseline in approximately 5 minutes after the exposure to $H_2S$.

Table 4 shows results from an experiment with concurrent measurements of $O_2$ and $CO_2$ concentrations from mice exposed to room air that had had the $CO_2$ scrubbed (hence the 0 values for controls), with or without $H_2S$ (80 ppm). Measurements were over a period of 15 minutes, with the mice in a 0.5 L sealed environmental chamber with flow rates of 500 cc/min. Consumption of oxygen is obtained by subtracting the oxygen concentration when the mouse is present, from the control when the mouse is absent. Likewise, production of carbon dioxide is obtained by subtracting the carbon dioxide concentration when the mouse is present from the control when the mouse is absent. RQ stands for respiratory quotient, and is equal to the ratio of carbon dioxide produced to oxygen produced. This result demonstrates, a 2-3 fold drop in oxygen consumption in the presence of $H_2S$, as well as a 3-4 fold drop in carbon dioxide production. The change in the respiratory quotient reflects the disparity oxygen consumption and carbon dioxide production by the mice in the presence or absence of the $H_2S$.

TABLE 4

$H_2S$ exposure inhibits respiration in mice.

| Mouse present | $H_2S$ present | $[O_2]$ ppm | $[CO_2]$ ppm | RQ |
|---|---|---|---|---|
| − | − | 207,000 | 0 | |
| + | − | 203,600 | 2800 | |
| | Consumption, production | 3,400 | 2800 | 0.82 |
| − | + | 166,200 | 0 | |
| + | + | 164,900 | 750 | |
| | Consumption, production | 1300 | 750 | 0.58 |

The different parameters of stasis (reduction in oxygen consumption, decrease in carbon dioxide production or decrease in motility) can be assessed by a variety of assays and techniques. For example, probably the easiest way to measure the induction of stasis in mice administered $H_2S$ is through observation of their breathing. Indeed, this encompasses all three parameters in that it is indicative of decreased oxygen consumption, carbon dioxide production and motility. A normal mouse in room air at standard conditions will take approximately 200 breaths per minute. If $H_2S$ is administered to the mouse at 80 ppm, and the core temperature is dropped to 15° C., breathing is decreased at least an order of magnitude to somewhere between 1-10 breaths per minute. In fact, a mouse was observed under these conditions that did not take a breath for a period greater than an hour, indicating that deep levels of stasis are attainable. Thus, this represents at least about a 1-20-fold decrease in cellular respiration (i.e, oxygen consumption and carbon dioxide production).

Exposure of Mice to Regulated Atmospheres at Reduced Ambient Temperatures. To begin to define the limits of the capacity for hydrogen sulfide to reduce the activity in mice, the inventor conducted several experiments in which a non-telemetry mouse was used, followed by exposure of a mouse bearing telemetry to acquire the data. The first experiment was to subject a non-telemetry mouse to a regulated atmosphere of $H_2S$ at 80 ppm in a reduced cabinet temperature of 10° C. essentially as described in Materials and Methods were as above except that the mouse was placed in the gassing chamber for one hour at 27° C. prior to exposure to the gas and reduction in ambient temperature. The non-telemetry mouse did well in this treatment, and recovered activity within approximately 90 min. after removal from the gassing chamber. The telemetry mouse was subjected to the same conditions also did well, and showed decreased core temperature to approximately 12.5° C. The inventor was unable to accurately determine this temperature because the electronics failed at 15.3° C. The temperature drop to 12.5° C. is therefore an estimation based on the slope of the drop prior to failure and the time the animal remained in the chamber after failure of the electronics.

Figure 4B:
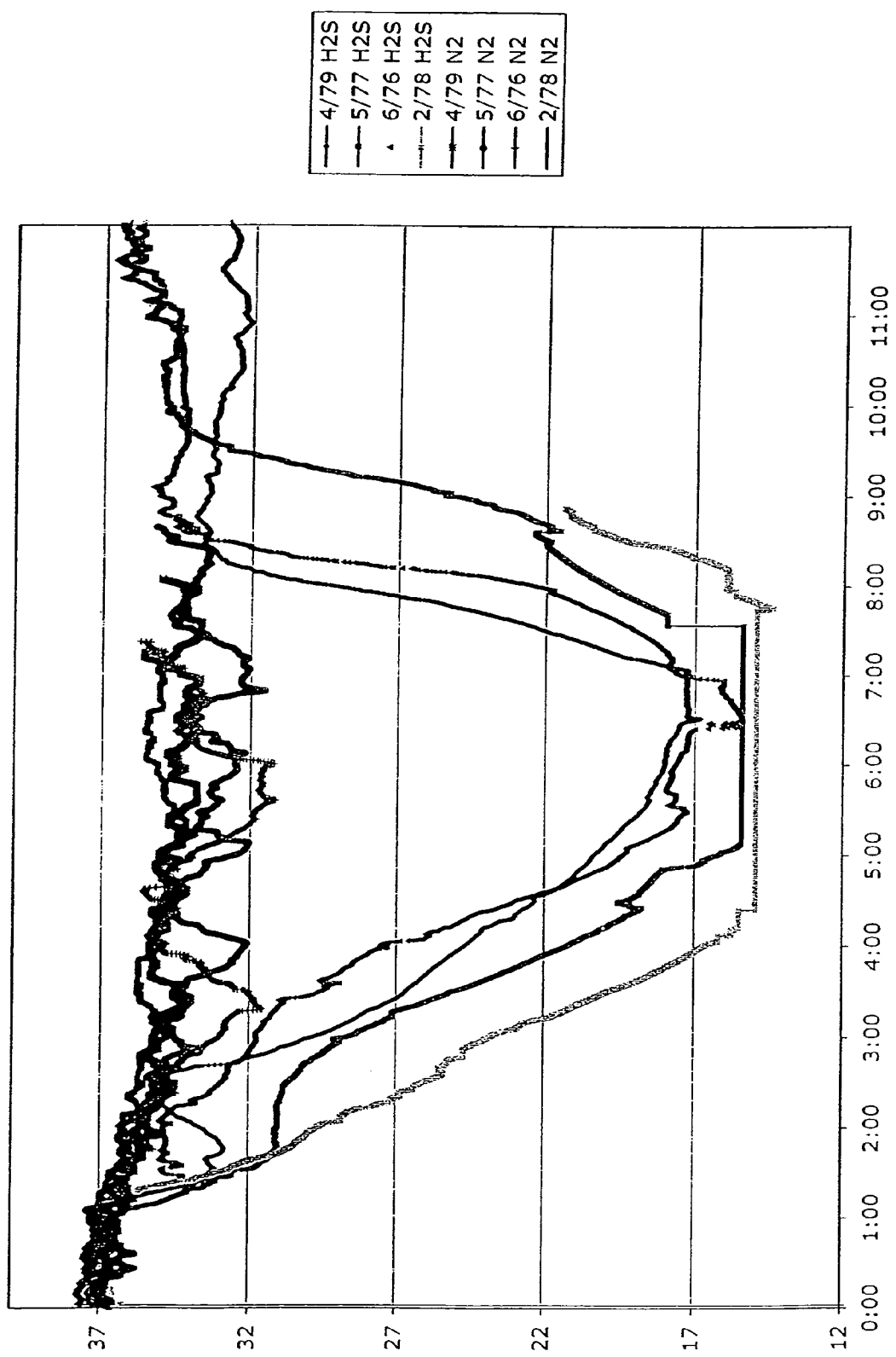
FIG. 4B—Temperature of mice exposed to hydrogen sulfide. Each trace represents a continuous measurement of core body temperature individual mouse exposed to either 80 ppm of $H_2S$, or to room air. Numbers on the vertical axis are temperature in ° Celsius. On the horizontal axis, the numbers reflect time in hours. The experiments were carried out for 6 hours followed by recordings of the recovery. The beginning point is at 1:00, and the end of the 6 hr treatment is about 7:00.

Because of the limitation of the equipment, the inventor next tested each of the four telemetry mice for a 6 hr period in the gassing chamber with a regulated atmosphere containing approximately 80 ppm hydrogen sulfide or with room air essentially as described above. The temperature of the incubator was reduced at initiation of the experiment (exposure to the regulated atmosphere, or time 0 for the mice exposed to room air) to a constant 15° C. At the end of the six-hour period, the mice were returned to an atmosphere of room air and an ambient temperature of 22° C. as generally described above. There was a clear decrease in core body temperature in all four mice that was dependent on the use of 80 ppm hydrogen sulfide (FIG. 4B). There was also a marked drop in heart rate and gross motor movement associated with the decrease in temperature. The mice were maintained for 4 weeks with no apparent change in the behavior of the animals.

Example 5

Murine Studies on Reduction of Radiation Injury

A. Scientific Rationale

While aspects of the radiation injury model can and have been evaluated in cell culture, to test the ability of an experimental drug to affect the injury and healing process requires inclusion of all of the response systems that are affected. At this point in time, the only way to achieve that is in a whole animal. The inventor is proposing the use of mice for such studies as the most appropriate model. The C57BL/6 mice have been selected for study because this strain of mouse is readily susceptible to radiation lung injury, the level of radiation that is tolerated in this strain has been established, and the inventor has recently shown that $H_2S$ decreases the core temperature of this mouse strain.

Two identical experiments are planned under this protocol. Each experiment will investigate the efficacy of $H_2S$-induced hypothermia on the development of radiation induced lung injury. Ten mice per group will be exposed to one of four test conditions ($H_2S$/17.5 Gy thoracic irradiation, $H_2S$/no thoracic irradiation, no $H_2S$/17.5 Gy thoracic irradiation, or no $H_2S$/no thoracic irradiation), then followed for 13 weeks. Twelve animals per group will be similarly exposed and followed for 26 weeks (the increased n is required to compensate for the increased mortality that occurs late in the course of the disease).

For these experiments, analysis of variance (ANOVA) will be used as the statistical model for data analysis. A completely crossed and randomized two factor ANOVA with 4 groups (irradiated or non-irradiated mice receiving $H_2S$ or not receiving $H_2S$) and two time intervals (13 or 26 weeks) will be used to analyze temporal changes in bronchoalveolar lavage inflammatory cell number and total protein concentration and lung hydroxyproline levels. Assuming 80% power, 5% significance and a two-tailed test, five surviving mice per combination of injury group, intervention group and time point will allow a detectable difference among group means greater than or equal to 1.7 times the underlying within-group standard deviation. The within-group standard deviation is expected to be equal to about 25%. Thus, changes in inflammatory cell numbers or lung collagen content of 35-50% of control values should be discernable in these experiments.

$H_2S$ exposure and thoracic irradiation will be done in SLU AHR in a linear accelerator suite. Bronchoalveolar lavage and lung procurement at necropsy will be performed in the AHR mouse necropsy room. Bronchoalveolar lavage cell counts and protein concentrations and lung hydroxyproline content measurements will be performed in the another lab (D3-255). Wild genotype C57BL/6 mice will receive 17.5 Gy of thoracic irradiation. Mice will be anesthetized with intraperitoneal Avertin, placed into individual cloth mouse restrains and irradiated via the linear accelerator with 8.5 Gy at a dose rate of 3 Gy/min through two lateral fields collimated to target the thorax only (total thoracic dose 17.5 Gy).

B. Protocol

Anesthesia. Wild genotype C57BL/6 mice will be anesthetized for intratracheal dosing with Isoflurane. The depth of anesthesia will be monitored by respiratory rate for response to tactile stimulation. Intraperitoneal injection of Avertin (0.4-0.7 ml/mouse i.p.) will be used to anesthetize animals for the thoracic irradiation procedure. The depth of anesthesia will be monitored by respiratory rate and response to tactile stimulation.

Exposure to hydrogen sulfide. Mice will be placed into a closed plexiglass gassing chamber similar to the one used previously for mice (IR1606). The chamber will have two ports (import and export). A gas containing H2S (80 ppm) balanced with room air will be vented through the chamber at a rate of 1 liter per minute. The gas will be vented from the room using the house ventilation system with a hose that extends from the export vent to the exhaust vent for the room.

Hazardous agent administration. Mice will be irradiated while they are in the gassing chamber with a total dose of 17.5 Gray using the linear accelerator. This radiation dose will induce an subacute pulmonary injury in the mice which progresses to fibrosis. The mice will not be radioactive or otherwise provide a hazard to personnel or other animals. No special monitoring, containment or disposal is required due to the irradiation.

Scheduled euthanasia. At approximately weeks 13 and 26 after thoracic irradiation, the animals will be euthanized by deep anesthesia (using avertin 0.4-0.7 ml i.p.) followed by exsanguination via inferior vena cava puncture. Bronchoalveolar lavage will be performed to determine inflammatory cell number, differential counts and lavage fluid protein concentrations. Lung and esophagus tissue will be removed for histologic evaluation and collagen content analysis.

Moribund animals. Thoracic radiation is associated with a finite mortality rate in mice, with 15% dying by week 10 and 50% by week 22 post irradiation. The investigators will monitor the animals daily for adverse effects (2-3 times per day initially, until they appear stable, then once daily until disease begins to progress, at which point the inventor will return to multiple daily observations). If an animal is losing weight, failing to groom, exhibiting severe respiratory distress, and/or awkward or significantly diminished movement, it will be euthanized with an avertin overdose. When practical, bronchoalveolar lavage and tissue collection for histology will be performed for these unscheduled euthanasias.

Thoracic irradiation should produce a lung injury which itself is not painful but may manifest itself (week 10) by increased respiratory rate, mild appetite loss, mild weight loss and/or failure to groom. The investigators and animal facility staff will monitor the animals daily for such adverse effects. If an animal does not seem to be eating, soft food and fluid support will be provided. If the animal is perceived to be in pain, analgesia with Butorphanol (0.2 mg/kg i.p.) or Buphrenorphine (1.0 mg/kg bid s.q.) will be administered as needed. If an animal appears to be suffering and palliative measures do not lead to improvement, it will be euthanized immediately. Lung and esophagus tissue will be collected for histopathologic evaluation and collagen content analysis at the scheduled necropsies.

Post-irradiation Husbandry. To minimize the risk of transmitting any pathogens to the rest of the facility, and to protect these animals while they are somewhat immunocompromised, all husbandry work on these animals will be done first thing each day (before any other animals in the facility) and will be done in a biosafety cabinet. To minimize the risk of adventitious infections, the mice will have autoclaved cages and bedding. In addition, they will be fed standard rodent food that has been irradiated to kill pathogens.

Wild genotype C57BL/6 mice will receive 17.5 Gy of thoracic irradiation. Mice will be anesthetized with intraperitoneal Avertin, placed into individual cloth mouse restraints and moved into a closed plexiglass gassing chamber similar to the one used previously for mice (IR1606). The chamber will have two ports (import and export). A gas containing H2S (80 ppm) balanced with room air will be vented through the chamber at a rate of 1 liter per minute. The gas will be vented from the room using the house ventilation system with a hose that extends from the export vent to the exhaust vent for the room. Once in the gassing chamber the mice will be irradiated via the linear accelerator with 8.5 Gy at a dose rate of 3 Gy/min through two lateral fields collimated to target the thorax only (total thoracic dose 17.5 Gy). After completion of thoracic irradiation the animals will be returned to their micro-isolater cages monitored until recovered from anesthesia.

Scheduled necropsises. One set of animals will be necropsied in week 13 post-irradiation to evaluate the inflammatory phase of the injury. The second set will be euthanized in week 26 to evaluate the fibrotic phase of the injury. Animals will be anesthetized with avertin, then exsanguinated. The lungs will be lavaged with 1000 ul PBS and the lavage fluid kept on ice for total and differential cell counts. The right lung will then be harvested for hydroxyproline content and the left lung will be infused with 10% NBF at 25-30 cm pressure through the trachea. The esophagus, trachea, left lung and heart will be immersed in 10% NBF and set to the FHCRC histology shared resource lab for processing and pathology evaluation.

Thoracic irradiation should produce a lung injury which itself is not painful but may manifest itself (week 10) by increased respiratory rate, mild appetite loss, mild weight loss and/or failure to groom. The investigators and animal facility staff will monitor the animals daily for such adverse effects. If an animal does not seem to be eating, soft food and fluid support will be provided. If the animal is perceived to be in pain, analgesia with Batorphanol (0.2 mg/kg i.p.) or Buphrenorphine (1.0 mg/kg bid s.q.) will be administered as needed. If an animal appears to be suffering and palliative measures don't lead to improvement, it will be euthanized immediately by $CO_2$ asphyxiation.

The primary problems are likely to be esophagitis (resulting in decreased food and water intake) and respiratory insufficiency (reducing oxygen uptake). The inventor will be checking these animals 2-3 times per day until they are convinced that they are stable and doing well, at which point the inventor may reduce the frequency of checks to once daily, until the disease begins to progress, at which point they return to multiple daily checks. Supportive care will be provided in several ways. If an animal is not eating or drinking well (evidenced by weight loss and grooming problems), the inventor will provide soft food and try fluid supplementation (Lactated Ringer's solution, 1-2 ml/mouse, sc using a small bore needle (>20 G), 1-2 times daily). If the animal is perceived to be in pain, analgesia with Batorphanol (0.2 mg/kg i.p.) or Buphrenorphine (1.0 mg/kg bid s.q.) will be administered as needed. If an animal appears to be suffering and palliative measures do not lead to improvement, it will be euthanized immediately by $CO_2$ asphyxiation. In the event that an animal experiences significant pain or distress at the time of thoracic irradiation, the animal will be euthanized by $CO_2$ asphyxiation.

A third experiment was to subject a telemetry mouse to a regulated atmosphere of $H_2S$ at 80 ppm in a reduced cabinet temperature of 10.5° C. essentially as described above. During the experiment, the mouse was visually observed and its movements were recorded by web camera, and telemetry measurements were recorded as described above. The mouse was exposed to a regulated atmosphere of 80 ppm $H_2S$, and the temperature of the cabinet was reduced to a constant 10.5° C. At the end of an approximately six-hour period, heat was applied to the cabinet by setting the cabinet temperature to 25° C. The mouse was allowed to warm up in the regulated $H_2S$ atmosphere until the core temperature of the mouse was between 17° C. and 18° C. after which time the regulated atmosphere was replaced with room air. There was a clear decrease in core body temperature of the mouse to 10.5° C. in the regulated atmosphere accompanied by a marked drop gross motor movement. The respiration rate dropped to an undetectable rate by visual observation for approximately one hour and fifteen minutes. After the cabinet was warmed, weak respiration was observed when the core body temperature of the mouse achieved 14° C. During the warming phase, when the core body temperature rose to between 17° C. and 18° C., and the mouse was exhibiting respiration and movement, the regulated atmosphere was replaced with room air. Normal movement and respiration were fully apparent when the core body temperature returned to 25° C. The mouse has exhibited no apparent change in the behavior compared to animals that were untreated.

Example 6

Cell and Mammal Studies

A. Canine Studies

Canine studies will be conducted with dogs surgically implanted with telemetry devices to monitor their core body temperature. The animals will be studied in the presence or absence of a sub-lethal dose of hydrogen sulfide for 10 hrs. During this time, they will be continuously monitored for vital signs by telemetry. The temperature of the environment will also be reduced to 15° C. for 30 min to determine whether this has any effect on the core body temperature of the animals.

The procedure will be conducted with 2 groups of 2 dogs (four total). Because of the expense of the telemetry equipment the inventor will do these experiments in succession. If the results from the first group indicate that the hypothesis is incorrect, the study will be repeated with the second group of two dogs. If the results from the second group do not support the hypothesis, the project will be discontinued.

Toxicology studies demonstrate that, while the level of $H_2S$ is above the OSHA limit for humans (10 ppm), it has been shown previously that exposure of both rats and mice to 80 ppm of $H_2S$ for 6 hrs per day, 5 days per week, for 90 days, showed no observed adverse effect. This included both gross and histopathological examination of the gut, lung, heart, liver, kidneys, or other organs conducted at the end of the treatment. To the inventor's knowledge, no information is available concerning exposure of dogs to hydrogen sulfide.

A critical issue in working with H₂S is to not exceed the dose (80 ppm) described by others who have published studies on rodents exposed to hydrogen sulfide and not seen detrimental effects. There is considerable experience in gas sciences available, and the inventor is capable of delivering the gas to the mice at the prescribed dose. Many precautions are taken to ensure that both animals and investigators are not harmed. These precautions include constant monitoring of the gas mixture with alarm set to OSHA limits and sensitivity to 1 ppm, and a variety of equipment that is able to mix and deliver the gas according to specifications without leakage into or out of the system.

A time line for the protocol is given in Table 5.

TABLE 5

Study Time Line

| Day | Activity | Detail |
|---|---|---|
| −1 | Pre-surgery | A CBC/Chemistry will be performed; dog will be fasted in p.m., but allowed free access to water. |
| 0 | Surgery | Fentanyl transdermal patch placed p.m. of day before surgery for preemptive analgesia. Preoperative placement of cephalic catheter; premedication with Acepromazine, Buprenorphine, Glycopyrrolate; induction with either Ketamine: Diazepam or Propofol to permit intubation; maintenance anesthesia by isoflurane and oxygen. Dog will be placed in dorsal recumbancy and the abdomen clipped/prepped and draped. Monitoring of pulse, respiration rates, end-tidal carbone dioxide, inhaled percentage of anesthetic agent, SpO₂ will be performed and recorded every 15 minutes or more frequently. Fluid support during and after surgery will occur. Once the dog is stable and appropriately prepared for the procedure, a ventral midline laparotomy, beginning caudal to the umbilicus and extending 5-10 cm caudally, will be performed. A sterile transmitter will be placed into the peritoneal cavity. Placement will be checked to insure that the transmitter is able to move freely; the omentum will be replaced, and closure of the peritoneal cavity will be performed in 3 layers. The dog will be monitored until it is extubated, is able to thermoregulate and is sternally recumbent. Daily monitoring of the dog's incision site, abdomen (via palpation and ultrasound, if indicated), appetite, temperature (for the first 3-5 post-operative days), weight and activity will be performed. |
| 7 | Establishment of Baselines | This date is flexible. Will only proceed with this step with approval. Four animals will be placed onto the receiver equipment (this does not involve removal of the animals from their cages and will occur in AHR) and baselines for the vital signs will be established for all four animals. |
| 8 | Exposure to H₂S | Animals will be transferred to a room to be determined where they will be placed into caging with food and water that has an enclosed atmosphere. After establishing baselines two of the four animals will be subjected to H₂S at a concentration of 80 ppm. Following a ten-hour exposure, the atmosphere will be returned to room air temperature and the animals will be returned to their cages. Exposure to H₂S will repeated once per week to begin to determine whether any data set is reproducible. |

B. Human Platelets

To test the concept that using inhibitors of oxidative phosphorylation could be used for human benefit, the inventor induced a state of suspended animation in human tissues to protect them from lethal exposure to oxygen. In pilot experiments, the inventor placed human skin in an environment of 100% CO. The inventor observes that after 24 hrs skin cells survive 100-fold better in CO than those in room air. These results are very exciting; they provide evidence that inhibitors of oxidative phosphorylation can be effective in human tissues.

Another set of experiments demonstrates the protective effects of induced suspended animation on platelets. A unit of platelets was split in half. The first half was kept at standard storage conditions, which involves keeping the platelets at room temperature (22-25° C.) with constant shaking. The other half was placed inside an anoxic environment (<10 ppm oxygen) using standard methods to remove the oxygen. The two sets of platelets were compared on days 0, 5 and 8. The platelets kept in anoxic conditions performed as well or better than those kept at standard conditions over a panel of five different in vitro tests, including the ability to aggregate, cell morphology, Annexin-V staining (phosphatidyl-serine flipping to the outer membrane as an early apoptotic marker), and so on. This indicates that controlling metabolic activity, specificially oxidative phosphorylation, can be accomplished by the removal of oxygen and has a protective effect on cellular function over long periods of stasis.

Hydrogen sulfide is able to bind cytochrome C oxidase as well as CO and stop oxidative phosphorylation on demand. It is so potent at impeding oxidative phosphorylation, that should a person take a single breath in an atmosphere with 0.1% hydrogen sulfide, they will not take another. Instead, they immediately collapse to the floor—an event commonly referred to in industrial settings as a "knock down." It also appears to be reversible because, if rapidly removed to fresh air (and uninjured from the fall) these individuals can sometimes reanimate and go on to live without neurological problems. Here is an agent that is not only common in our world, indeed, is produced even in our own cells, but is also a potent reversible inhibitor of oxidative phosphorylation that does not effect oxygen delivery.

C. Murine Studies

Induction of a Hibernation-Like State Using $H_2S$. Homeothermic animals, by definition, maintain a core body temperature 10-30° C. above the ambient temperature. For these animals to do this, they must generate heat from the energy produced by oxidative phosphorylation. The terminal enzyme complex in oxidative phosphorylation is cytochrome c oxidase. Since hydrogen sulfide inhibits this complex (Petersen, 1977; Khan et al., 1990), the inventor predicts that exposing a homeothermic animal to hydrogen sulfide will prevent such an animal from maintaining its core body temperature well above ambient temperatures.

To test this hypothesis, the inventor wanted to continuously monitor both the core body temperature and the activity levels of a homeothermic animal (a mouse). Telemetry devices, implanted into the peritonea of mice, can do both of these things and have the advantage of not introducing bias to the readings due to the handling of the mice (Briese, 1998). Additionally, they can remotely monitor the mice during the exposure to the hydrogen sulfide gas. A dose of 80 parts per million (ppm) hydrogen sulfide has been previously shown to be innocuous to mice for exposures lasting up to ten weeks (CIIT 1983; Hays, 1972). Therefore, for these experiments the inventor used a dose of 80 ppm hydrogen sulfide to test our hypothesis. Creating an atmosphere containing 80 ppm of hydrogen sulfide is not trivial. Over time, in the presence of oxygen, hydrogen sulfide will be oxidized to sulfate. For that reason, in order for the inventor to continuously expose a mouse to an atmosphere containing 80 ppm hydrogen sulfide, the inventor constantly mixes room air with a tank of 500 ppm hydrogen sulfide balanced nitrogen.

Characterization of Core Temperature Control

Figure 5A:
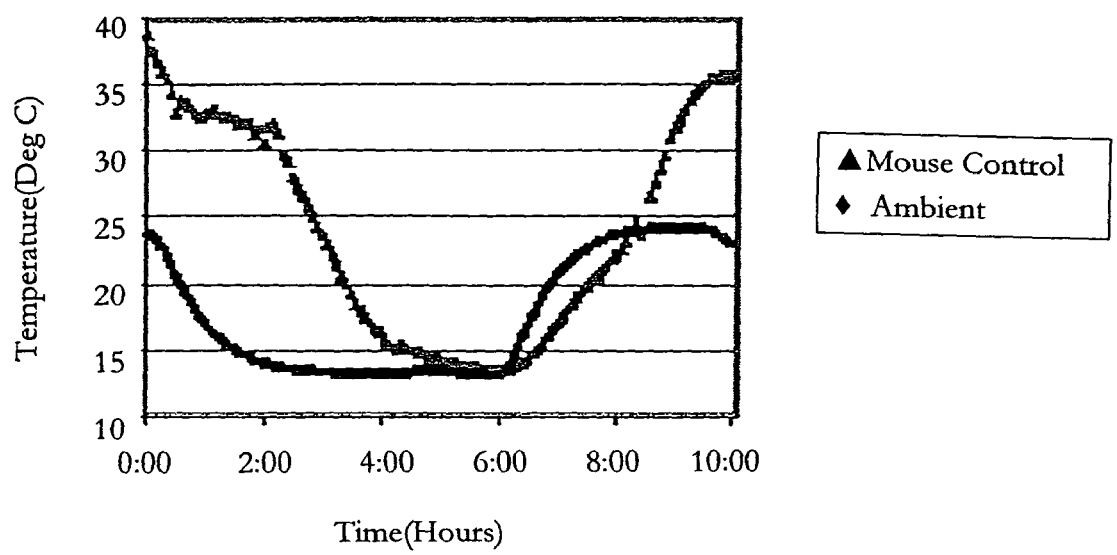
FIG. 5A—Exposure to 80 ppm hydrogen sulfide causes the core body temperature of a mouse to approach ambient temperature. Gas was turned on and temperature decreased starting at time 0:00. Atmosphere switched back to room air at time 6:00. Triangles indicate the core body temperature of the mouse as determined by radiotelemetry. This was approximately 39° C. at time 0:00. Diamonds indicate the ambient temperature which was reduced from 23° C. to 13° C. in the first 3 hours of the experiment, and then increased again toward 23° C. from hour 6:00 stabilizing at around hour 9:00.
Figure 5B:
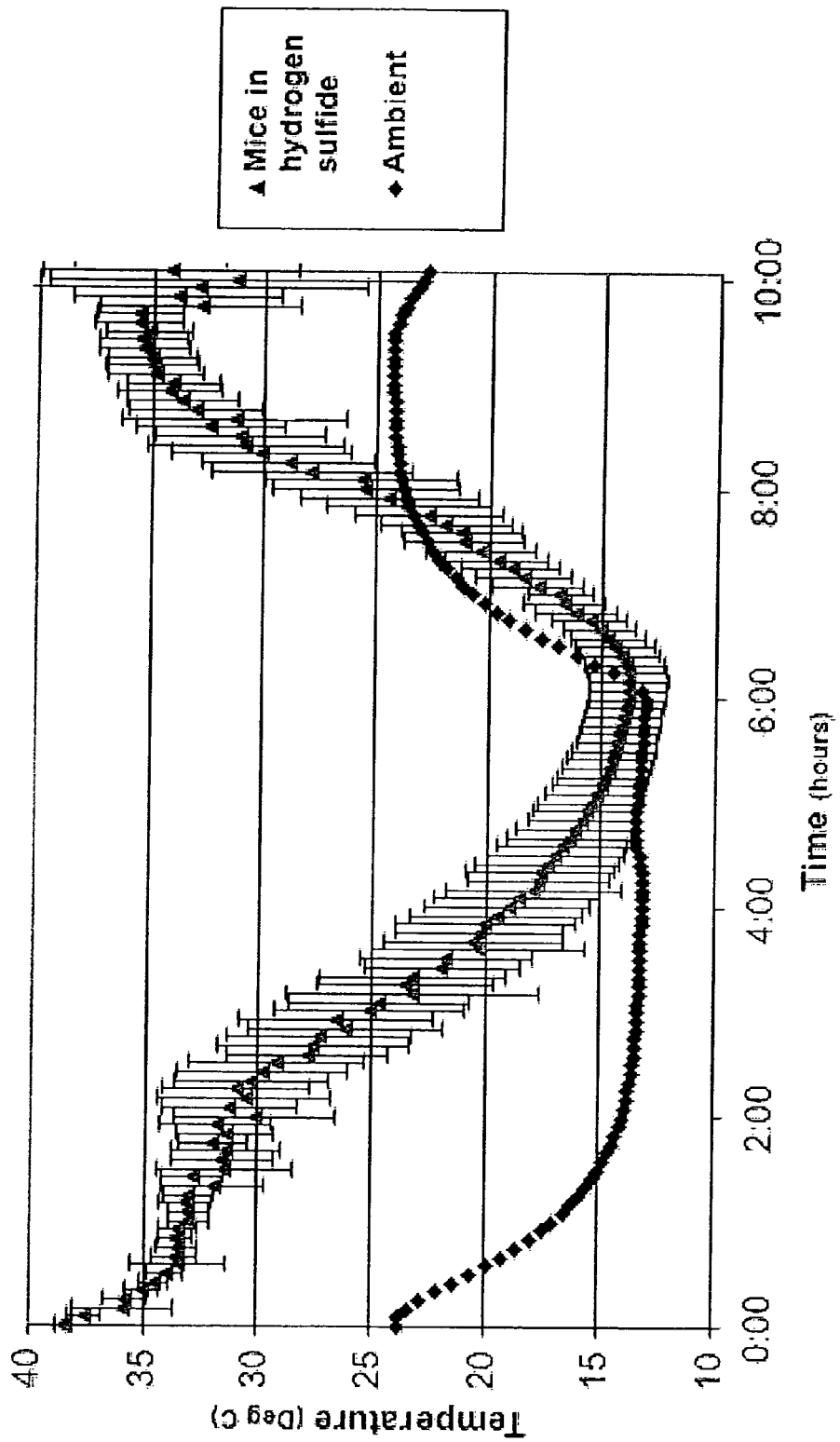
FIG. 5B Exposure to 80 ppm hydrogen sulfide causes the average core body temperature of mice to approach ambient temperature. The average core body temperature of seven mice exposed to 80 ppm of hydrogen sulfide for 6 hrs was measured as described in the legend for FIG. 5A. The core body temperature followed a similar pattern as to the measurement of a single mouse shown in FIG. 5A.
Figure 5C:
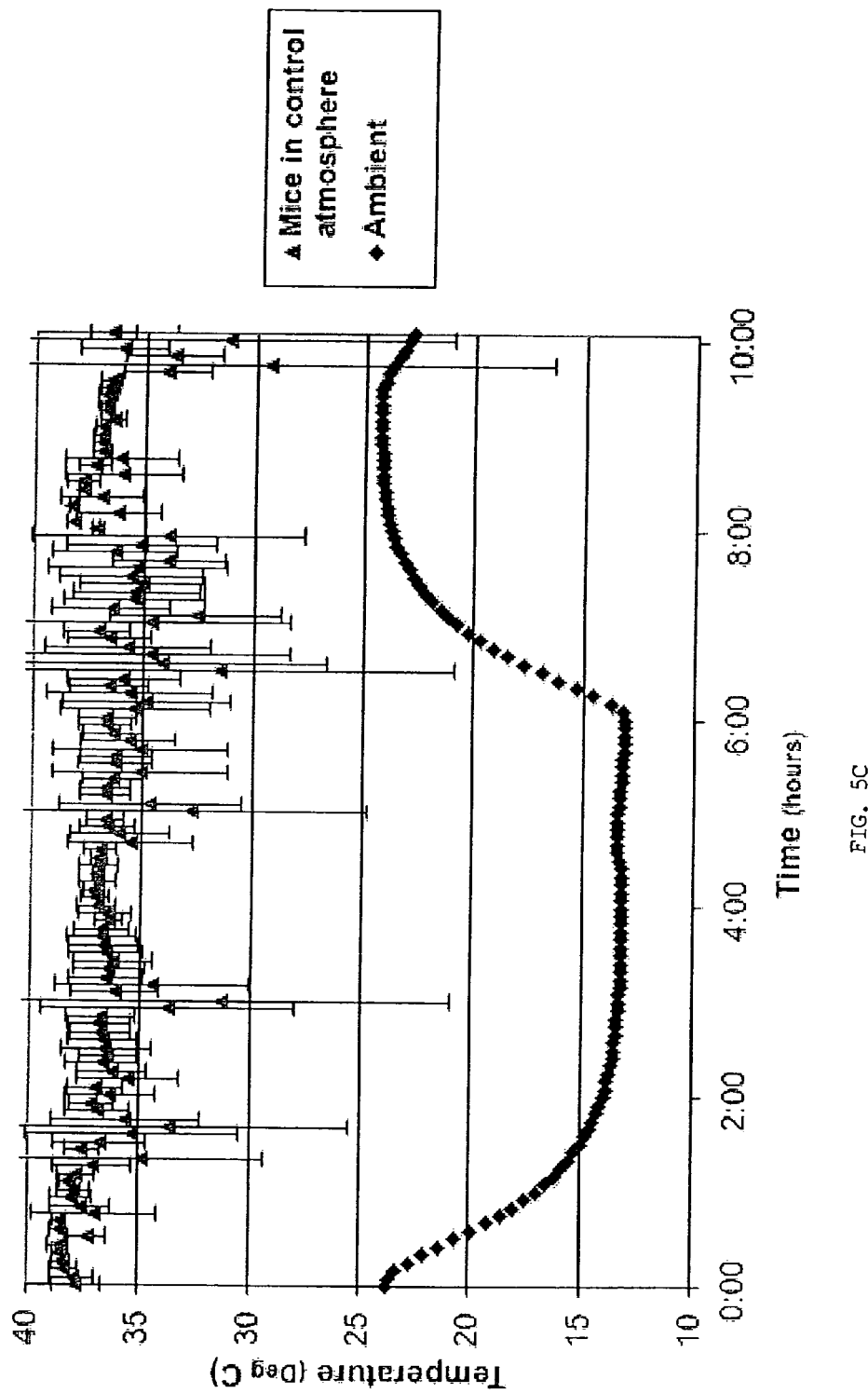
FIG. 5C Exposure to nitrogen does not change the average core body temperature of mice. Nitrogen was substituted for the hydrogen sulfide and core body temperature was measured as in FIG. 5A. The average core body temperature is shown.
Figure 6:
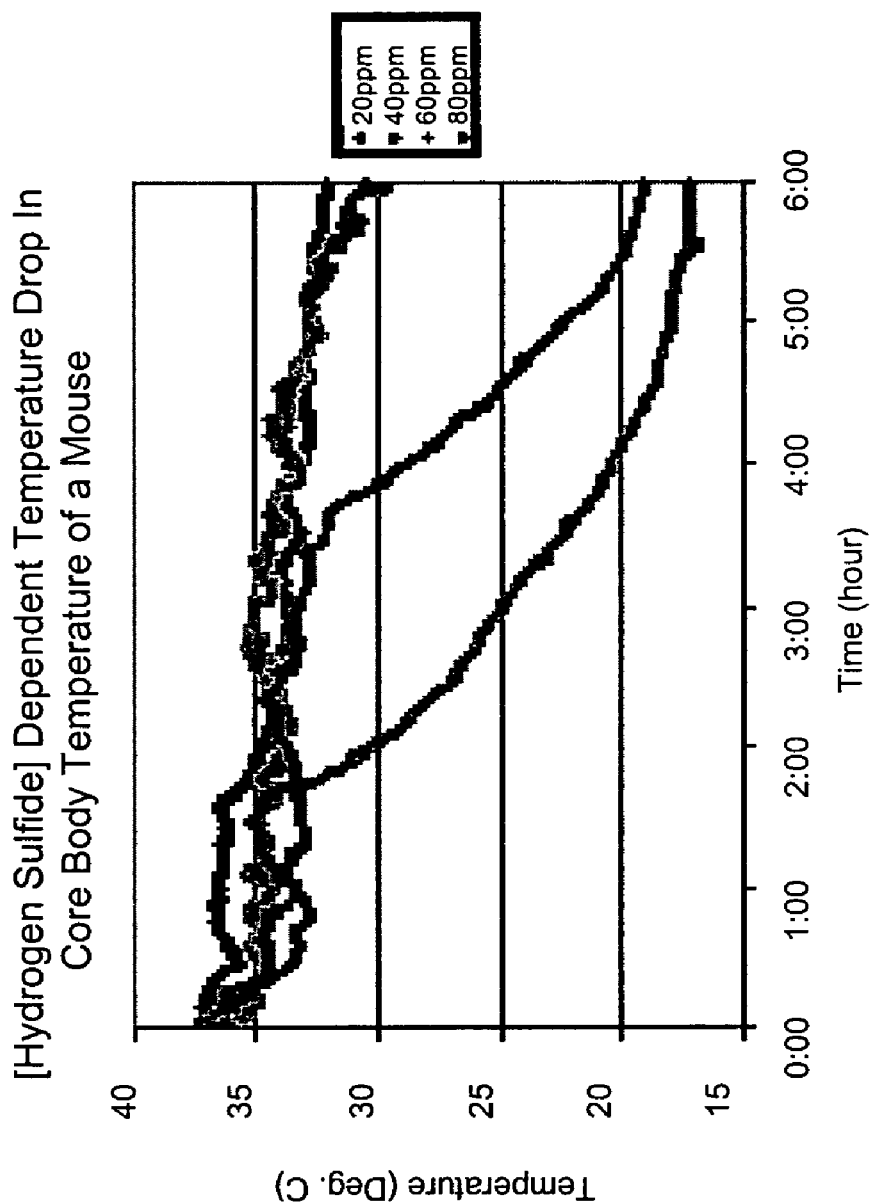
FIG. 6—The rate of body core temperature drop is dependent upon the concentration of hydrogen sulfide given to the mice. All lines represent core body temperature of a single mouse as determined by radiotelemetry. Mice subjected to 20 ppm and 40 ppm $H_2S$ exhibit minor drops in core temperature. Exposure to 60 ppm induced a substantial drop in temperature beginning at approximately hour 4:00. The mouse exposed to 80 ppm exhibited a substantial drop in temperature beginning at approximately hour 2:00.

Exposing a mouse to 80 ppm $H_2S$ dropped its core temperature to approximately two degrees Celsius above ambient (FIG. 5A). This effect was highly reproducible as the average core body temperature of seven mice exposed to 80 ppm of hydrogen sulfide for 6 hrs followed a similar pattern (FIG. 5B). The lowest average core body temperature of these seven mice was 15° C. in an ambient temperature of 13° C. All of these mice successfully recovered after rewarming when the atmosphere was switched to one containing only room air. As a control, the inventor substituted nitrogen for the hydrogen sulfide and did not see the substantial drop in core body temperature (FIG. 5C).

Although these mice appear superficially normal despite temporary decrease in both core body temperature and breathing rate, the inventor conducted a battery of behavior tests to rule out the possibility that neurological damage was incurred by either the exposure to hydrogen sulfide gas, the extreme reduction in core body temperature, the reduction in breathing rate, or the combination of these effects. All of the tests were performed on the mice both before and after exposure to hydrogen sulfide. These behavior tests were selected from the SHIRPA protocol developed by the Mouse Models for Human Disease consortium (Rogers et al., 1997). There were no detectable behavioral differences in the mice after gas exposure. From this, the inventor concluded that entry into a hibernation-like state is not detrimental.

Preliminary Optimization of $H_2S$ Dose. The above experiments describe the effect of 80 ppm of hydrogen sulfide on the core body temperature of a mouse. In order to determine the concentration of hydrogen sulfide sufficient for the loss of thermoregulation, the inventor exposed mice to a range of hydrogen sulfide concentrations (20 ppm, 40 ppm, 60 ppm, and 80 ppm), (FIG. 6). While 20 ppm and 40 ppm of hydrogen sulfide were sufficient to cause a drop in the core body temperature of a mouse, this was minor compared to the drop seen with 60 ppm and 80 ppm of hydrogen sulfide. From this experiment, the inventor concluded that the loss of thermogenesis is directly dependent upon the concentration of hydrogen sulfide given to the mice. This preliminary study on the dose range and pharmacokinetics of hydrogen sulfide emphasizes the need for a more comprehensive analysis.

Figure 7:
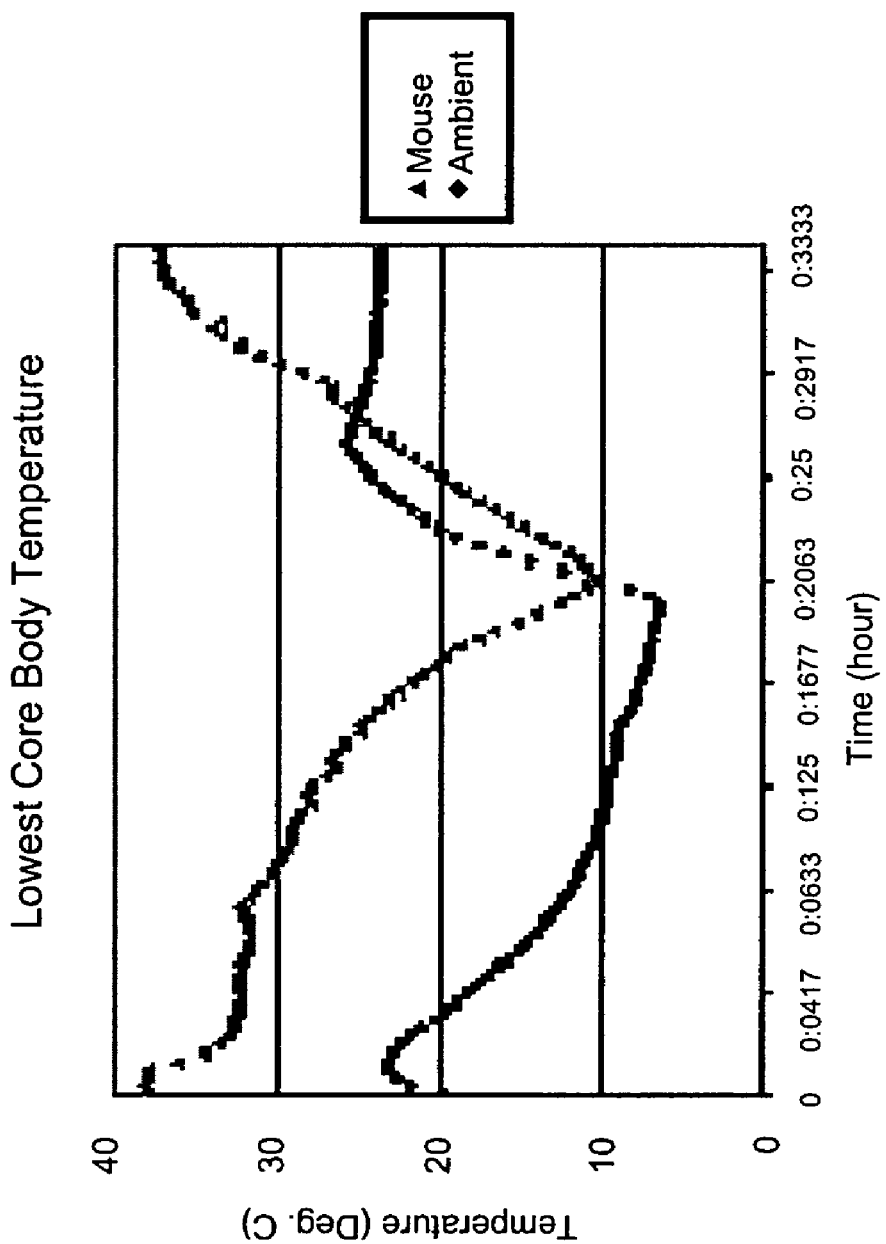
FIG. 7—Lowest core body temperature. The lowest core body temperature recorded for a mouse exposed to 80 ppm hydrogen sulfide was 10.7° C. Triangles indicate the core body temperature of the mouse as determined by radiotelemetry which started at approximately 39° C. at time 0. Diamonds indicate the ambient temperature which began at approximately 23° C. and was dropped to less than 10° C. by the mid-point of the experiment, after which it was then increased again toward room temperature.

Preliminary Definition of Low Core Temperature Limit. The inventor is also interested in establishing a more complete understanding of the tolerance of both the range of core body temperatures and the length of time allowed in this state for mice. The experiments above show that the inventor can repeatedly lower the core body temperature of a mouse to 13-15° C. on demand. Furthermore, the mice seem to tolerate the treatment for many hours. Using the same protocol, while lowering the ambient temperature, the inventor has successfully brought the core body temperature of a mouse to 10.7° C. (FIG. 7). Further attempts to push core body temperatures even lower, and for longer periods of time, will be performed in the future. Although preliminary, these results demonstrate that there is a significant range of core body temperatures allowed by mouse biology and that this range can be explored through the loss of thermoregulation due to hydrogen sulfide exposure.

Figure 8:
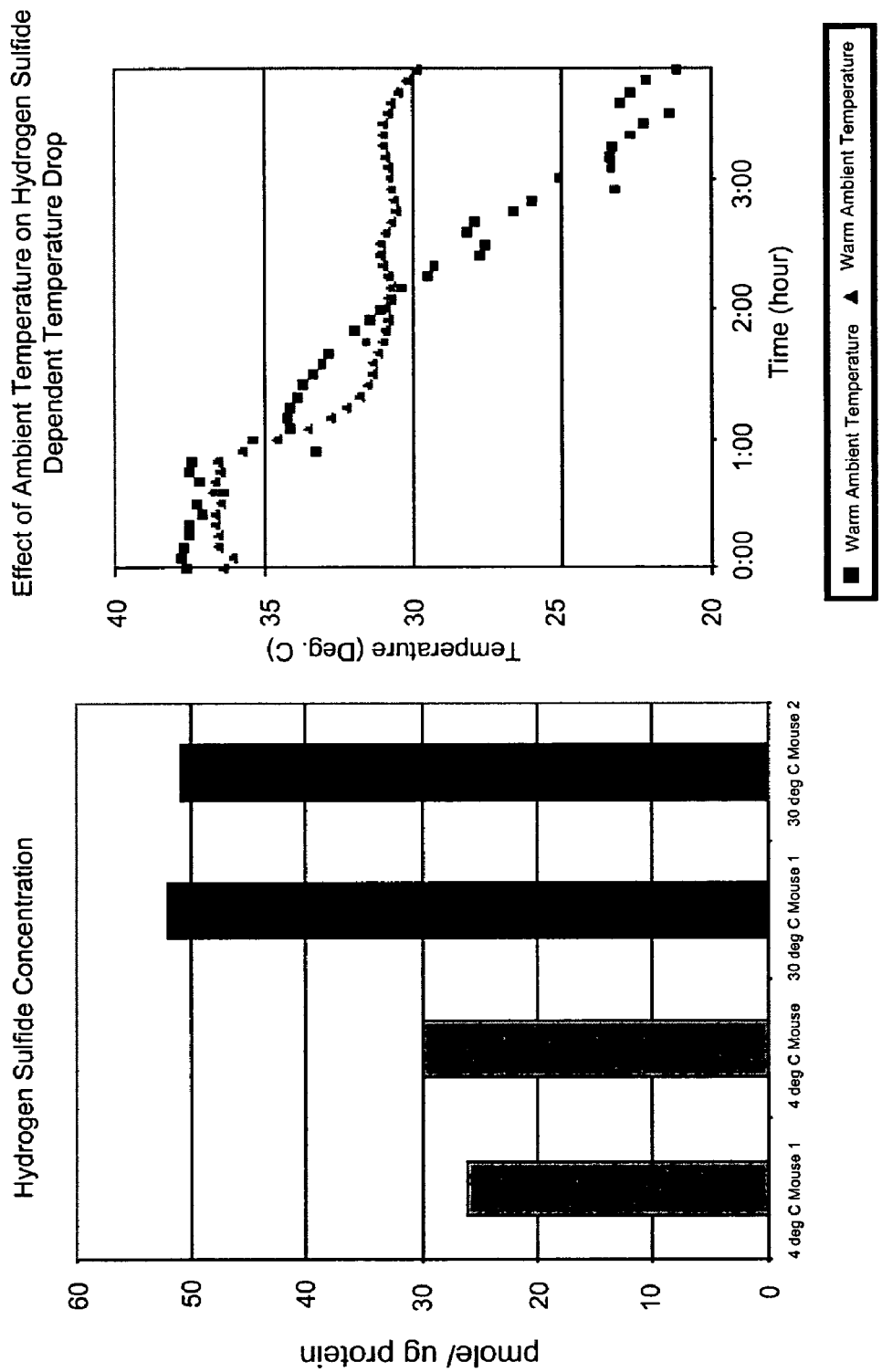
FIG. 8A—Endogenous levels of hydrogen sulfide are increased in mice acclimated to warm temperatures. Gray bars (two left bars) indicate endogenous $H_2S$ concentrations of two individual mice acclimated to 4° C.; black bars (two right bars) indicate the endogenous H2S concentrations of two individual mice acclimated to 30° C. Hydrogen sulfide concentration determined by GC/MS.
FIG. 8B—Effects of Ambient Temperature on Hydrogen Sulfide Dependent Temperature Drop. The rate of core temperature (expressed in degrees Centigrade) drop due to hydrogen sulfide exposure is dependent on the acclimation temperature. The mice were exposed to the gas at 1:00. Triangles indicate the core body temperature of the mouse, acclimated to 12° C., as determined by radiotelemetry. Squares indicate the core body temperature of the animal acclimated to 30° C.

Modulation of Endogenous $H_2S$ Levels. It is well known that mammalian cells make hydrogen sulfide endogenously (Wang 2002). Since this chemical is dynamically produced in the cell, it is crucial to understand the basal levels under different conditions as this could dramatically affect the pharmacokinetics of exogenously administered hydrogen sulfide. To address this essential aspect of our research, the inventor has begun to assay endogenous hydrogen sulfide levels in the mouse. The inventor uses an extractive alkylation technique coupled with gas chromatography and mass specific detection to quantify hydrogen sulfide (Hyspler et al., 2002). Using this method, the inventor looked at the levels of hydrogen sulfide in unperturbed mice. FIG. 8A shows that there is a significant amount of hydrogen sulfide within the mouse. Additionally, the levels of hydrogen sulfide appear to be dependent upon the ambient temperature of the mouse. Specifically, when mice are in the cold, they have reduced endogenous sulfide levels and, when mice are at warm ambient temperatures, they have increased endogenous sulfide levels. From this, the inventor concludes that mice regulate their sulfide levels in response to the ambient temperature.

Changes in Endogenous Levels Affect the Efficacy of $H_2S$. Since the ambient temperature changes the endogenous levels of sulfide in mice, the inventors hypothesized that the ambient temperature might impact the changes in core body temperature upon exposure to exogenous hydrogen sulfide. Acclimatizing a mouse to cold temperatures, ~12° C., creates a longlasting plateau that the inventor sees after the initial drop in core body temperature (FIG. 8B). Therefore it appears that this acclimatization to the cold made the mouse more resistant to core body cooling by the action of hydrogen sulfide gas. However, allowing the mouse to acclimatize to a warm thermoneutral temperature prior to gas exposure eliminates this plateau. In fact, the normothermic mouse cooled much more quickly when exposed to hydrogen sulfide than the cold-acclimated mouse (FIG. 8B). These data suggest that endogenous levels of hydrogen sulfide in the mouse have a direct impact upon the efficacy of the exogenous hydrogen sulfide.

$H_2S$ protects mice from hypoxia. Normal room air contains approximately 21% oxygen. In a preliminary experiment exploring the protective effects of stasis on hypoxia in the mouse model, a mouse exposed to 80 ppm of hydrogen sulfide survived 11 minutes of 5.2% oxygen and 3 weeks later, it was still doing well. Previously published work shows that 90% of these animals (C57B1) exposed in this way without hydrogen sulfide do not survive (Zhang et al., 2004). This experiment involved pre-equilibrating the mouse to 80 ppm $H_2S$ for 3 hours, then dropping the oxygen tension in the chamber as described in experiments above. The same flow rates were used as described above (i.e., 500 cc/mL in a 0.5 L chamber). It is well established in those familiar with the field that if a group of mice are exposed to 4% oxygen, 100% will be dead within 15 minutes. However, mice in which $H_2S$ is administered during periods when the oxygen tension is reduced to 4%, remain viable, even for extended periods (up to an hour) in these hypoxic conditions. The mice appear to be unaffected by these conditions after recovery, and are viable and normally responsive when tested 24 hours later. This experiment differs from the one above in that the mice were retained in the $H_2S$ at the end of the hypoxic exposure until the oxygen tensions were returned to normal levels (21% $O_2$).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,777,507
U.S. Pat. No. 3,881,990
U.S. Pat. No. 3,995,444
U.S. Pat. No. 4,034,753
U.S. Pat. No. 4,186,565
U.S. Pat. No. 4,266,573
U.S. Pat. No. 4,292,817
U.S. Pat. No. 4,442,856
U.S. Pat. No. 4,447,415
U.S. Pat. No. 4,473,637
U.S. Pat. No. 4,502,295
U.S. Pat. No. 4,559,258
U.S. Pat. No. 4,745,759
U.S. Pat. No. 4,798,824
U.S. Pat. No. 4,828,976
U.S. Pat. No. 4,938,961
U.S. Pat. No. 4,951,482
U.S. Pat. No. 5,066,578
U.S. Pat. No. 5,157,930
U.S. Pat. No. 5,217,860
U.S. Pat. No. 5,231,025
U.S. Pat. No. 5,285,657
U.S. Pat. No. 5,326,706
U.S. Pat. No. 5,370,989
U.S. Pat. No. 5,395,314
U.S. Pat. No. 5,399,363
U.S. Pat. No. 5,405,742
U.S. Pat. No. 5,466,468
U.S. Pat. No. 5,470,738
U.S. Pat. No. 5,476,763
U.S. Pat. No. 5,543,158
U.S. Pat. No. 5,552,267
U.S. Pat. No. 5,568,910
U.S. Pat. No. 5,569,579
U.S. Pat. No. 5,580,781
U.S. Pat. No. 5,599,659
U.S. Pat. No. 5,636,643
U.S. Pat. No. 5,641,515
U.S. Pat. No. 5,645,081
U.S. Pat. No. 5,693,462
U.S. Pat. No. 5,699,793
U.S. Pat. No. 5,719,174
U.S. Pat. No. 5,736,397
U.S. Pat. No. 5,739,169
U.S. Pat. No. 5,752,929
U.S. Pat. No. 5,801,005
U.S. Pat. No. 5,830,880
U.S. Pat. No. 5,846,945
U.S. Pat. No. 5,912,019
U.S. Pat. No. 5,952,168
U.S. Pat. No. 6,013,256
U.S. Pat. No. 6,046,046
U.S. Pat. No. 6,046,046
U.S. Pat. No. 6,054,261
U.S. Pat. No. 6,054,261
U.S. Pat. No. 6,057,148
U.S. Pat. No. 6,100,082
U.S. Pat. No. 6,187,529
U.S. Pat. No. 6,365,338
U.S. Pat. No. 6,490,880
U.S. Pat. No. 6,492,103
U.S. Pat. No. 6,524,785
U.S. Pat. No. 6,552,083
U.S. Pat. No. 6,602,277
U.S. Pat. No. 6,790,603
Alam, *Antioxid Redox Signal,* 4(4): 559-62, 2002.
Amersi et al., *Hepatology,* 35(4): 815-823, 2002.
Austin-Ward and Villaseca, *Revista Medica de Chile,* 126(7): 838-845, 1998.
Behringer et al., *Crit. Care Med.,* 31(5): 1523-1531, 2003.
Bellamy et al., *Crit. Care Med.,* 24(2 Suppl): S24-47, 1996.
Bernard et al., *J. Thorac. Cardiovasc. Surg.* 90: 235-242, 1985.
Boyce and Ham, *J. Invest. Dermatol.,* 81: 335-405, 1983.
Boyce and Ham, *J. Tissue Culture Methods,* 9: 83-93, 1985.
Briese, *Neurosci. Biobehav. Rev.,* 22(3): 427-436, 1998.
Brizel, *Seminars Radiation Oncol.,* 8(4Suppl): 17-20, 1998.
Brouard et al., *J. Biol. Chem.,* 277(20): 17950-17961, 2002.
Bukowski et al., *Clinical Cancer Res.,* 4(10): 2337-2347, 1998.
Christodoulides et al., *Microbiology,* 144(Pt 11): 3027-3037, 1998.
CIIT (Chemical Industry Institute of Toxicology), In: *90 day vapor inhalation toxicity study of hydrogen sulfide,* Toxigenics, 420-0710, 1983.
Curran, *Seminars Radiation Oncol.,* 8(4Suppl): 2-4, 1998.
Davidson et al., *J. Immunother.,* 21(5): 389-398, 1998.
Dillman, Cancer Biother. Radiopharm., 14(1): 5-10, 1999.
Dorman et al. Neurotoxicol. Teratol., 22(1): 71-84, 2000.
Dulak et al., *Antioxid. Redox Signal,* 4(2): 229-240, 2002.
Eto et al., *Biochem. Biphys. Res. Commun.,* 293: 1483-1488, 2002.
Ganther, *Carcinogenesis* 20(9): 1657-66 (1999)

Gilbert et al., *LANCET,* 355: 375-376, 2000.
Gorman et al., *Toxicology,* 187(1): 25-38, 2003.
Guillemin et al., *Cell,* 89(1): 9-12, 1997.
Haase et al., *Annals of Surgery,* 240(2): 364-373, 2004.
Hanibuchi et al., *Intl. J. Cancer,* 78(4): 480-45, 1998.
Hays, In: *Studies of the Effects of Atmospheric Hydrogen Sulfide in Animals,* thesis dissertation, University of Missouri-Columbia, 1972.
Hellstrand et al., *Acta Oncologica,* 37(4): 347-353, 1998.
Higuchi and Fukamachi, *Folia Pharmacologica Japonica,* 73(3): 307-319, 1977.
Hochachka et al., *Comp. Biochem. Physiol. B Biochem. Mol. Biol.,* 130(4): 435-459, 2001.
Hochachka et al., *Proc. Natl. Acad. Sci. USA,* 93(18): 9493-94938, 1996.
Hui and Hashimoto, *Infection Immun.,* 66(11): 5329-5336, 1998.
Hyspler et al., *J. Chromatography,* 770: 255-259, 2002.
Jiang et al., *Am. J. Physiol. Cell Physiol.,* 280: 1140-1150, 2001.
Ju et al., *J. Neuropathol. Exp. Neurol.,* 59(3): 241-50, 2000.
Khan et al., *Toxicol. Applied Pharmacol.,* 103: 482-490, 1990.
Kilburn and Warshaw, *Toxicology Indust. Health,* 11(2): 185-197, 1995.
Kilburn, *Environ. Health,* 54(3): 150, 1999
Kilburn, *Environ. Res.,* 81(2): 92-99, 1999.
Kubulus et al., In: *The mechanism of the delay phenomenon: tissue protection is mediated by heme oxygenase-1,* Institute for Clinical Experimental Surgery, Univ. of Saarland, Germany, 1-21, 2004.
Kuroda et al., *Transplantation,* 46(3): 457-460, 1988.
Kuroda et al., *Transplantation,* 46(3): 457-460, 1988.
Ledingham et al., *Circulation* 82 (Part 2) IV351-8, 1990.
Ledingham et al., *Circulation,* 82(2): IV351-358, 1990.
Ledingham et al., *J. Thorac. Cardiobasc. Surg.* 93: 240-246, 1987.
Ledingham et al., *J. Thorac. Cardiobasc. Surg.,* 93: 240-246, 1987.
Lundgren-Eriksson et al., Anticancer Res. 2001 September-October; 21(5): 3269-74
Menasche et al., *Eur. J. Cardio. Thorax. Surg.* 8: 207-213, 1994.
Menasche et al., *Eur. J. Cardio. Thorax. Surg.,* 8: 207-213, 1994
Nystul et al., *Science,* 302(5647): 1038-1041, 2003.
Otterbein et al., *Am. J. Physiol. Lung Cell Mol. Physiol.,* 279(6): L1029-L1037, 2000.
Otterbein et al., *Trends Immunol.,* 24(8): 449-455, 2003.
Padilla et al., *Molec. Biology of the Cell,* 13: 1473-1483, 2002.
Padilla et al., *Proc. Natl. Acad. Sci. USA,* 98(13): 7331-7335., 2001.
Partlo et al., *Neurotoxicology,* 22(2): 177-189, 2001.
Petersen, *Biochemica et Biophysica Acta,* 460: 299-307, 1977.
Pietras et al., *Oncogene,* 17(17): 2235-2249, 1998.
Qin et al., *Proc. Natl. Acad. Sci. USA,* 95(24): 14411-14416, 1998.
Remington's Pharmaceutical Sciences, 15th ed., pages 1035-1038 and 1570-1580, Mack Publishing Company, Easton, Pa., 1980.
Roger et al., *Genome,* 8: 711-713, 1997.
Ryter and Otterbein, *BioEssays,* 26: 270-280, 2004.
Semenza, *Cell,* 98(3): 281-284, 1999.
Semenza, *Trends Mol. Med.,* 7(8): 345-350, 2001.
Struve et al., *Neurotoxicology,* 22(3): 375-385, 2001.
Teodoro and OFarrell, *EMBO J.,* 22(3): 580-587, 2003.
Tisherman, *Crit. Care Med.,* 32(2): S46-S50, 2004.
Van Voorhies et al., *J. Exp. Biol.,* 203(Pt 16): 2467-2478, 2000.
Wang, *FASEB J.,* 16(13): 1792-1798, 2002.
Zhang et al., *J. Appl. Physiol.* 96(1): 392-397, 2004.

What is claimed is:

1. A method for inducing stasis in human tissue for transplantation comprising
   a) isolating human tissue for transplantation;
   b) exposing the tissue to an oxygen antagonist, wherein the oxygen antagonist is hydrogen sulfide;
   c) halting exposure of the tissue to the oxygen antagonist; and
   d) transplanting the tissue in a live recipient.

2. The method of claim 1, wherein the tissue is selected from the group of systems consisting of circulatory, digestive, endocrine, integumentary, muscular, nervous, reproductive, respiratory, skeletal, and urinary systems.

3. The method of claim 2, wherein the tissue is all or part of an organ selected from the group consisting of heart, thymus, skin, bone, spleen, stomach, intestine, liver, pancreas, ovary, testes, pituitary gland, pineal gland, thyroid gland, lung, retina, kidney, and umbilical cord.

4. The method of claim 1, wherein the tissue comprises the following cell types
   platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell, stem cell, unfertilized or fertilized oocyte, or sperm.

5. The method of claim 1, wherein the effective amount is a sublethal dose of the oxygen antagonist.

6. The method of claim 1, wherein the oxygen antagonist is a gas, semi-solid liquid, or liquid.

7. The method of claim 6, wherein the oxygen antagonist is a gas.

8. The method of claim 1, further comprising subjecting the tissue to a controlled temperature environment.

9. The method of claim 8, further comprising modulating environmental oxygen levels or removing the tissue from an environment having oxygen.

10. The method of claim 1, further comprising assessing the level of the oxygen antagonist and/or oxidative phosphorylation in the tissue.

11. The method of claim 1, further comprising removing the oxygen antagonist.

12. The method of claim 1, further comprising placing the tissue under a vacuum.

13. The method of claim 7, wherein the gas is a gas mixture comprising more than one gas.

14. The method of claim 13, wherein the other gas(es) is non-toxic and non-reactive.

15. The method of claim 14, wherein the non-toxic, non-reactive gas is helium, hydrogen, nitrogen, argon, neon, krypton, xenon, radon, or ununoctium.

16. The method of claim 7, wherein the gas is mixed with oxygen to form an oxygen gas mixture.

17. The method of claim 16, wherein the amount of oxygen in the oxygen gas mixture is less than the total amount of all other gas or gases in the mixture.

18. The method of claim 16, wherein the gas is carbon monoxide and the amount of carbon monoxide is about the same or exceeds any amount of oxygen in the oxygen gas mixture.

19. The method of claim 6, wherein the tissue is exposed to the oxygen antagonist in a closed environment.

20. The method of claim 19, wherein exposing the tissue to the oxygen antagonist comprises placing the tissue in a container that maintains the environment.

21. The method of claim 7, wherein the tissue is exposed to a normoxic environment after being exposed to the gaseous oxygen antagonist.

22. The method of claim 1, wherein the tissue is exposed to the oxygen antagonist in an environment that is at room temperature.

23. The method of claim 18, wherein the ratio of carbon monoxide to oxygen is at least 199:1.

24. The method of claim 23, wherein the wherein the ratio of carbon monoxide to oxygen is at least 399:1.

25. The method of claim 1, wherein the tissue is exposed to the oxygen antagonist by perfusion or incubation with the oxygen antagonist.

26. The method of claim 1, wherein the tissue is obtained from a donor subject administered extracorporeal membrane oxygenation prior to retrieval of the sample.

27. A method for inducing stasis in human tissue for transplantation comprising
   a) administering an oxygen antagonist to the tissue, wherein the oxygen antagonist is hydrogen sulfide;
   b) halting administration of the oxygen antagonist to the tissue;
   c) isolating the tissue before administration of the oxygen antagonist; and
   d) preserving the tissue for transplantation.

* * * * *